US008114884B2

(12) United States Patent
Shim et al.

(10) Patent No.: US 8,114,884 B2
(45) Date of Patent: *Feb. 14, 2012

(54) CXCR4 ANTAGONISTS FOR THE TREATMENT OF MEDICAL DISORDERS

(75) Inventors: Hyunsuk Shim, Atlanta, GA (US);
Dennis C. Liotta, Atlanta, GA (US);
James P. Snyder, Atlanta, GA (US);
Weiqiang Zhan, Decatur, GA (US);
Zhongxing Liang, Tucker, GA (US)

(73) Assignee: Emory University, Atlanta, GA (US)

( * ) Notice: Subject to any disclaimer, the term of this patent is extended or adjusted under 35 U.S.C. 154(b) by 1033 days.

This patent is subject to a terminal disclaimer.

(21) Appl. No.: 11/328,900

(22) Filed: Jan. 9, 2006

(65) Prior Publication Data

US 2007/0054930 A1    Mar. 8, 2007

Related U.S. Application Data

(60) Provisional application No. 60/642,375, filed on Jan. 7, 2005, provisional application No. 60/642,374, filed on Jan. 7, 2005, provisional application No. 60/682,655, filed on May 18, 2005, now abandoned.

(51) Int. Cl.
*A01N 43/54* (2006.01)
*A01N 43/40* (2006.01)
*A61K 31/505* (2006.01)
*A61K 31/44* (2006.01)
*C07D 401/00* (2006.01)
*C07D 403/00* (2006.01)
*C07D 405/00* (2006.01)
*C07D 409/00* (2006.01)

(52) U.S. Cl. ........ 514/275; 514/332; 544/330; 544/331; 544/332

(58) Field of Classification Search ................. 514/275, 514/332; 544/330, 331, 332
See application file for complete search history.

(56) References Cited

U.S. PATENT DOCUMENTS

| | | | |
|---|---|---|---|
| 5,874,438 A | 2/1999 | Schohe-Loop et al. | |
| 5,993,817 A | 11/1999 | Yoneda et al. | |
| 6,344,545 B1 | 2/2002 | Allaway et al. | |
| 6,358,915 B1 | 3/2002 | Patierno et al. | |
| 6,420,354 B1 | 7/2002 | Marquess et al. | |
| 6,429,308 B1 | 8/2002 | Iijima et al. | |
| 6,433,149 B1 | 8/2002 | Blaschuk et al. | |
| 6,475,488 B1 | 11/2002 | Pasqualini et al. | |
| 6,534,626 B1 | 3/2003 | Oravecz et al. | |
| 6,750,348 B1 | 6/2004 | Bridger et al. | |
| 2002/0039993 A1* | 4/2002 | Winchester et al. | 514/2 |
| 2002/0147192 A1* | 10/2002 | Bridger et al. | 514/227.5 |
| 2004/0132642 A1 | 7/2004 | Hwang | |
| 2004/0254221 A1 | 12/2004 | Yamamazi et al. | |
| 2006/0264378 A1* | 11/2006 | Fujii et al. | 514/14 |
| 2007/0054930 A1 | 3/2007 | Shim et al. | |
| 2008/0227799 A1 | 9/2008 | Liotta et al. | |
| 2009/0099194 A1 | 4/2009 | Liotta et al. | |

FOREIGN PATENT DOCUMENTS

| | | |
|---|---|---|
| EP | 515684 | 12/1992 |
| WO | WO 91/11994 | 8/1991 |
| WO | WO 97/00956 A1 | 1/1997 |
| WO | WO 99/47158 A2 | 9/1999 |
| WO | WO 00/56729 A1 | 9/2000 |
| WO | WO 01/38352 A2 | 5/2001 |
| WO | WO 01/56591 A1 | 8/2001 |
| WO | 01-70727 A1 | 9/2001 |
| WO | WO 01/85196 A2 | 11/2001 |
| WO | WO 02/02516 | 1/2002 |
| WO | WO 02/094261 A1 | 11/2002 |
| WO | WO 03/029218 A1 | 4/2003 |
| WO | WO 2004/020462 A1 | 3/2004 |
| WO | WO 2004/024178 A1 | 3/2004 |
| WO | WO 2004/093817 A2 | 4/2004 |
| WO | WO 2004/059285 A2 | 7/2004 |
| WO | WO 2004/087068 A2 | 10/2004 |
| WO | WO 2004/091518 A2 | 10/2004 |
| WO | WO 2004/106493 A2 | 12/2004 |
| WO | WO 2005/049607 | 6/2005 |

OTHER PUBLICATIONS

Furst (Brit J of Rheumatology, 1997, 36, 1196-1204).*
Banker, Gilbert S. et al., Modem Pharmaceutics, Marcel Dekker, New York, 1996.*
Wolff, Manfred E., Burger's Medicinal Chemistry and Drug Discovery, Fifth Ed., vol. 1: Principles and Practice, John Wiley & Sons, 1995, 975-77.*
(http://www.ncbi.nlm.nih.gov/pubmedhealth/PMH0001819/), 2011—Autoimmune Disorders Document.*
(http://en.wikipedia.org/wiki/Inflammation) 2011, Inflammation Document.*
Abdel-Magid, A.F., et al., "Reductive Amination of Aldehydes and Ketones with Sodium Triace-toxyborohydride. Studies on Direct and Indirect Reductive Amination Procedures(1)," *J. Org. Chem.* 61(11):3849-3862 (May 31, 1996).
Abi-Younes, S., et al., "The stromal cell-derived factor-1 chemokine is a potent platelet agonist highly expressed in atherosclerotic plaques," *Circ. Res.*, 86(2), 131-138 (Feb. 4, 2000)).
Alkhatib, G., et al., "CC CKR5: a RANTES, MIP-1alpha, MIP-1beta receptor as a fusion cofactor for macrophage-tropic HIV-1," *Science*, 272(5270):1955-1958 (Jun. 28, 1996).
Blades, M.C., et al., "Stromal cell-derived factor 1 (CXCL12) induces hu-man cell migration into human lymph nodes transplanted into SCID mice," *J. Immunol.* 168(9):4308-4317 (May 1, 2002).
Bleul, C.C., et al., "The lymphocyte chemoattractant SDF-1 is a ligand for LESTR/fusin and blocks HIV-1 entry," *Nature*, 382(6594):829-833 (Aug. 29, 1996).

(Continued)

*Primary Examiner* — Sreeni Padmanabhan
*Assistant Examiner* — Uma Ramachandran
(74) *Attorney, Agent, or Firm* — Emory Patent Group; James C. Mason; Susanne Hollinger

(57) ABSTRACT

The invention provides compounds, pharmaceutical compositions and methods of use of certain compounds that are antagonists of the chemokine CXCR4 receptor for the treatment of proliferative conditions mediated by CXCR4 receptors. The compounds provided interfere with the binding of SDF1 to the receptor. These compounds are particularly useful for treating or reducing the severity of hyperproliferative diseases by inhibiting metastasis.

1 Claim, 16 Drawing Sheets

OTHER PUBLICATIONS

Braun, C.E., et al., "Guanidine structure and hypoglycemia: some carbocyclic diguanidines," *J. Org. Chem.*, 3(2):146-152 (1938).

Bressler, N.M., and Bressler, S.B., "Preventative ophthalmology. Age-related macular degenera-tion," *Ophthalmology*, 102(8):1206-1211 (Aug. 1995).

Butcher, E.C., et al. "Lymphocyte trafficking and regional immu-nity," *Adv. Immunol.*, 72:209-253 (1999).

Campbell, J.J., and Butcher, E.C., "Chemokines in tissue-specific and microenvironment-specific lymphocyte homing," *Curr. Opin. Immunol.*, 12(3):336-341 (Jun. 2000).

Chen, W.J., et al. "Recombinant human CXC-chemokine receptor-4 in melanophores are linked to Gi protein: seven transmembrane coreceptors for human immunodeficiency virus entry into cells," *Mol. Pharmacol.*, 53(2):177-181 (Feb. 1998).

Connor, R.I., et al., "Change in coreceptor use correlates with disease progression in HIV-1—infected individuals," *J. Exp. Med.*, 185(4):621-628 (Feb. 17, 1997).

Crane, I.J., et al., "CXCR4 receptor expression on human retinal pigment epithelial cells from the blood-retina barrier leads to chemokine secretion and migration in response to stromal cell-de-rived fac-tor 1 alpha," *J. Immunol.*, 165(8):4372-4378 (Oct. 15, 2000).

Davis, C.B., et al. "Signal transduction due to HIV-1 envelope inter-actions with chemokine receptors CXCR4 or CCR5," *J. Exp. Med.*, 186(10):1793-1798 (Nov. 17, 1997).

Deng, H.K., et al., "Expression cloning of new receptors used by simian and human immunodeficiency viruses," *Nature*, 388(6639):296-300 (Jul. 17, 1997).

Donzella, G.A., et al., "AMD3100, a small molecule inhibitor of HIV-1 entry via the CXCR4 co-receptor," *Nat. Med.*, 4(1):72-77 (Jan. 1998).

Doranz, B.J., et al., "A dual-tropic primary HIV-1 isolate that uses fusin and the beta-chemokine re-ceptors CKR-5, CKR-3, and CKR-2b as fusion cofactors," *Cell*, 85(7):1149-1158 (Jun. 28, 1996).

Dwinell, M.B., et al., "Chemokine receptor expression by human intestinal epithelial cells," *Gastro-enterology*, 117(2):359-367 (Aug. 1999).

Eitner, F., et al., "Chemokine receptor (CXCR4) mRNA-expressing leukocytes are increased in hu-man renal allograft rejection," *Trans-plantation*, 66(11):1551-1557 (Dec. 15, 1998).

Feng, Y, et al., "HIV-1 entry cofactor: functional cDNA cloning of a seven-transmembrane, G protein-coupled receptor," *Science*, 272(5263):872-877 (May 10, 1996).

Förster, R., et al., "CCR7 coordinates the primary immune response by establishing functional mi-croenvironments in secondary lymphoid organs," *Cell*, 99(1):23-33 (Oct. 1, 1999).

Fujii, N., et al., "The therapeutic potential of CXCR4 antagonists in the treatment of HIV," *Expert Opin. Investig. Drugs*, 12(2):185-195 (Feb. 2003).

Gonzalo, J.A., et al., "Critical involvement of the chemotactic axis CXCR4/stromal cell-derived fac-tor-1 alpha in the inflammatory component of allergic airway disease," *J. Immunol.*, 165(1),499-508 (Jul. 1, 2000).

Grove, G., "Epidermal cell kinetics in psoriasis," *Int. J. Dermatol.*, 18(2):111-122 (Mar. 1979).

Gupta, S.K., et al., "Chemokine receptors in human endothelial cells. Functional expression of CXCR4 and its transcriptional regulation by inflammatory cytokines," *J. Biol. Chem.*, 273(7):4282-4287 (Feb. 13, 1998).

Harris, E. D., Jr., "Rheumatoid arthritis. Pathophysiology and impli-cations for therapy," *N. Eng. J. Med.*, 322(18):1277-1289 (May 3, 1990).

Hatse, S., et al., "Chemokine receptor inhibition by AMD3100 is strictly confined to CXCR4," *FEBS Lett* 527(1-3):255-262 (Sep. 11, 2002).

Hendrix, C.W., et al., "Safety, pharmacokinetics, and antiviral activ-ity of AMD3100, a selective CXCR4 receptor inhibitor, in HIV-1 infection," *J. Acquir. Immune Defic. Syndr.*, 37(2):1253-1262 (Oct. 1, 2004).

Homey, B., et al., "Cutting edge: the orphan chemokine receptor G protein-coupled receptor-2 (GPR-2, CCR10) binds the skin-associ-ated chemokine CCL27 (CTACK/ALP/ILC)," *J. Immunol.*, 164(7):3465-3470 (Apr. 1, 2000).

Kang, Y., et al., "A multigenic program mediating breast cancer metastasis to bone," *Cancer Cell*, 3(6):537-549 (Jun. 2003).

Kijowski, J., et al., "The SDF-1-CXCR4 axis stimulates VEGF secre-tion and activates integrins but does not affect proliferation and survival in lymphohematopoietic cells," *Stem Cells* 19(5):453-466 (2001).

Linton, B.R., et al., "Thermodynamic aspects of dicarboxylate rec-ognition by simple artificial recep-tors," *J. Org. Chem.*, 66(22):7313-7319 (Nov. 2, 2001).

Majka, M., et al., "Biological significance of chemokine receptor expression by normal human mega-karyoblasts," *Folia. Histochem. Cytobiol*. 39(3):235-244 (2001).

Mićović, V.M., and Mihailović, M.LJ., "The Reduction of Acid Amides with Lithium Aluminum Hydride," *J. Org. Chem.*, 18(9):1190-1200 (1953).

Mitra, P., et al., "CXCR4 mRNA expression in colon, esophageal and gastric cancers and hepatitis C infected liver," *Int. J. Oncol.*, 14(5):917-925 (May 1999).

Morales, J., et al., "CTACK, a skin-associated chemokine that pref-erentially attracts skin-homing memory T cells," *Proc. Natl. Acad. Sci. U.S.A.*, 96(25):14470-14475 (Dec. 7, 1999).

Müller, A., et al., "Involvement of chemokine receptors in breast cancer metastasis," *Nature*, 410(6824):50-56 (Mar. 1, 2001).

Murdoch, C., et al., "Functional expression of chemokine receptor CXCR4 on human epithelial cells," *Immunology*, 98(1):36-41 (Sep. 1998).

Murdock, K.C., et al., "Antitumor agents. 2. Bisguanylhydrazones of anthracene-9,10-dicarboxaldehydes," *J. Med. Chem*. 25(5):505-518 (May 1982).

Nagase, H., et al., "Expression of CXCR4 in eosinophils: functional analyses and cytokine-mediated regulation," *J. Immunol.*, 164(11):5935-5943 (Jun. 1, 2000).

Nanki, T., and Lipsky, P.E., et al., "Cutting edge: stromal cell-derived factor-1 is a costimulator for CD4+ T cell activation," *J. Immunol.*, 164(10):5010-5014 (May 15, 2000).

Onuffer, J.J., and Horuk, R., "Chemokines, chemokine receptors and small-molecule antagonists: recent developments," *Trends Pharmacol. Sci.*, 23(10):459-467 (Oct. 2002).

Peled, A., et al., "Dependence of human stem cell engraftment and repopulation of NOD/SCID mice on CXCR4," *Science*, 283(5403):845-848 (Feb. 5, 1999).

Post, D. E., and Van Meir, E. G., "Generation of bidirectional hypoxia/HIF-responsive expression vectors to target gene expression to hypoxic cells," *Gene Ther.*, 8(23):1801-1807 (Dec. 2001).

Reyes, M.J., et al., "Pyridinium N-(2'-azinyl)aminides: regioselec-tive synthesis of N-(2-pyridyl) substi-tuted polyamines," *Tetrahedron*, 58(42):8573-8579 (Oct. 14, 2002).

Ross, R., "The pathogenesis of atherosclerosis: a perspective for the 1990s," *Nature*, 362(6423):801-809 (Apr. 29, 1993).

Sanchez, X., et al., "Activation of HIV-1 coreceptor (CXCR4) medi-ates myelosuppression," *J. Biol. Chem.*, 272(34):27529-27531 (Oct. 31, 1997).

Schols, D., et al., "Bicyclams, a class of potent anti-HIV agents, are targeted at the HIV coreceptor fusin/CXCR-4," *Antiviral Res.*, 35(3):147-156 (Aug. 1997).

Scozzafava, A., et al. "Non-peptidic chemokine receptors antagonists as emerging anti-HIV agents," *J. Enzyme Inhib. Med. Chem.*, 17(2):69-76 (Apr. 2002).

Sotsios, Y., et al., "The CXC chemokine stromal cell-derived factor activates a Gi-coupled phospho-inositide 3-kinase in T lympho-cytes," *J. Immunol.*, 163(11): 5954-5963 (Dec. 1, 1999).

Staller, P., et al., "Chemokine receptor CXCR4 downregulated by von Hippel-Lindau tumour sup-pressor pVHL," *Nature*, 425(6955):307-311 (Sep. 18, 2003).

Tamamura, H., et al., "A low-molecular-weight inhibitor against the chemokine receptor CXCR4: a strong anti-HIV peptide T140," *Biochem. Biophys. Res. Commun.*, 253(3): 877-882 (Dec. 30, 1998).

Tamamura, H., et al., "Development of specific CXCR4 inhibitors possessing high selectivity in-dexes as well as complete stability in serum based on an anti-HIV peptide T140," *Bioorg. Med. Chem. Lett.*, 11(14):1897-1902 (Jul. 23, 2001).

Tamamura, H., et al., "Pharmacophore identification of a specific CXCR4 inhibitor, T140, leads to development of effective anti-HIV agents with very high selectivity indexes," *Bioorg. Med. Chem. Lett.*, 10(23):2633-2637 (Dec. 4, 2000).

Trent, J.O., et al., "Lipid bilayer simulations of CXCR4 with inverse agonists and weak partial ago-nists," *J. Biol. Chem.*, 278(47):47136-47144 (Nov. 21, 2003) (Epublication Sep. 4, 2003).

Vlahakis, S.R., et al., "G protein-coupled chemokine receptors induce both survival and apoptotic signaling pathways," *J. Immunol.* 169(10):5546-5554 (Nov. 15, 2002).

Volin, M.V., et al., "Chemokine receptor CXCR4 expression in endothelium," *Biochem Biophys Res Commnun.*, 242(1):46-53 (Jan. 6, 1998).

Xia, M.Q., and Hyman, B.T., "Chemokines/chemokine receptors in the central nervous system and Alzheimer's disease," *J. NeuroVirol.*, 5(1):32-41 (Feb. 1999).

Yssel, H., et al., "The role of IgE in asthma," *Clin. Exp. Allergy*; 28(28 Suppl. 5):104-109; discussion 117-118 (Nov. 1998).

Zaitseva, M., et al., "Expression and function of CCR5 and CXCR4 on human Langerhans cells and macrophages: implications for HIV primary infection," *Nat. Med.*, 3(12):1369-1375 (Dec. 1997).

Zlotnik, A., and Yoshie, Q., "Chemokines: a new classification system and their role in immunity," *Immunity*, 12(2):121-127 (Feb. 2000).

Zou, R.-Y., et al., "1,4-Bis(pyridine-2-aminomethyl)benzene," *Acta Crystallographica Section E*, E59(9):(online)o1312-o1313 (Sep. 2003) (Provided as publisher's abstract).

Gagliardi et al., "Antiangiogenic and antiproliferative activity of surimin analogues," *Cancer Chemother. Pharmacol.* 1998, vol. 41, pp. 117-124.

Tu et al., Toward the Design of Novel Polynuclear Platinum Antitumor Complexes, Inorganic Chem-istry, 2003, vol. 42 No. 19, pp. 5795-5797.

Coats et al.; Correlation analysis of pyrimidine folic acid antagonists as antibacterial agents; *Eur. J. of Medicinal Chem.*; 14(3), May 1, 1979; pp. 261-270.

Sellarajah, S. et al.; Synthesis of analogues of congo red and evaluation of their anti-prion activity; *J. of Medicinal Chem.*; vol. 47; Jan. 1, 2004; pp. 5515-5534.

Zhan W. et al.; Discovery of small molecule CXCR antagonists; *J. of Medicinal Chem.*; vol. 50 (23); Nov. 1, 2007; pp. 5655-5664.

Anderson, C., et al., 1998, Defination of MHC and T Cell receptor contact in the HLA-DR4-restricted immunodominant epitope in type II collagen and characterization of collagen-induced arthritis in HLA-DR4 and human CD4 transgenic mice, Proc. Natl. Acad. Sci. USA, Immunology, 95, pp. 7574-7579.

Buatois, V., et al., 2010, Pan-CC Chemokine Neutralization Restricts Splenocyte Egress and Reduces Inflammation in a Model of Arthritis, J. of Immun, 185: pp. 2544-2554.

Chung, S., et al., 2010, Research Article, CXC Chemokine receptor 4 expressed in T cells plays an important role in the development of collagen-induced arthritis, Arthritis Res Ther, 12: R188.

Gonzalo, J., et al., 2000 Critical Involvement of the Chemotactic Axis CXCR4/Stromal Cell Derived Factor 1α in the Inflammatory Component of Allergic Airway Disease, The Journal of Immunology, 165, pp. 499-508.

Nanki, T., et al., 2000, Factor-1 is a costimulator for CD4+ T Cell activation, The Journal of Immunology, 164, pp. 5010-5014.

Winter, C., et al., 1962, Carrageenin-Induced Edema in Hind Paw of the rat as an assay for antiinflammatory Drugs, Soc. Exp. Biol. 111, pp. 544-547.

Xu, J., et al., 2007, Role of the SDF-1/CXCR4 Axis in the Pathogenesis of Lung Injury and Fibrosis, Amer. J. Resp. Cell Mol. Biol., 37, pp. 291-299.

Yssel, H., et al. 1998, The Role of IgE in Asthma, Clinical and Experimental Allergy, 28,pp. 104-109.

Zhu, A, et al, Dipyrimidine Amines: A Novel Class of Chemokine Receptor Type 4 Antagonist with High Specificity, J of Medicinal Chemistry, 2010, 53; pp. 8556-8568.

\* cited by examiner

WZZL811S

CXCR4 ANTAGONISTS FOR THE TREATMENT OF MEDICAL DISORDERS

CROSS-REFERENCE TO RELATED APPLICATIONS

This application claims priority to U.S. Provisional Application No. 60/642,375, filed Jan. 7, 2005, U.S. Provisional Application No. 60/642,374, filed Jan. 7, 2005 and U.S. Provisional Application No. 60/682,655, filed May 18, 2005 now abandoned.

FIELD OF THE INVENTION

The invention provides compounds, pharmaceutical compositions and methods of use of certain compounds that are antagonists of the chemokine CXCR4 receptor. The compounds are useful to mediate any medical condition that is modulated by CXCR4 receptor signaling, and in particular for treating or reducing the severity of hyperproliferative diseases by inhibiting metastasis.

BACKGROUND

Cancer is currently the second leading cause of death in developed nations. In 2004, the American Cancer Society estimated that approximately 1.37 million new cases were diagnosed in the U.S. alone, and approximately 550,000 deaths occurred due to cancer (American Cancer Society, Cancer Facts & Figures 2004, see URL: http://www.cancer.org/docroot/STT/stt_0.asp).

Metastasis, the spread and growth of tumor cells to distant organs, is the most devastating attribute of cancer. Most morbidity and mortality associated with certain types of cancer, such as breast cancer, is associated with disease caused by metastatic cells rather than by the primary tumor. Therapy for metastasis currently relies on a combination of early diagnosis and aggressive treatment of the primary tumor.

The establishment and growth of metastases at distant sites is thought to depend on interactions between tumor cells and the host environment. Metastasis is the result of several sequential steps and represents a highly organized, non-random and organ-selective process. Although a number of mediators have been implicated in the metastasis of breast cancer, the precise mechanisms determining the directional migration and invasion of tumor cells into specific organs remain to be established. An incomplete understanding of the molecular and cellular mechanisms underlying metastasis has hindered the development of effective therapies that would eliminate or ameliorate this condition.

Several strategies have been developed to reduce metastatic invasion of malignant cells by regulating adhesion of endothelial cells with antibodies or adhesion molecules (see for example, PCT Publication No. WO 97/00956, U.S. Pat. Nos. 5,993,817; 6,433,149; 6,475,488; and 6,358,915). However no commercial strategy has provided an effective treatment to prevent metastasis:

Chemokines are a superfamily of small cytokines that induce, through their interaction with G-protein-coupled receptors, cytoskeletal rearrangements and directional migration of several cell types (Butcher, et al. (1999) *Adv Immunol* 72: 209-253; Campbell and Butcher (2000) *Curr Opin Immunol* 12: 336-341; Zlotnik and Yoshie (2000) *Immunity* 12: 121-127). These secreted proteins act in a coordinated fashion with cell-surface proteins to direct the homing of various subsets of cells to specific anatomical sites (Motales, et al. (1999) *Proc Natl Acad Sci USA* 96: 14470-14475; Homey, B., et al. (2000) *J Immunol* 164: 3465-3470; Peled, et al. (1999) *Science* 283: 845-848; Forster, et al. (1999) *Cell* 99: 23-33).

Chemokines are considered to be principal mediators in the initiation and maintenance of inflammation. They have also been found to play an important role in the regulation of endothelial cell function, including proliferation, migration and differentiation during angiogenesis and re-endothelialization after injury (Gupta et al. (1998) *J Biol Chem,* 7:4282-4287). Two specific chemokines have also been implicated in the etiology of infection by human immunodeficiency virus (HIV).

The chemokine receptor, CXCR4, is known in viral research as a major coreceptor for the entry of T cell linetropic HIV (Feng, et al. (1996) *Science* 272: 872-877; Davis, et al. (1997) *J Exp Med* 186: 1793-1798; Zaitseva, et al. (1997) *Nat Med* 3: 1369-1375; Sanchez, et al. (1997) *J Biol Chem* 272: 27529-27531). T Stromal cell derived factor 1 (SDF-1) is a chemokine that interacts specifically with CXCR4. When SDF-1 binds to CXCR4, CXCR4 activates $G\alpha_i$-protein-mediated signaling (pertussis toxin-sensitive) (Chen, et al. (1998) *Mol Pharmacol* 53: 177-181), including downstream kinase pathways such as Ras/MAP Kinases and phosphatidylinositol 3-kinase (PI3K)/Akt in lymphocyte, megakaryocytes, and hematopoietic stem cells (Bleul, et al. (1996) *Nature* 382: 829-833; Deng, et al. (1997) *Nature* 388: 296-300; Kijowski, et al. (2001) *Stem Cells* 19: 453-466; Majka, et al. (2001) *Folia. Histochem. Cytobiol.* 39: 235-244; Sotsios, et al. (1999) *J. Immunol.* 163: 5954-5963; Vlahakis, et al. (2002) *J. Immunol.* 169: 5546-5554). In mice transplanted with human lymph nodes, SDF-1 induces CXCR4-positive cell migration into the transplanted lymph node (Blades, et al. (2002) *J. Immunol.* 168: 4308-4317). These results imply that the interaction between SDF-1 and CXCR4 directs cells to the organ sites with high levels of SDF-1.

Recently, studies have shown that CXCR4 interactions may regulate the migration of metastatic cells. Hypoxia, a reduction in partial oxygen pressure, is a microenvironmental change that occurs in most solid tumors and is a major inducer of tumor angiogenesis and therapeutic resistance. Hypoxia increases CXCR4 levels (Staller, et al. (2003) *Nature* 425: 307-311). Microarray analysis on a sub-population of cells from a bone metastatic model with elevated metastatic activity showed that one of the genes increased in the metastatic phenotype was CXCR4. Furthermore, overexpression CXCR4 in isolated cells significantly increased the metastatic activity (Kang, et al. (2003) *Cancer Cell* 3: 537-549). In samples collected from various breast cancer patients, Muller et al. (Muller, et al. (2001) *Nature* 410: 50-56) found that CXCR4 expression level is higher in primary tumors relative to normal mammary gland or epithelial cells. These results suggest that the expression of CXCR4 on cancer cell surfaces may direct the cancer cells to sites that express high levels of SDF-1. Consistent with this hypothesis, SDF-1 is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs (Muller, et al. (2001)).

In addition to regulating migration of cancer cells, CXCR4-SDF-1 interactions may regulate vascularization necessary for metastasis. Blocking either CXCR4/SDF-1 interaction or the major G-protein of CXCR4/SDF-1 signaling pathway ($G\alpha_i$) inhibits VEGF-dependent neovascularization. These results indicate that SDF-1/CXCR4 controls VEGF signaling systems that are regulators of endothelial cell morphogenesis and angiogenesis. Numerous studies have shown that VEGF and MMPs actively contribute to cancer progression and metastasis.

Several groups have identified chemokines including CXCR4 as a target for treatment of metastatic cancers. For example, PCT Publication Nos. WO 01/38352 to Schering Corporation, WO 04/059285 to Protein Design Labs, Inc., and WO 04/024178 to Burger generally describe methods of treating diseases and specifically inhibiting metastasis by blocking chemokine receptor signaling.

Compounds targeting CXCR4 have been developed primarily for treatment of HIV because CXCR4 is a major coreceptor for T-tropic HIV infection. For example, U.S. Pat. No: 6,429,308 to Hisamitsu Pharmaceutical Co., Inc. discloses an antisense oligonucleotide that inhibits the expression of the CXCR4 protein for use as an anti-HIV agent. PCT Publication No. WO 01/56591 to Thomas Jefferson University describes peptide fragments of viral macrophage inflammatory protein II which are described as selectively preventing CXCR4 signal transduction and coreceptor function in mediating entry of HIV-1.

Peptide antagonists of CXCR4 receptors have been disclosed. Tamamura et al (Tamamura, et al. (2000) *Bioorg. Med. Chem. Lett.* 10: 2633-2637; Tamamura, et al. (2001) *Bioorg. Med. Chem. Lett.* 11: 1897-1902) reported the identification of a specific peptide-based CXCR4 inhibitor, T140. T140 is a 14-residue peptide that possesses anti-HIV activity and antagonism of T cell line-tropic HIV-1 entry among all antagonists of CXCR4 (Tamamura, et al. (1998) *Biochem. Biophys. Res. Commun.* 253: 877-882). The compound was altered to increase its efficacy and bioavailability by, for example, amidating the C-terminal of T-140 and reducing the total positive charges by substituting basic residues with non-basic polar amino acids to generate TN14003, which is less cytotoxic and more stable in serum compared to T140. The concentration of TN14003 required for 50% protection of HIV-induced cytopathogenicity in MT-4 cells is 0.6 nM in contrast to 410 μM leading to 50% toxicity. PCT Publication No. WO 04/087068 to Emory University describes CXCR4 peptide antagonists, particularly TN14003, and methods of their use to treat metastasis.

Other peptide-based antagonists have also been disclosed. For example, European Patent Publication Nos. 1 286 684 and 1 061 944 to the University Of British Columbia cover methods of treatment of diseases, including metastasis, using modified peptide CXCR4 antagonists derived from the native SDF-1 ligand. PCT Publication No. WO 04/020462 to Takeda Chemical Industries, Ltd. provides peptide CXCR4 antagonists for treatment and prevention of breast cancer and chronic rheumatoid arthritis. U.S. Patent Application No. 2004/0132642 to the U.S. Dept. of Health & Human Services in part covers methods of inhibiting metastasis or growth of a tumor cell with a polypeptide CXCR4 inhibitor.

Although advances have been made, inadequate absorption, distribution, metabolism, excretion or toxicity properties of peptide inhibitors have limited their clinical uses. Small non-peptide drugs remain as a major goal of medicinal chemistry programs in this area.

At the present time, the metal-chelating cyclams and bicyclams represent one of the few reported non-peptide molecules to effectively block CXCR4 (Onuffer and Horuk (2002) *Trends Pharmacol Sci* 23: 459-467.36). One of these non-peptide molecules is AMD3100, which entered clinical trials as an anti-HIV drug that blocks CXCR4-mediated viral entry (Donzella, et al. (1998) *Nat Med* 4: 72-77; Hatse, et al. (2002) *FEBS Lett* 527: 255-262; Fujii, et al. (2003) *Expert Opin Investig Drugs* 12: 185-195; Schols, et al. (1997) *Antiviral Res* 35: 147-156).

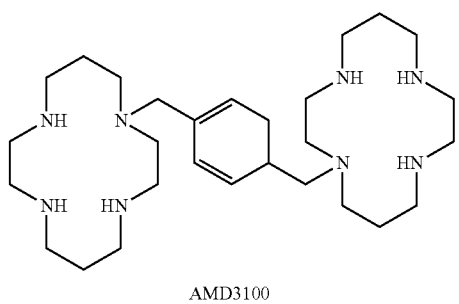

AMD3100

It has not been reported whether AMD3100 can efficiently block breast cancer metastasis, modulated via CXCR4. More importantly, a clinical study showed cardiac-related side effect of AMD3100 (Scozzafava, et al. (2002) *J Enzyme Inhib Med Chem* 17: 69-7641). In fact, AMD3100, was recently withdrawn from the clinical trials due in part to a cardiac-related side effect (Hendrix, et al. (2004) *Journal of Acquired Immune Deficiency Syndromes* 37(2)). The latter was not a result of the compound's ability to block CXCR4 function, but due to its presumed structural capacity for encapsulating metals.

Other nitrogen containing bicyclic molecules have been developed as CXCR4 antagonists. European Patent Publication No. 1 431 290 and PCT Publication No. WO 02/094261 to Kureha Chemical Industry Co., Ltd cover CXCR4 inhibitors that are potentially useful in treating various diseases including cancer metastatic disease.

U.S. Patent Publication No. 2004/0254221 to Yamamazi, et al. also provides compounds and use thereof to treat various diseases including cancer metastasis that are CXCR4 antagonists. The compounds are of the general formula:

$$A-(CH_2)_{n1}-W-x-\underset{\underset{B}{|}}{\underset{(CH_2)_{n2}}{\overset{|}{CH}}}-y-N\overset{D_1}{\underset{D_2}{\diagdown}}$$

in which A is $A_1$-$G_1$-N($R_1$)—; $A_1$ is hydrogen or an optionally substituted, mono- or polycyclic, heteroaromatic or aromatic ring; $G_1$ is a single bond or —C($R_2$)($R_3$)—; $R_1$, $R_2$, and $R_3$ can be optionally substituted hydrocarbon groups; W is an optionally substituted hydrocarbon or heterocyclic ring; x is —(=O)NH—; y is —(=O)—; and $D_1$ is hydrogen atom, alkyl with a polycyclic aromatic ring, or amine.

PCT Publication No. WO 00/56729 and U.S. Pat. No. 6,750,348 to AnorMED and describe certain heterocyclic small molecule CXCR4 binding compounds, teaching that these are useful for the treatment of HIV infection, tumerogenesis, psoriasis or allergy. The compounds are of the general formula:

in which W can be a nitrogen or carbon atom; Y is absent or is hydrogen; $R^1$ to $R^7$ can be hydrogen or straight, branched or cyclic $C_{1-6}$ alkyl; $R^8$ is a substituted heterocyclic or aromatic group; Ar is an aromatic or heteroaromatic ring; and X is specified ring structure.

PCT Publication No. WO 2004/091518 to AnorMED also describes certain substituted nitrogen containing compounds that bind to CXCR4 receptors. The compounds are described as having the effect of increasing progenitor cells and/or stem cells; enhancing production of white blood cells, and exhibiting antiviral properties. PCT Publication No. WO 2004/093817 to AnorMED also discloses substituted heterocyclic CXCR4 antagonists which are described as useful to alleviate inflammatory conditions and elevate progenitor cells, as well as white blood cell counts. Similarly, PCT Publication No. WO 2004/106493 to AnorMED describes heterocyclic compounds that bind to CXCR4 and CCR5 receptors consisting of a core nitrogen atom surrounded by three pendant groups, wherein two of the three pendant groups are preferably benzimidazolyl methyl and tetrahydroquinolyl, and the third pendant group contains nitrogen and optionally contains additional rings. The compounds demonstrate protective effects against infections of target cells by a human immunodeficiency virus (HIV).

In light of the fact that the CXCR4 receptor is implicated in metastatic signaling as well as a number of other pathogenic conditions, it is important to identify new effective receptor antagonists.

It is therefore an object of the invention to provide new compounds, methods and compositions that inhibit CXCR4 receptor signaling.

It is another object of the invention to provide compounds, methods and compositions that bind to the CXCR4 receptor and interfere with binding to its native ligand.

It is a more specific object of the invention to provide compound, methods and compositions for treatment of proliferative disorders, and in particular, for the inhibition of cancer metastases.

SUMMARY

Compounds, methods and pharmaceutical compositions for the treatment or prevention of diseases associated with pathogenic or undesired CXCR4 receptor activity and/or signaling are provided. In particular, it is believed that the compounds provided herein interfere with the binding of the native SDF-1 ligand to the CXCR4 receptor and inhibit activation of the receptor and subsequent downstream signaling pathways. Based on this pathway, the invention provides compounds, methods and pharmaceutical compositions for the treatment of pathogenic conditions, including hyperproliferative diseases, and particularly for the reduction of cell migration and differentiation associated with cancer metastasis, modulated via CXCR4. The compounds, methods and compositions include an effective treatment amount of a compound of Formulas (I)-(XVII), or a pharmaceutically acceptable salt, ester or prodrug thereof.

In a first principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula I, or a pharmaceutically acceptable salt, ester or prodrug thereof:

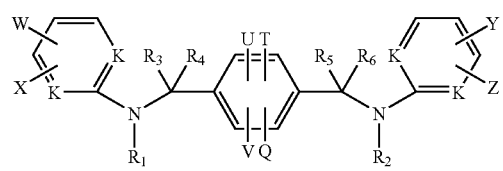

Formula I wherein
each K is independently N or CH;
Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl groups, as well as aryl and heteroaryl groups; and
$R_1$, $R_2$, $R_3$, $R_4$, $R_5$ and $R_6$ are independently selected from H, straight chain, branched or cyclic alkyl, aralkyl, aryl heteroaryl, acyl (RC—) and imidoyl (RC(NH)— or RC(NR')—) groups.

In another embodiment, the compound has the formula:

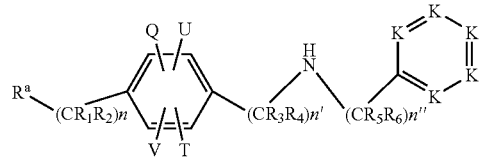

Ib wherein each K is independently N or CH;
Q, T, U, and V are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where each R and R' are independently selected from straight chain, branched or cyclic alkyl or aralkyl groups, as well as aryl and heteroaryl groups;
$R^a$ is independently selected from R, acyl, F, Cl, Br, I, OH, OR, $NH_2$, NHR, $NO_2$, $NR_2$, $SO_2$, SR, $S_2R$, S—NHR, $S_2$—NHR, S—NRR', $S_2$—NRR', NHacyl, $N(acyl)_2$, C(=O)R, $CO_2H$, $CO_2R$;
n, n' and n" are independently 0, 1, 2, 3, 4, or 5; and
$R_1$, $R_2$, $R_3$, $R_4$, $R_5$ and $R_6$ are independently selected from H, straight chain, branched or cyclic alkyl, aralkyl, aryl heteroaryl, acyl (RC—) and imidoyl (RC(NH)— or RC(NR')—) groups.

In another embodiment, the compound has the formula:

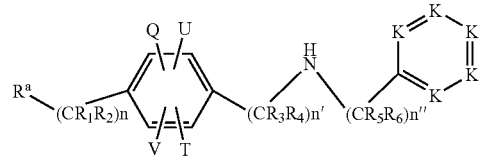

Ia each K is independently N or CH;
Q, T, U, and V are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where each R and R' are independently selected from straight chain, branched or cyclic alkyl or aralkyl groups, as well as aryl and heteroaryl groups;

$R^a$, n, n' and n" and $R_1$, $R_2$, $R_3$, $R_4$, $R_5$ and $R_6$ are as defined above.

In a second principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula IIa or IIb, or a pharmaceutically acceptable salt, ester or prodrug thereof:

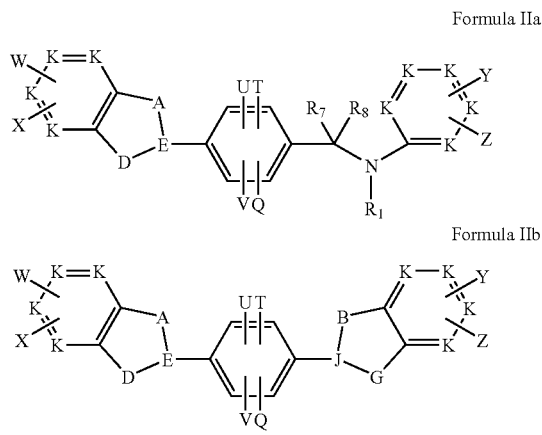

Formula IIa

Formula IIb wherein
each K is independently N or CH;
Q, T, U, V, W, X, Y and Z are as defined above;
A and B are one and two atom tethers independently selected from —CR═, —CR$_3$R$_4$—, —CR$_3$═, —N═, —O—, —NR$_3$—, —S—, —CR$_3$═CR$_4$—, —CR$_3$R$_4$—CR$_5$R$_6$—, —CR$_3$═N—, —CR$_0$R$_4$—NR$_5$—, —N═CR$_3$—, and —NR$_3$—CR$_4$R$_5$—;
R and R' are as defined above;
-D-E- and -G-J- are independently either —NR$_3$—CR$_4$— or —N═C—; and
$R_1$, $R_2$, $R_3$, $R_4$, $R_5$, $R_6$, $R_7$ and $R_8$ are independently selected from H, straight chain, branched or cyclic alkyl, aralkyl, aryl heteroaryl, acyl (RC—) and imidoyl (RC(NH)— or RC(NR')—) groups.

In a third principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula III, or a pharmaceutically acceptable salt, ester or prodrug thereof:

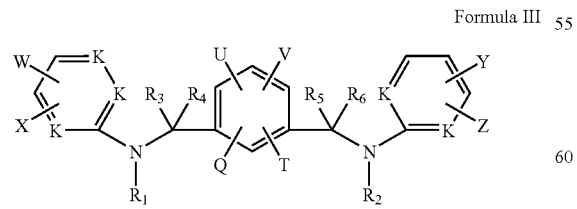

Formula III wherein
each K is independently N or CH;
Q, T, U, V, W, X, Y and Z are as defined above; and
R, R', $R_1$, $R_2$, $R_3$, $R_4$, $R_5$ and $R_6$ are as defined above.

In a fourth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula IVa or IVb, or a pharmaceutically acceptable salt, ester or prodrug thereof:

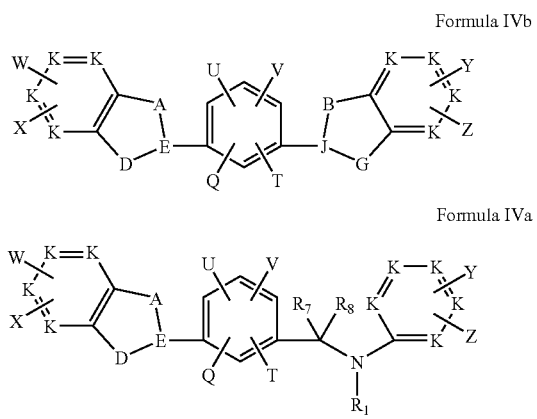

Formula IVb

Formula IVa wherein
each K is independently N or CH;
Q, T, U, V, W, X, Y and Z are as defined above;
R, R', $R_1$, $R_2$, $R_3$, $R_4$, $R_5$, $R_6$, $R_7$ and $R_8$ are as defined above; and
A and B and -D-E- and -G-J- are as defined above.

In a fifth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula Va, Vb or Vc, or a pharmaceutically acceptable salt, ester or prodrug thereof:

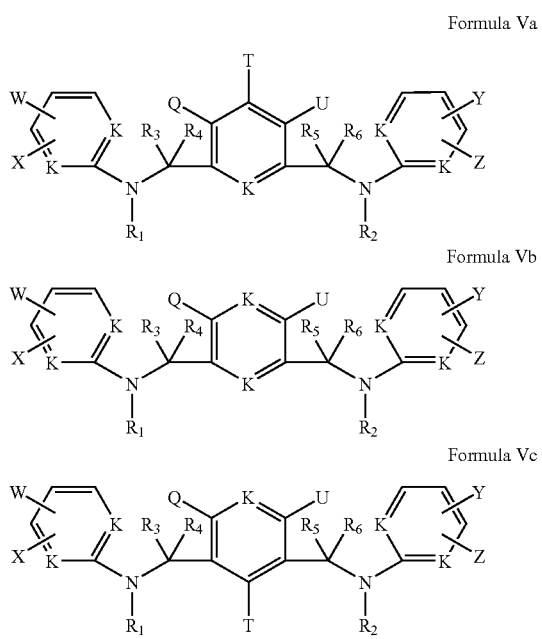

Formula Va

Formula Vb

Formula Vc wherein
each K is independently N or CH;
Q, T, U, W, X, Y and Z are as defined above; and
R, R', $R_1$, $R_2$, $R_3$, $R_4$, $R_5$ and $R_6$ are as defined above.

In a sixth principal embodiment, a method, compound and pharmaceutical composition for the treatment or prevention of a disorder associated with CXCR4 receptor activation, and particularly a proliferative disorder, including cancer metastasis, modulated via: CXCR4 is provided that includes a compound of Formula VIa or VIb, or a pharmaceutically acceptable salt, ester or prodrug thereof:

Formula VIa

Formula VIb wherein
each K is independently N or CH;
Q, T, U, W, X, Y and Z are as defined above;
R, R', $R_1$, $R_2$, $R_3$, $R_4$, $R_5$, $R_6$, $R_7$ and $R_8$ are as defined above; and
A and B and -D-E- and -G-J- are as defined above.

In a seventh principal embodiment, a method, compound and pharmaceutical composition for the treatment or prevention of a disorder associated with CXCR4 receptor activation, and particularly a proliferative disorder; including cancer metastasis, modulated via CXCR4 is provided that includes a compound of Formula VII, or a pharmaceutically acceptable salt, ester or prodrug thereof:

Formula VII wherein
each K is independently N or CH;
U, V, W, X, Y and Z are as defined above;
$R_1$, $R_2$, $R_3$; $R_4$, $R_5$ and $R_6$ are as defined above; and
M is O, S or $NR_3$.

In an eight principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula VIIIa or VIIIb, or a pharmaceutically acceptable salt, ester or prodrug thereof:

Formula VIIIa

Formula VIIIb wherein
each K is independently N or CH;
U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
M is O, S or $NR_3$.

In a ninth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula IX, or a pharmaceutically acceptable salt, ester or prodrug thereof:

Formula IX wherein
each K is independently N or CH;
W, X, Y and Z are as defined above;
$R_1$, $R_2$, $R_3$, $R_4$, $R_5$ and $R_6$ are as defined above;
A* is independently selected from the group consisting of formulas a-g:

(a)

(b)

(c)

(d)

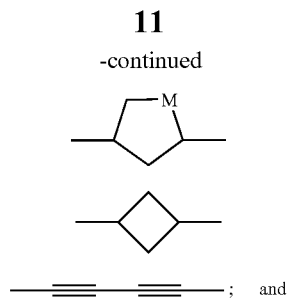

M is O, S or NR₃.

In a tenth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula X, or a pharmaceutically acceptable salt, ester or prodrug thereof:

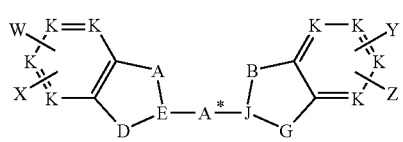

Formula X wherein
each K is independently N or CH;
W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
A* is as defined above; and
M is as defined above.

In an eleventh principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XI, or a pharmaceutically acceptable salt, ester or prodrug thereof:

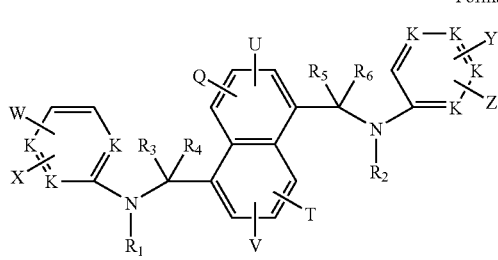

Formula XI wherein
each K is independently N or CH;
Q, T, U, V, W, X, Y and Z are as defined above; and
$R_1$, $R_2$, $R_3$, $R_4$, $R_5$ and $R_6$ are as defined above.

In a twelfth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XII, or a pharmaceutically acceptable salt, ester or prodrug thereof:

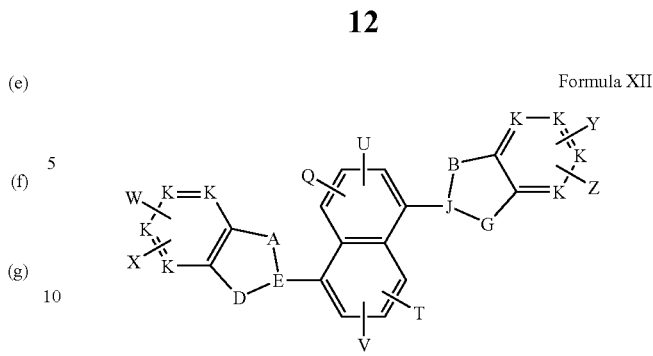

Formula XII wherein
each K is independently N or CH;
Q, T, U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In a thirteenth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XIII, or a pharmaceutically acceptable salt, ester or prodrug thereof:

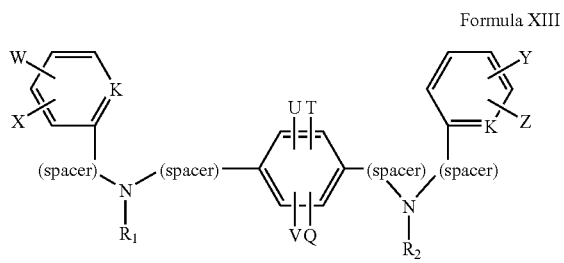

Formula XIII wherein
K, Q, T, U, V, W, X, Y and Z are as defined above;
$R_1$, $R_2$, $R_3$, $R_4$, $R_5$ and $R_6$ are as defined above; and
"spacer" is independently a bond, straight chained or branched $C_1$-$C_5$ alkyl, $C_2$-$C_5$ alkenyl, $C_2$-$C_5$ alkynyl, $C_1$-$C_5$ alkoxy, $C_2$-$C_5$ alkenoxy, and $C_2$-$C_5$ alkynoxy wherein the alkyl group can be substituted by a heteroatom (such as N, O or S), including but not limited to-$CH_2$—$OCH_2$—, —$CH_2CH_2$—$OCH_2$—, —$CH_2CH_2$—$OCH_2CH_2$—, —$CH_2$—$OCH_2CH_2$—, —$CH_2CH_2$—$OCH_2CH_2CH_2$—, —$CH_2CH_2CH_2$—$OCH_2$—, —$CH_2CH_2CH_2$—$OCH_2CH_2$—, —$CH_2CH_2$—$OCH_2CH_2CH_2$—, —$(CH_2)_n$—$OH(CH_3)$—$(CH_2)_n$—, $CH_2$—$OH(CH_3)$—O—$CH_2$, —$(CH_2)$n-, —$(CH_2)$n-CO—, —$(CH_2)$n-N—, —$(CH_2)$n-O—, —$(CH_2)$n-S—, —$(CH_2O)$—, —$(OCH_2)$—, —$(SCH_2)$—, —$(CH_2S$—), -(aryl-O)—, —(O-aryl)-, -(alkyl-O)—, —(O-alkyl)- wherein n is independently 0, 1, 2, 3, 4, 5, 6, 7, 8, 9, or 10.

In a fourteenth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XIVa or XIVb, or a pharmaceutically acceptable salt, ester or prodrug thereof:

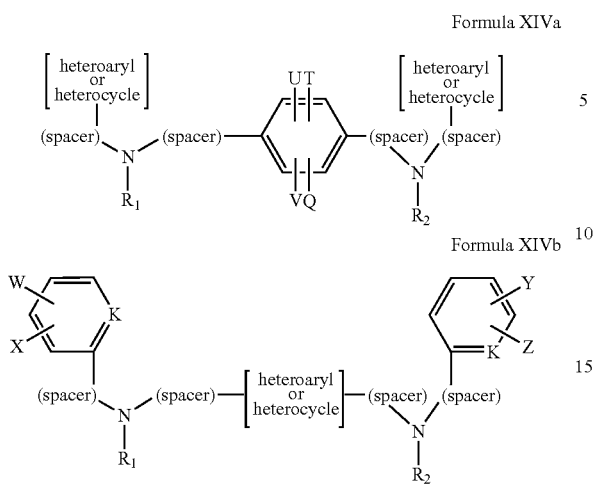

Formula XIVa

Formula XIVb wherein
K, Q, T, U, V, W, X, Y and Z are as defined above;
$R_1$, $R_2$, $R_3$, $R_4$, $R_5$ and $R_6$ are as defined above;
"spacer" is as defined above; and
"heterocycle" and "heteroaromatic" are as defined herein.

The compounds of the invention are particularly useful for inhibiting CXCR4 receptor interactions with native ligands. In one embodiment, a method is provided to inhibit CXCR4-mediated disorders by contacting a cell with a compound of Formula (I)-(XVII). The compounds described above, are particularly useful for the treatment or prevention of a disorder associated with CXCR4 receptor activation, and particularly a proliferative disorder, including cancer metastasis, modulated via CXCR4.

In one embodiment, a method of preventing metastases of a malignant cell is provided that includes administering a compound of Formula (I)-(XVII) to a host. The malignant cell can be a tumor cell. In certain embodiments, the compound can be provided to a host before treatment of a tumor with a second active compound. In a separate embodiment, the compound is provided to a patient that has been treated for cancer to reduce the likelihood of recurrence, or reduce mortality associated with a particular tumor. The compound of Formula (I)-(XVII) can also be provided in conjunction with another active compound.

In one particular embodiment, a method of preventing metastasis of a malignant cell is provided that includes contacting the cells with a compound of Formula XV, or a pharmaceutically acceptable salt, ester or prodrug thereof:

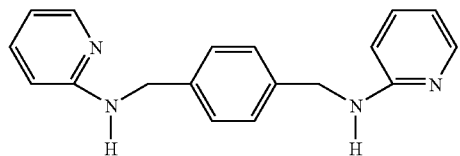

Formula XV

In a particular subembodiment, the compound is a salt of a compound of Formula XV, particularly a chloride salt.

In another particular embodiment, a method of preventing metastasis of a malignant cell is provided that includes contacting the cells with a compound of Formula XVI, or a pharmaceutically acceptable salt, ester or prodrug thereof:

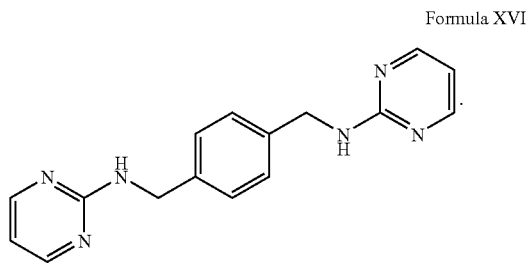

Formula XVI

In another particular embodiment, a method of preventing metastasis of a malignant cell is provided that includes contacting the cells with a compound of Formula XVII, or a pharmaceutically acceptable salt, ester or prodrug thereof:

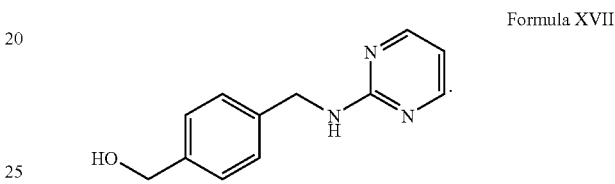

Formula XVII

In a separate embodiment, a method of treating disorders mediated by CXCR4, including metastasis, by administering a compound of Formulas (I)-(XVII) to a host in need of treatment is provided. In certain embodiments, the proliferative disorder is cancer, and in particular subembodiments, the disorder is a metastatic cancer. The compounds of the invention can be administered to a host in need thereof to reduce the incidence of metastasis. In particular embodiments, the disease is breast, brain, pancreatic, ovarian, particularly an ovarian epithelial, prostate, kidney, or non-small cell lung cancer. In a subembodiment, the compound is administered in combination or alternation with another active compound.

In another embodiment, the invention provides a method of reducing neovascularization, particularly VEGF-dependent neocascularization, by contacting a cell with a compound described herein. The cell can be in a host animal, including a human.

In another embodiment, pharmaceutical compositions including at least one compound of Formulas (I)-(XVII) are provided. In certain embodiments, at least a second active compound is included in the composition. The second active compound can be a chemotherapeutic, particularly an agent active against a primary tumor.

In one embodiment, a compound of Formula (I)-(XVII) is used to stimulate the production, proliferation and isolation of stem cells and progenitor cells bearing a CXCR4 receptors. Such cells include but are not limited to bone marrow progenitor and/or stem cells or progenitor cells for cardiac tissue.

In a separate embodiment, a method for treating diseases of vasculature, inflammatory and degenerative diseases is provided including administering a compound of Formula (I)-(XVII) to a host.

In a separate embodiment, a process for screening potential drug candidates is provided. The process includes providing a labeled peptide-based CXCR4 antagonist that has a detectable signal when bound to a CXCR4 receptor; contacting a CXCR4 receptor with at least one test molecule at a known concentration to form a test sample; contacting the test sample with the peptide-based antagonist; separately, contacting the peptide-based antagonist to a sample not including any test molecule to form a control sample; and comparing the signal from the test sample to the signal from the control sample. In a specific sub-embodiment, the peptide-based antagonist is derived from TN14003 (described in PCT Publication No. WO 04/087068 to Emory University). In a further subembodiment, the antagonist is labeled with a biotin molecule and the signal is elicited when the biotin-labeled antagonist is contacted with a streptavadin-conjugated signal molecule.

DETAILED DESCRIPTION OF THE INVENTION

Figure 1:
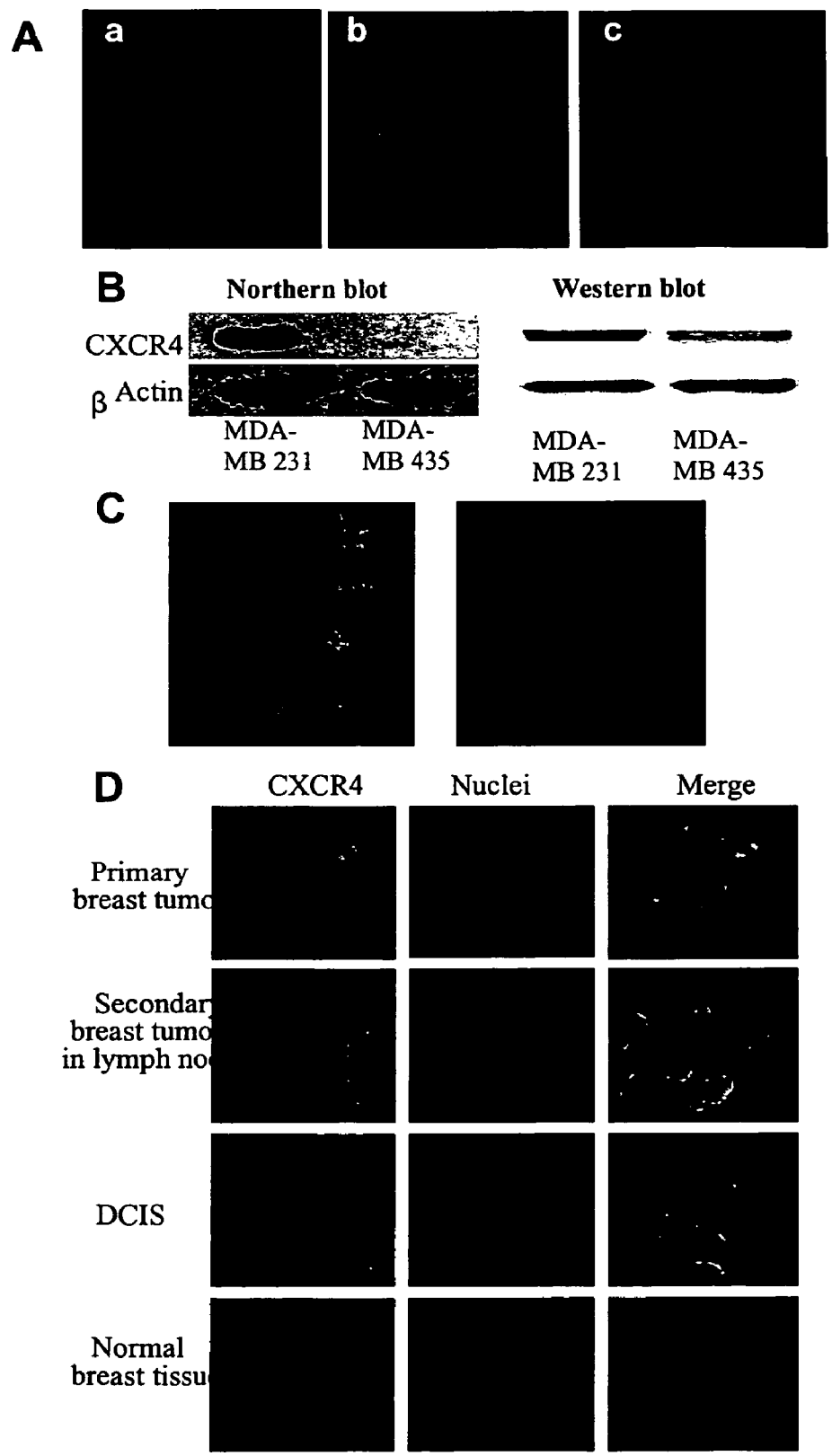
FIG. 1 shows images of stained cells and blots indicating the specificity of TN14003. A: The binding of TN14003 to CXCR4 was blocked by preincubation of 400 ng/ml SDF-1. Cells were immunostained by using biotin-labeled control peptide (a) or biotin-labeled TN14003 (b & c) and streptavidin-conjugated rhodamine (red). Cells were preincubated with SDF-1 for 10 min and then fixed in ice-cold acetone (c). B: Northern blot analysis and western blot analysis results show the different expression levels of CXCR4 from breast cancer cell lines, MDA-MB-231 and MDA-MB-435. β-actin was used as a loading control for both. C: Confocal micrographs of CXCR4 protein on cell's surface from MDA-MB-231 and MDA-MB-435 cell lines by using biotinylated TN14003 and streptavidin-conjugated R-PE (red color). Nuclei were counter-stained by cytox blue. D: Representative immunofluorescence staining of CXCR4 with the biotinylated TN14003 on paraffin embedded tissue sections of breast cancer patients and normal breast tissue.

Compounds, methods and compositions are provided that modulate the effect of the CXCR4 receptor. These compounds can be used to treat tumor metastsis or any other disease, particularly hyperproliferative diseases, involving CXCR4.

Exemplary compounds of the invention were identified using structural comparisons the known CXCR4 antagonists AMD3100 (a metal-chelating bicyclam) and T140 (a peptide antagonist). Rhodopsin-based homology models of CXCR4 shows that AMD3100 is a weak partial agonist because it interacts with CXCR4/SDF-1 binding by two aspartic acids while the peptide-based CXCR4 antagonist, T140 (similar to TN14003) strongly binds the SDF-1 binding site of CXCR4 in extracellular domains and regions of the hydrophobic core proximal to the cell surface. This structural information was used to create a library of compounds with multiple nitrogens throughout the molecular framework, but structurally different from AMD3100. These compounds were screened for their capacity to compete with the peptide ligand, T140, for SDF-1 binding to CXCR4.

Compounds described herein have the capacity to interact with and potentially inhibit CXCR4 receptor activation. Exemplary compounds have increased bioavailability and efficacy in inhibiting CXCR4 receptors and SDF-1-dependent signaling over known CXCR4 antagonists. Although not to be bound by theory, these compounds may inhibit metastasis through their capacity to inhibit SDF-1-CXCR4 interactions, which can decrease cell targeting, and may also reduce VEGF-dependent endothelial cell morphogenesis and angiogenesis. This endothelial cell growth is a key event in metastases of tumors.

Active Compound, and Physiologically Acceptable Salts and Prodrugs Thereof

In a first principal embodiment, a compound of Formula I, or a pharmaceutically acceptable salt, ester or prodrug thereof, is provided for the treatment or prevention of a disorder associated with CXCR4 receptor activation, and particularly a proliferative disorder, including cancer metastasis, modulated via CXCR4 modulated via CXCR4:

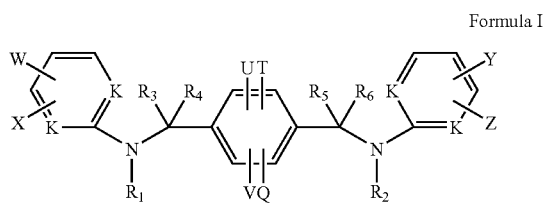

Formula I wherein each K is independently N or CH;

Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl groups, as well as aryl and heteroaryl groups; and $R_1$, $R_2$, $R_3$, $R_4$, $R_5$ and $R_6$ are independently selected from H, straight chain, branched or cyclic alkyl, aralkyl, aryl heteroaryl, acyl (RC—) and imidoyl (RC(NH)— or RC(NR')—) groups.

In one subembodiment of Formula I, Y and Z are each hydrogen. Alternatively, W and X are each hydrogen. In yet another subembodiment, W, X, Y and Z are all hydrogen.

Zou et al. (Zou, et al. (2003) *Acta Cryst.* E59: online 1312-o1313) described the synthesis of a potentially tetradentate ligand, 1,4-bis-(pyridine-2-aminomethyl)benzene. Zou described this compound as a potential ligand for metal ions. There is no suggestion in this reference that the compound could be used for treatment of any diseases, in particular for treatment of cancer metastasis, modulated via CXCR4.

In a subembodiment, a compound of Formula I-1 to I-10, or a pharmaceutically acceptable salt, ester or prodrug thereof, is provided for the treatment or prevention of a disorder associated with CXCR4 receptor activation, and particularly a proliferative disorder, including cancer metastasis, mediated by CXCR4:

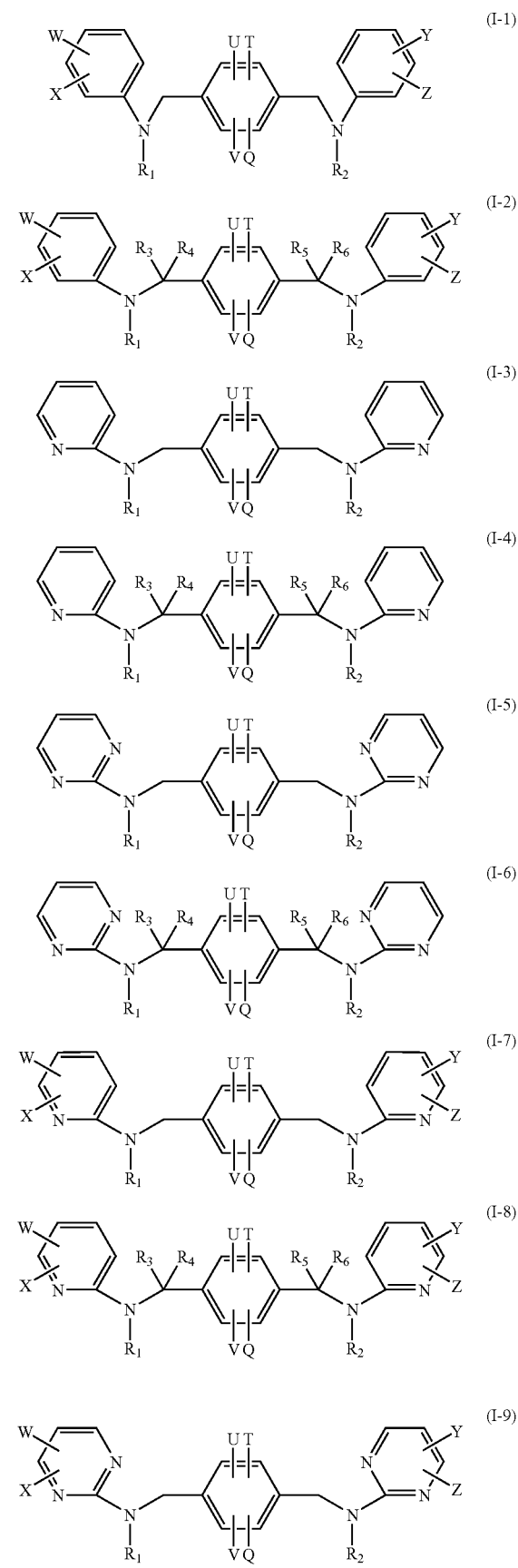

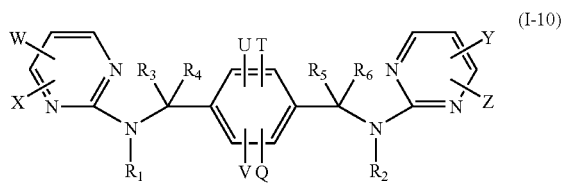

(I-10)

wherein

Q, T, U, V, W, X, Y and Z are as defined above; and $R_1, R_2, R_3, R_4, R_5$ and $R_6$ are as defined above.

In another sub-embodiment, a compound of Formula I-11 to I-20, or a pharmaceutically acceptable salt, ester or prodrug, is provided for the treatment or prevention of a disorder associated with CXCR4 receptor activation, and particularly a proliferative disorder, including cancer metastasis:

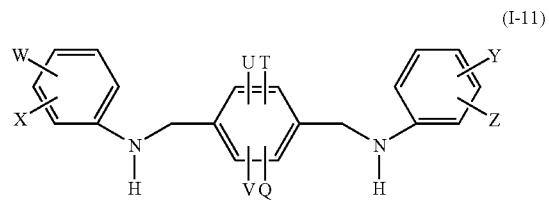

(I-11)

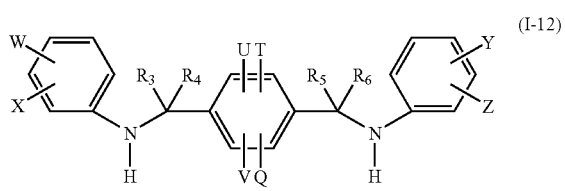

(I-12)

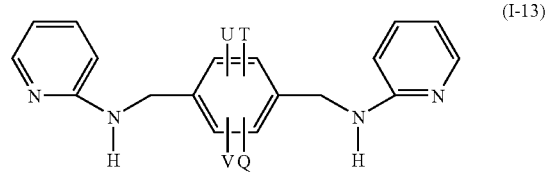

(I-13)

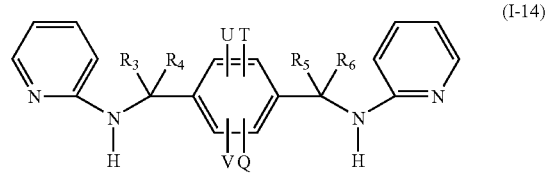

(I-14)

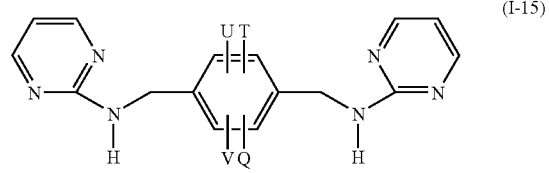

(I-15)

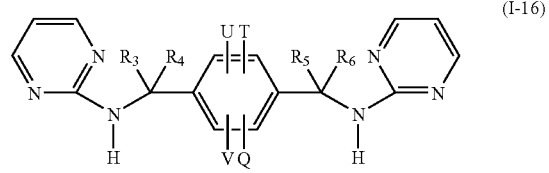

(I-16)

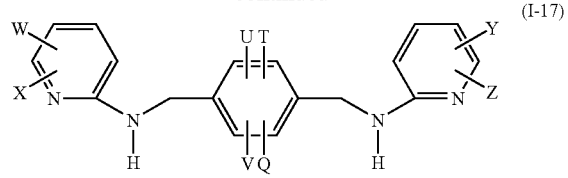

(I-17)

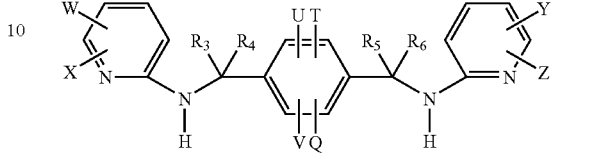

(I-18)

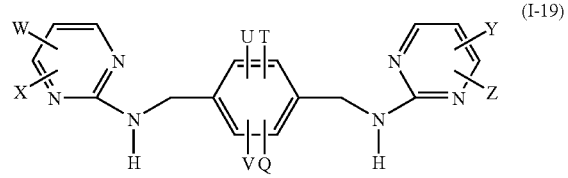

(I-19)

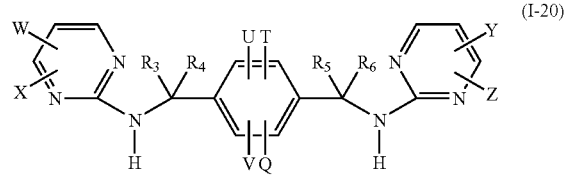

(I-20)

wherein

Q, T, U, V, W, X, Y and Z are as defined above; and $R_1, R_2, R_3, R_4, R_5$ and $R_6$ are as defined above.

In a second principal embodiment, the invention provides a compound of Formula IIa or IIb, or a pharmaceutically acceptable salt, ester or prodrug thereof:

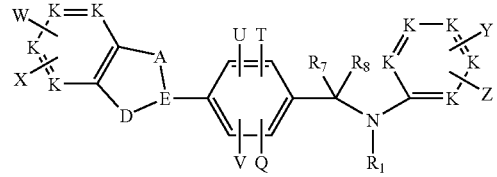

Formula IIa

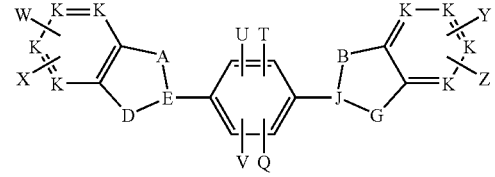

Formula IIb wherein each K is independently N or CH;

Q, T, U, V, W, X, Y and Z are as defined above;

A and B are one and two atom tethers independently selected from —CR=, —CR$_3$R$_4$—, —CR$_3$=, —N=, —O—, —NR$_3$—, —S—, —CR$_3$=CR$_4$—, —CR$_3$R$_4$—CR$_5$R$_6$—, —CR$_3$=N—, —CR$_3$R$_4$—NR$_5$—, —N=CR$_3$—, and —NR$_3$—CR$_4$R$_5$—;

-D-E- and -G-J- are independently either —NR$_3$—CR$_4$— or —N=C—; and $R_1$, $R_2$, $R_3$, $R_4$, $R_5$, $R_6$, $R_7$ and $R_8$ are independently selected from H, straight chain, branched or cyclic alkyl, aralkyl, aryl heteroaryl, acyl (RC—) and imidoyl (RC(NH)— or RC(NR')—) groups.

In one subembodiment of Formula II, Y and Z are each hydrogen. Alternatively, W and X are each hydrogen. In yet another subembodiment, W, X, Y and Z are all hydrogen.

In a subembodiment, the invention provides a compound of Formula I-1 to 1-18, or a pharmaceutically acceptable salt, ester or prodrug thereof:

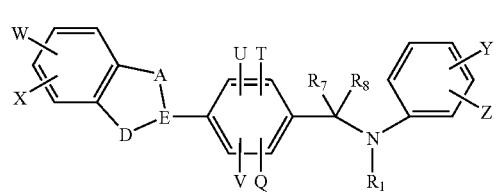
(II-1)

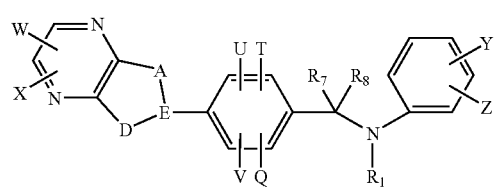
(II-2)

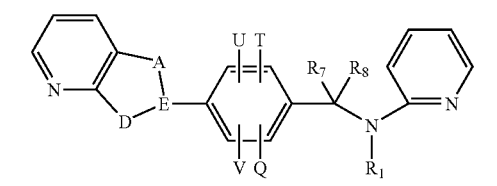
(II-3)

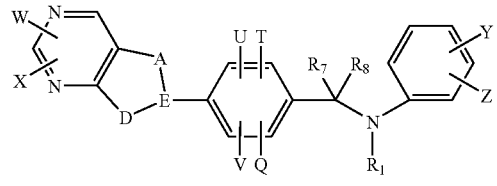
(II-4)

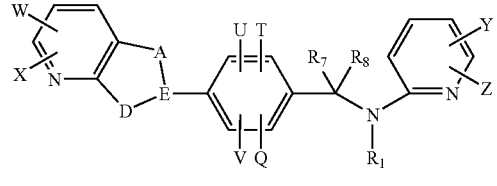
(II-5)

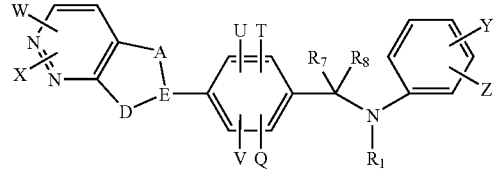
(II-6)

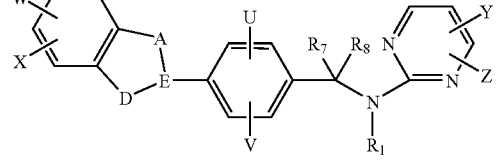
(II-7)

-continued

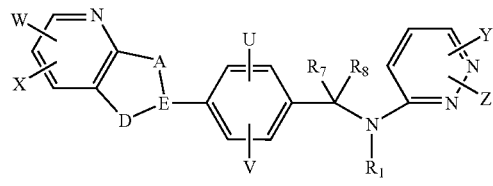
(II-8)

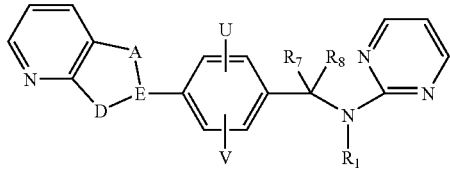
(II-9)

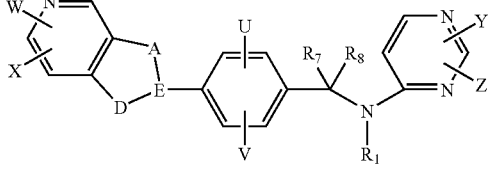
(II-10)

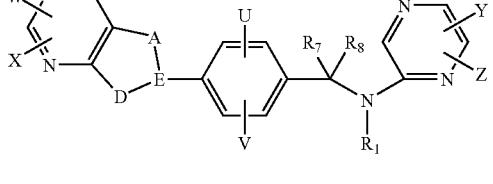
(II-11)

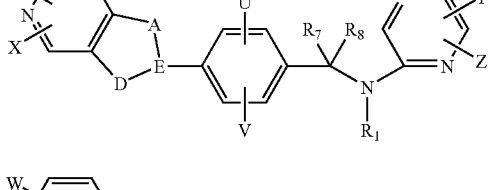
(II-12)

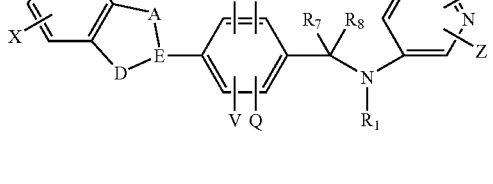
(II-13)

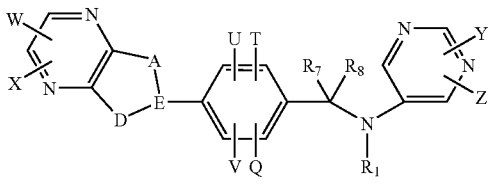
(II-14)

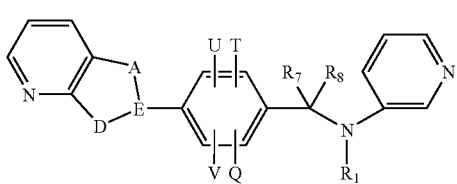
(II-15)

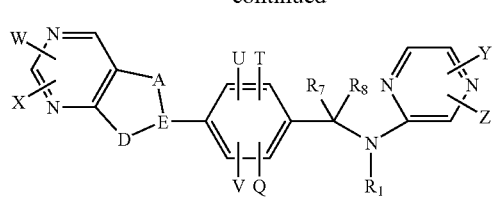
(II-16)
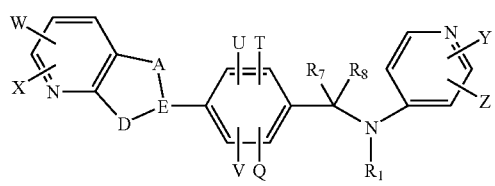
(II-17)
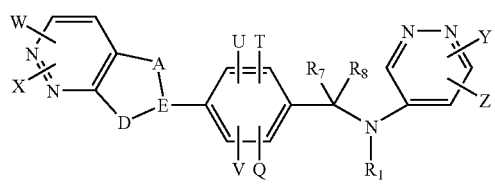
(II-18)
wherein
Q, T, U, V, W, X, Y and Z are as defined above;
A and -D-E- are as defined above; and
$R_1$, $R_2$, $R_3$, $R_4$, $R_5$, $R_6$, $R_7$ and $R_8$ are as defined above.
In another subembodiment, the invention provides a compound of Formula II-19 through II-30, or a pharmaceutically acceptable salt, ester or prodrug thereof:
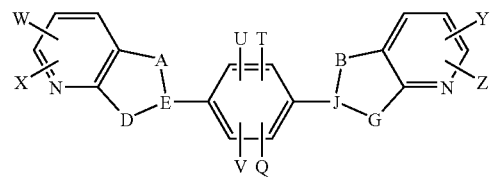
(II-19)
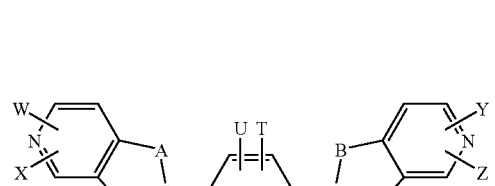
(II-20)
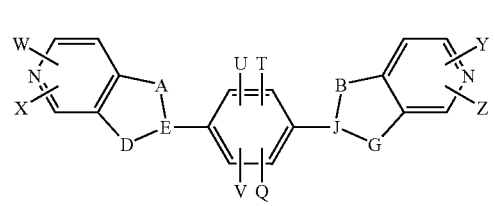
(II-21)
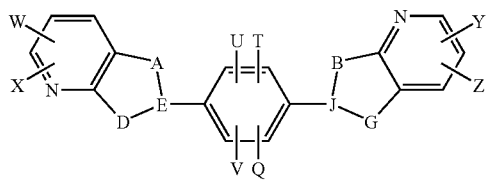
(II-22)
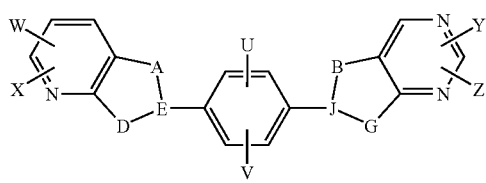
(II-23)
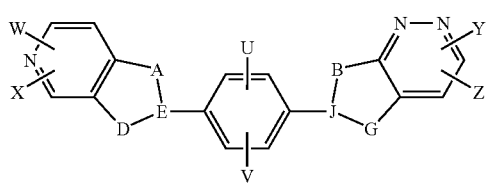
(II-24)
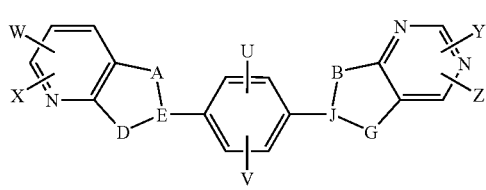
(II-25)
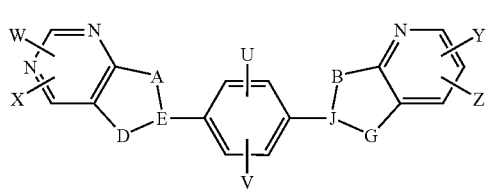
(II-26)
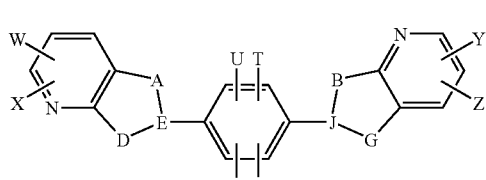
(II-27)
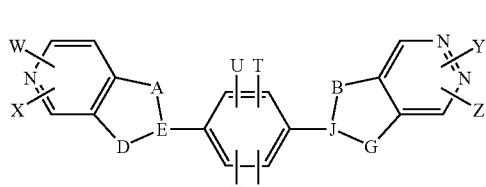
(II-28)
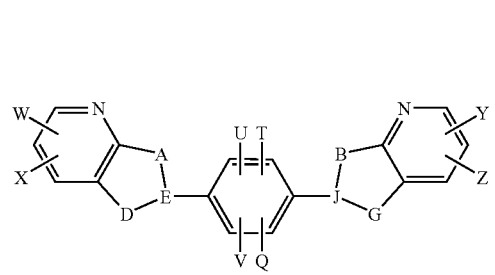
(II-29)

-continued (II-30)
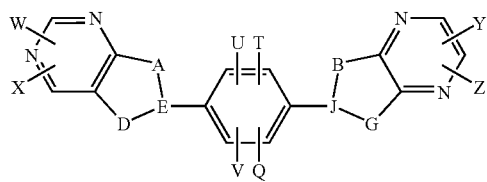

wherein
Q, T, U, V, W, X, Y and Z are as defined above;
A, B, -D-E- and -G-J- are as defined above; and
$R_1$, $R_2$, $R_3$, $R_4$, $R_5$, $R_6$, $R_7$ and $R_8$ are as defined above.

In an third principal embodiment, a compound of Formula III, or a pharmaceutically acceptable salt, ester or prodrug thereof, is provided for the treatment or prevention of a disorder associated with CXCR4 receptor activation, and particularly a proliferative disorder, including cancer metastasis:

Formula III
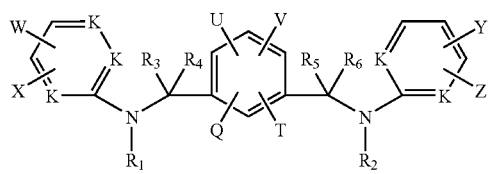

wherein
each K is independently N or CH;
Q, T, U, V, W, X, Y and Z are as defined above; and
$R_1$, $R_2$, $R_3$, $R_4$, $R_5$ and $R_6$ are as defined above.

In one subembodiment of Formula III, Y and Z are each hydrogen. Alternatively, W and X are each hydrogen. In yet another subembodiment, W, X, Y and Z are all hydrogen.

Reyes et al. (Reyes, et al. (2002) *Tetrahedron* 58:8573-8579) described the synthesis of certain polyamines from starting pyridinium N-aminides. No specific functions were attributed to these compounds.

In a subembodiment, a compound of Formula III-1 through III-10, or a pharmaceutically acceptable salt, ester or prodrug thereof, is provided for the treatment or prevention of a disorder associated with CXCR4 receptor activation, and particularly a proliferative disorder, including cancer metastasis:

(III-1)
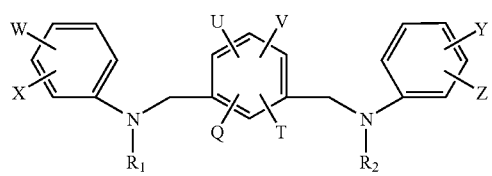

(III-2)
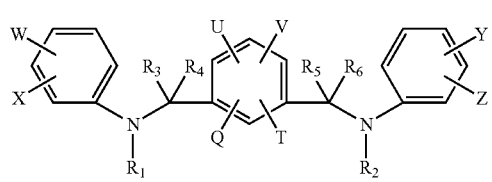

(III-3)
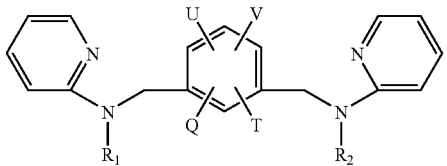

(III-4)
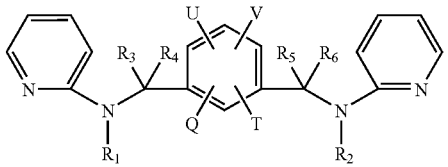

(III-5)
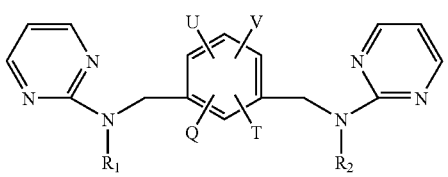

(III-6)
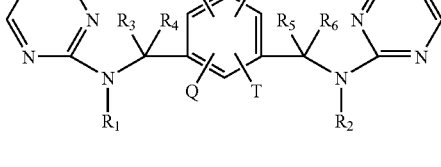

(III-7)
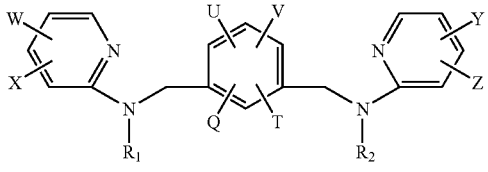

(III-8)
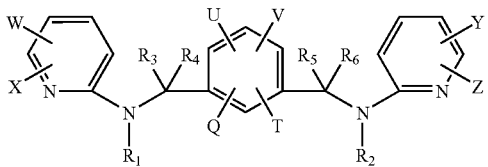

(III-9)
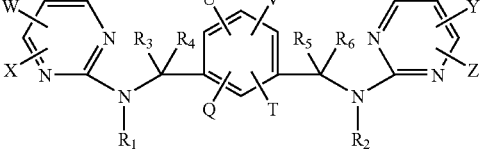

(III-10)
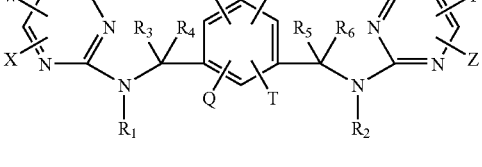

wherein
Q, T, U, V, W, X, Y and Z are as defined above; and
$R_1$, $R_2$, $R_3$, $R_4$, $R_5$ and $R_6$ are as defined above.

In another subembodiment, a compound of Formula III-11 through III-20, or a pharmaceutically acceptable salt, ester or prodrug thereof, is provided for the treatment or prevention of a disorder associated with CXCR4 receptor activation, and particularly a proliferative disorder, including cancer metastasis:

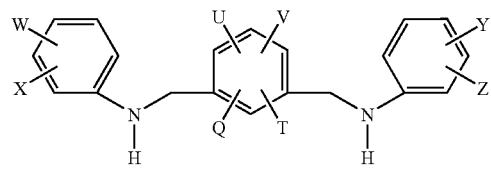
(III-11)

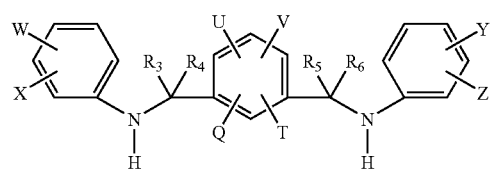
(III-12)

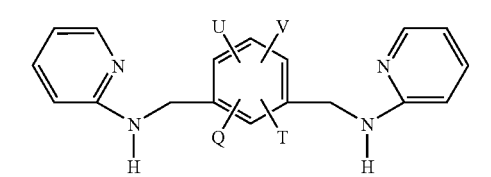
(III-13)

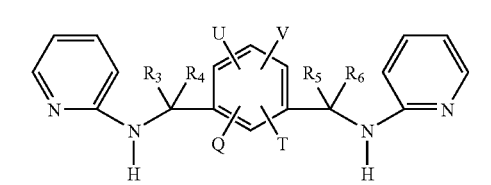
(III-14)

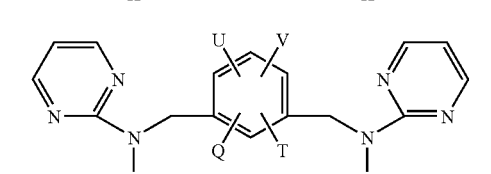
(III-15)

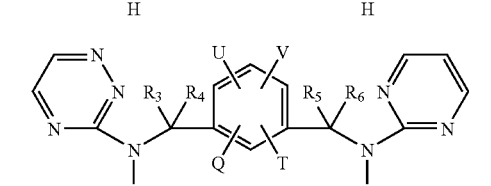
(III-16)

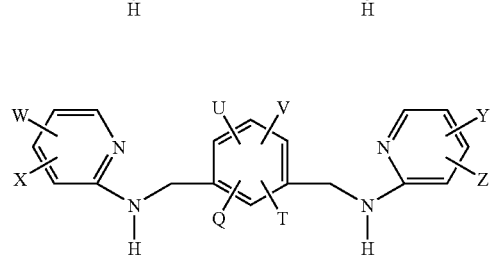
(III-17)

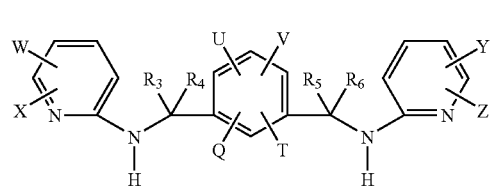
(III-18)

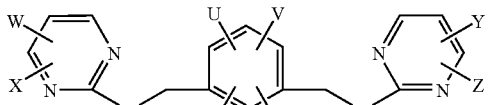
(III-19)

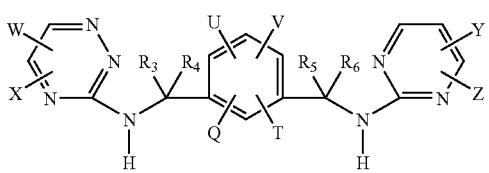
(III-20)

wherein

Q, T, U, V, W, X, Y and Z are as defined above; and $R_1$, $R_2$, $R_3$, $R_4$, $R_5$ and $R_6$ are as defined above.

In an fourth principal embodiment, the invention provides a compound of Formula IVa or IVb, or a pharmaceutically acceptable salt, ester or prodrug thereof:

Formula IVa

Formula IVb wherein each K is independently N or CH;

Q, T, U, V, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In one subembodiment of Formula IVa or IVb, Y and Z are each hydrogen. Alternatively, W and X are each hydrogen. In yet another subembodiment, W, X, Y and Z are all hydrogen.

In one subembodiment, the invention provides a compound of Formula IV-1 to IV-12, or a pharmaceutically acceptable salt, ester or prodrug thereof:

(IV-1)

(IV-2)
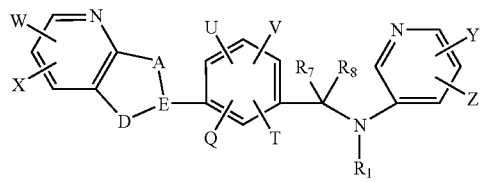
(IV-3)
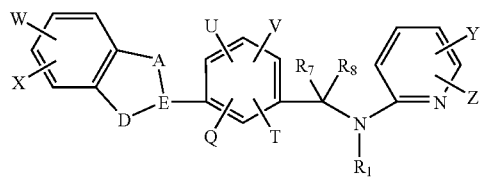
(IV-4)
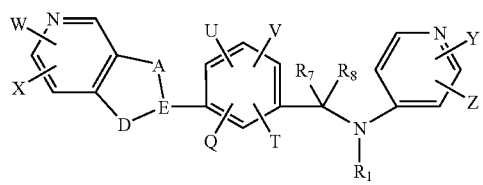
(IV-5)
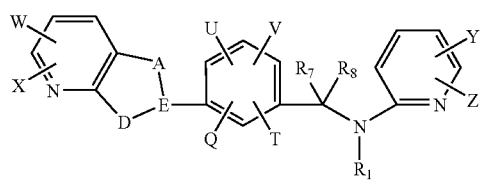
(IV-6)
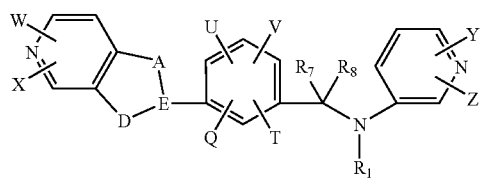
(IV-7)
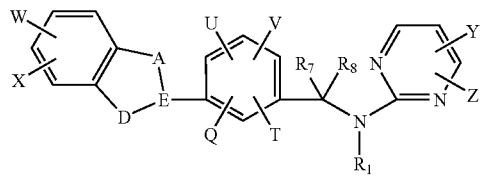
(IV-8)
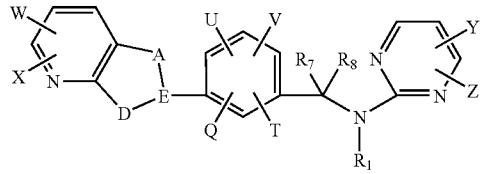
(IV-9)
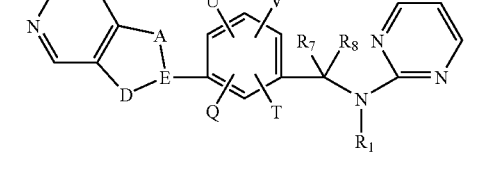
(IV-10)
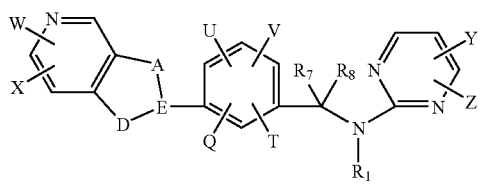
(IV-11)
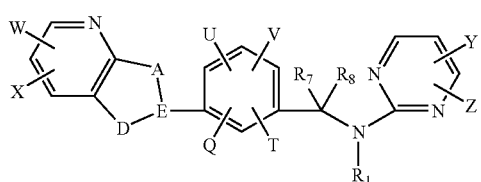
(IV-12)
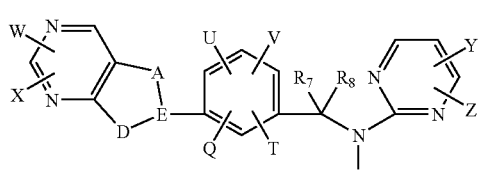
wherein
Q, T, U, V, W, X, Y and Z are as defined above;
$R_1$, $R_2$, $R_3$, $R_4$, $R_5$, $R_6$, $R_7$ and $R_8$ are as defined above; and
A and -D-E- are as defined above.
In another subembodiment, compounds of the Formula IV-13 to IV-20, or a pharmaceutically acceptable salt, ester or prodrug thereof, are provided:
(IV-13)
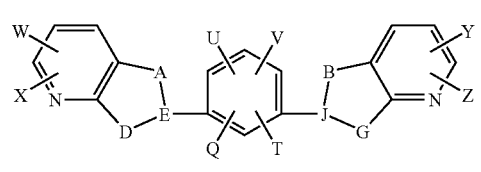
(IV-14)
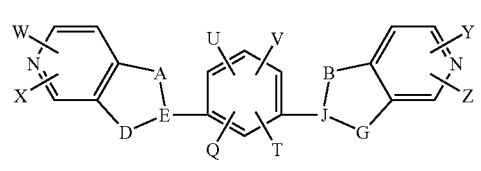
(IV-15)
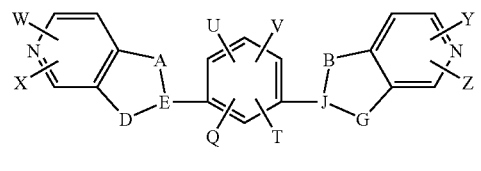
(IV-16)
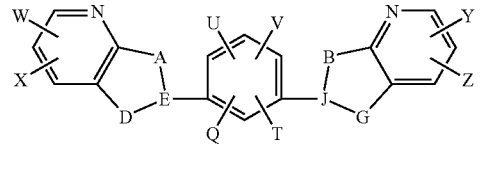

(IV-17)
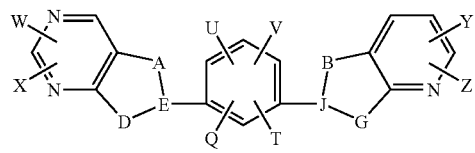

(IV-18)
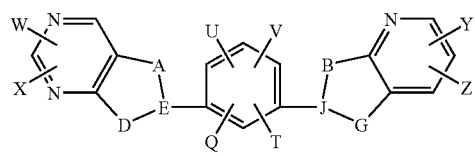

(IV-19)
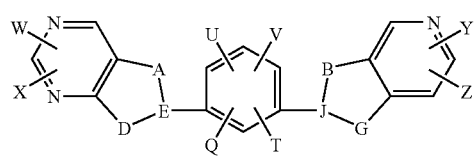

(IV-20)
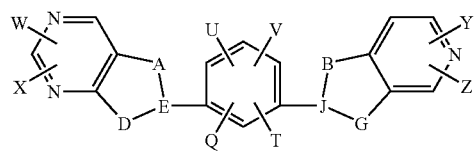

wherein
Q, T, U, V, W, X, Y and Z are as defined above;
$R_1$, $R_2$, $R_3$, $R_4$, $R_5$, $R_6$, $R_7$ and $R_8$ are as defined above; and
A, B, -D-E- and -G-J- are as defined above.

In an fifth principal embodiment, a compound of Formula Va, Vb, or Vc or a pharmaceutically acceptable salt, ester or prodrug thereof, is provided for the treatment or prevention of a disorder associated with CXCR4 receptor activation, and particularly a proliferative disorder, including cancer metastasis:

Formula Va
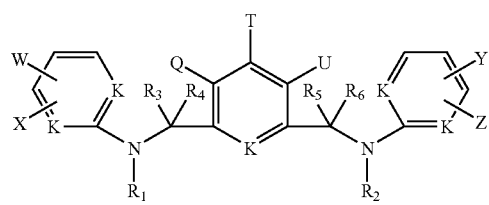

Formula Vb
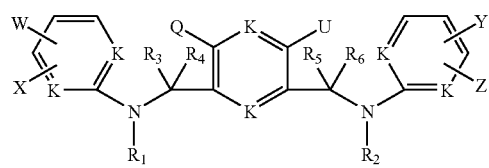

Formula Vc
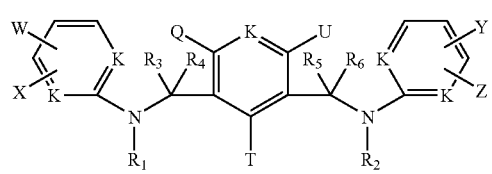

wherein
each K is independently N or CH;
Q, T, U, W, X, Y and Z are as defined above; and
$R_1$, $R_2$, $R_3$, $R_4$, $R_5$ and $R_6$ are as defined above.

In one subembodiment of Formula Va-c, Y and Z are each hydrogen. Alternatively, W and X are each hydrogen. In yet another subembodiment, W, X, Y and Z are all hydrogen.

In one subembodiment, a compound of Formula V-1 through V-3, or a pharmaceutically acceptable salt, ester or prodrug thereof, is provided for the treatment or prevention of a disorder associated with CXCR4 receptor activation, and particularly a proliferative disorder, including cancer metastasis:

(V-1)
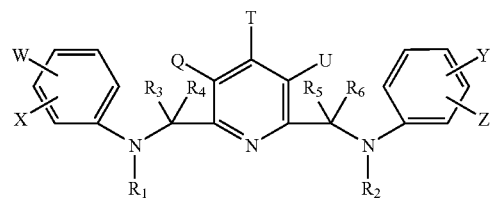

(V-2)
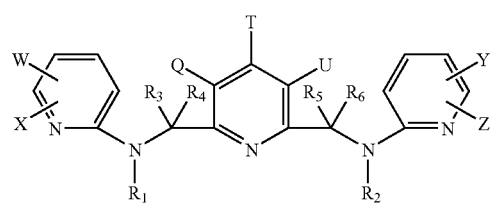

(V-3)
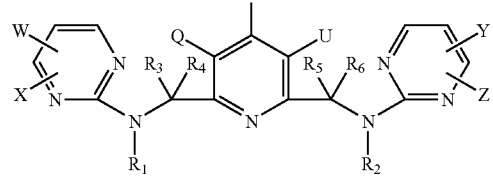

wherein
each K is independently N or CH;
Q, T, U, W, X, Y and Z are as defined above; and
$R_1$, $R_2$, $R_3$, $R_4$, $R_5$ and $R_6$ are as defined above.

In another subembodiment, a compound of Formula V-4 through V-9, or a pharmaceutically acceptable salt, ester or prodrug thereof, is provided for the treatment or prevention of a disorder associated with CXCR4 receptor activation, and particularly a proliferative disorder, including cancer metastasis:

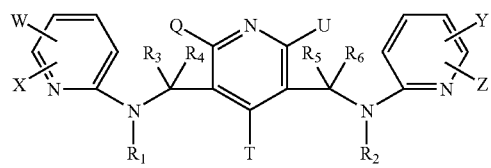
(V-4)

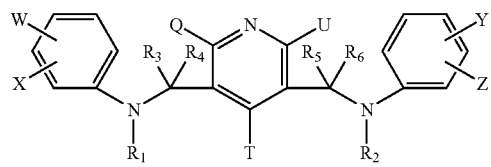
(V-5)

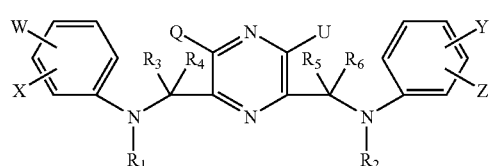
(V-6)

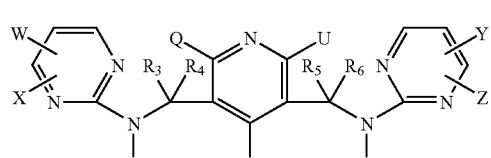
(V-7)

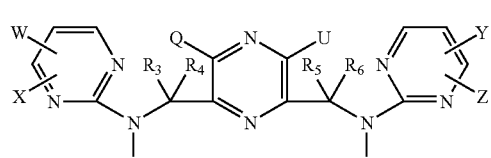
(V-8)

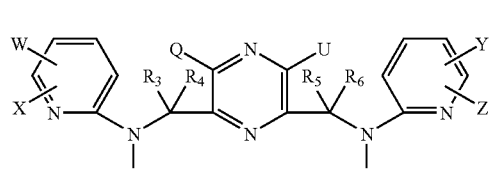
(V-9)

wherein
each K is independently N or CH;
Q, T, U, W, X, Y and Z are as defined above; and
$R_1$, $R_2$, $R_3$, $R_4$, $R_5$ and $R_6$ are as defined above.

In an sixth principal embodiment, the invention provides a compound of Formula VIa or VIb, or a pharmaceutically acceptable salt, ester or prodrug thereof:

Formula VIa

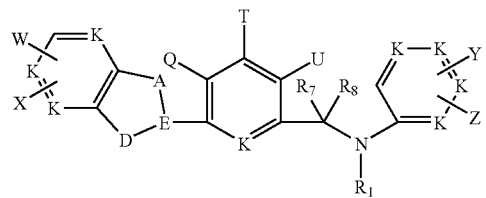

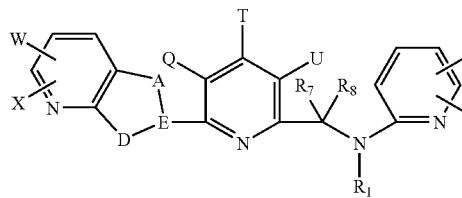

Formula VIb wherein
each K is independently N or CH;
Q, T, U, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In one subembodiment of Formula VIa or b, Y and Z are each hydrogen. Alternatively, W and X are each hydrogen. In yet another subembodiment, W, X, Y and Z are all hydrogen.

In one subembodiment, a compound of Formula VI-1 to VI-6, or a pharmaceutically acceptable salt, ester or prodrug thereof, is provided:

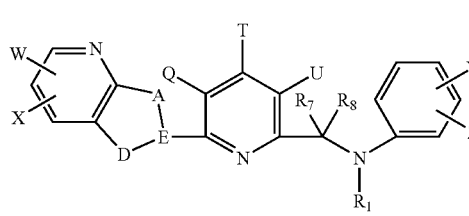
(VI-1)

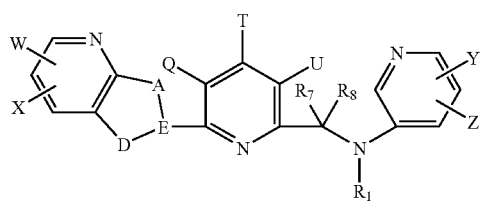
(VI-2)

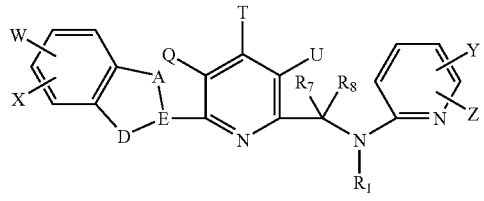
(VI-3)

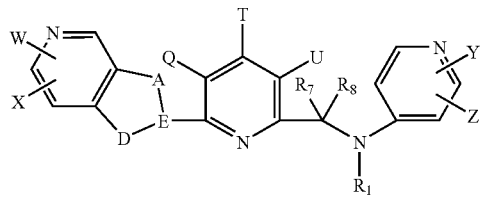
(VI-4)

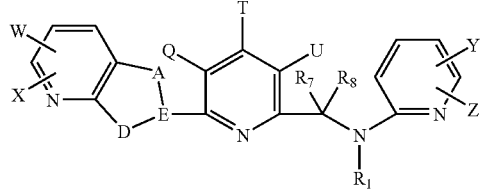
(VI-5)

-continued (VI-6)
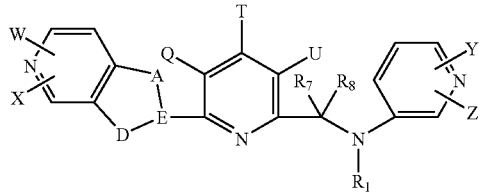

wherein
Q, T, U, W, X, Y and Z are as defined above;
$R_1$, $R_2$, $R_3$, $R_4$, $R_5$, $R_6$, $R_7$ and $R_8$ are as defined above; and
A and -D-E- are as defined above.

In another subembodiment, a compound of Formula VI-7 to VI-10, or a pharmaceutically acceptable salt, ester or prodrug thereof, is provided:

(VI-7)

(VI-8)

(VI-9)

(VI-10)

wherein
Q, T, U, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In an seventh principal embodiment, the invention provides a compound of Formula VII, or a pharmaceutically acceptable salt, ester or prodrug thereof:

Formula VII

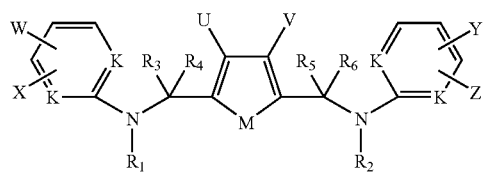

wherein
each K is independently N or CH;
U, V, W, X, Y and Z are as defined above;
$R_1$, $R_2$, $R_3$, $R_4$, $R_5$ and $R_6$ are as defined above; and
M is O, S or $NR_3$.

In one subembodiment of Formula VII, Y and Z are each hydrogen. Alternatively, W and X are each hydrogen. In yet another subembodiment, W, X, Y and Z are all hydrogen.

In one subembodiment, a compound of Formula VII-1 to VII-10, or a pharmaceutically acceptable salt, ester or prodrug thereof, is provided:

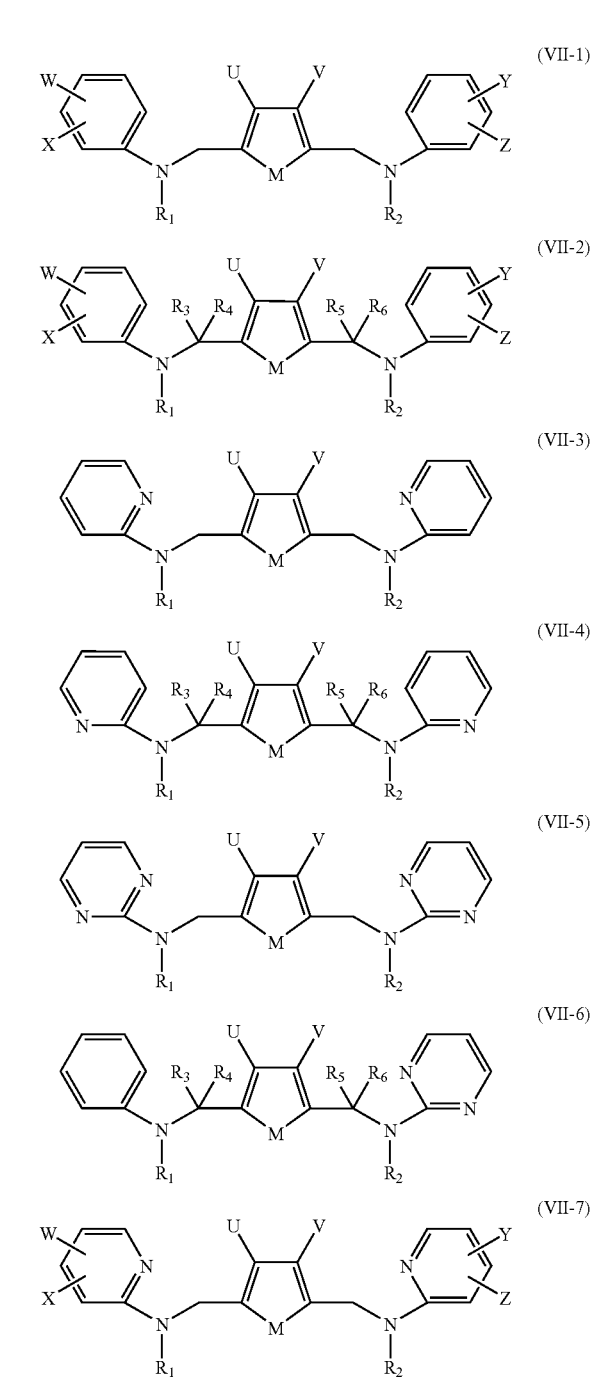

wherein

U, V, W, X, Y and Z are as defined above;

R$_1$, R$_2$, R$_3$, R$_4$, R$_5$ and R$_6$ are as defined above; and

M is O, S or NR$_3$.

In another subembodiment, a compound of Formula VII-11 to VII-20, or a pharmaceutically acceptable salt, ester or prodrug thereof, is provided:

wherein

U, V, W, X, Y and Z are as defined above;

R$_1$, R$_2$, R$_3$, R$_4$, R$_5$ and R$_6$ are as defined above; and

M is O, S of NR$_3$.

In an eight principal embodiment, the invention provides a compound of Formula VIIIa or VIIIb, or a pharmaceutically acceptable salt, ester or prodrug thereof:

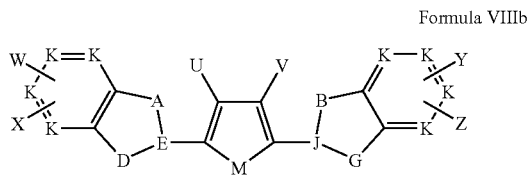

Formula VIIIb wherein each K is independently N or CH;

U, V, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above; and M is O, S or $NR_3$.

In one subembodiment of Formula VIIIa or b, Y and Z are each hydrogen. Alternatively, W and X are each hydrogen. In yet another subembodiment, W, X, Y and Z are all hydrogen.

In a subembodiment, a compound of Formula VIII-1 to VIII-12, or a pharmaceutically acceptable salt, ester or prodrug thereof, is provided:

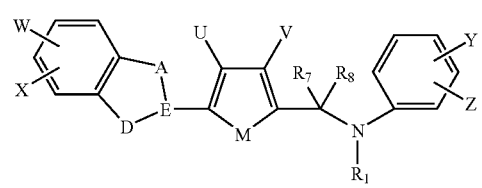

(VIII-1)

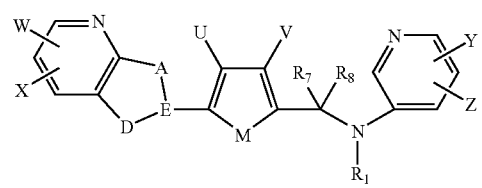

(VIII-2)

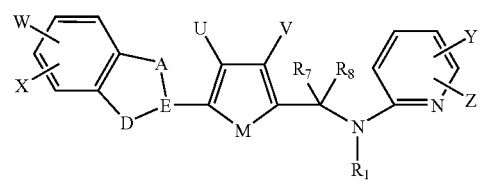

(VIII-3)

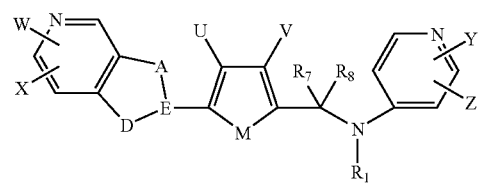

(VIII-4)

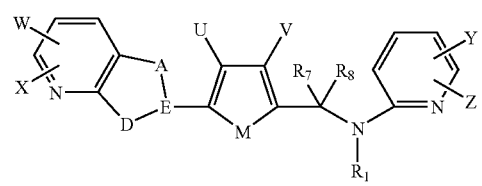

(VIII-5)

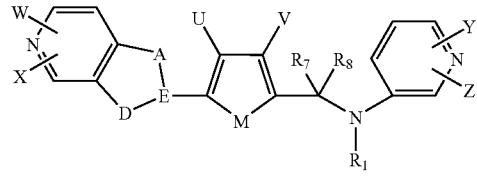

(VIII-6)

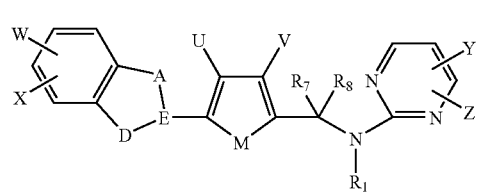

(VIII-7)

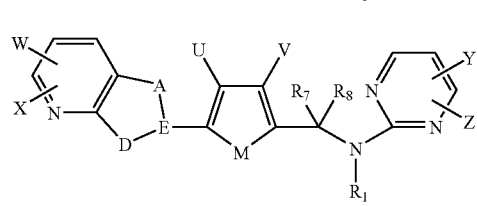

(VIII-8)

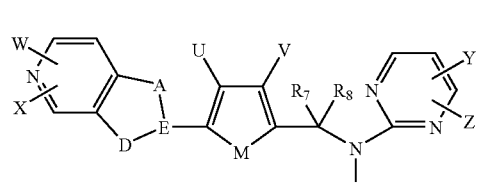

(VIII-9)

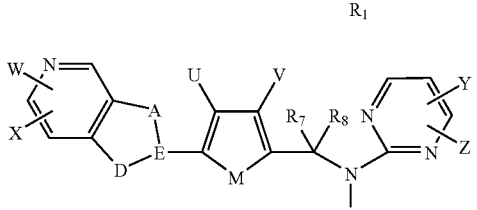

(VIII-10)

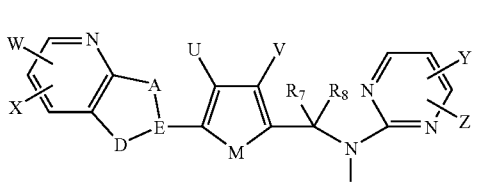

(VIII-11)

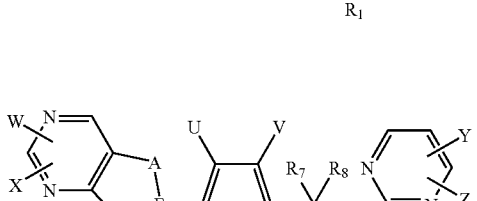

(VIII-12)

wherein

M, U, V, W, X, Y and Z are as defined above;

$R_1$, $R_2$, $R_3$, $R_4$, $R_5$, $R_6$, $R_7$ and $R_8$ are as defined above; and A and -D-E- are as defined above.

In another subembodiment, a compound of Formula VIII-13 to VIII-20, or a pharmaceutically acceptable salt, ester or prodrug thereof, is provided:

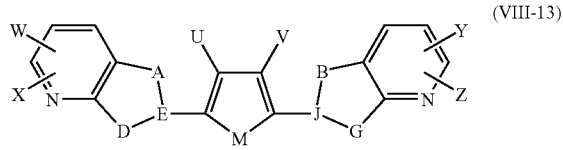 (VIII-13)

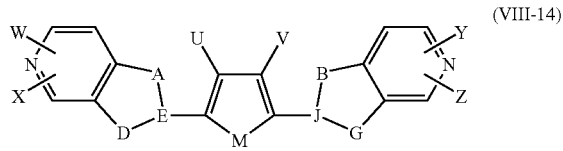 (VIII-14)

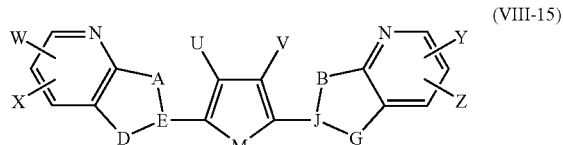 (VIII-15)

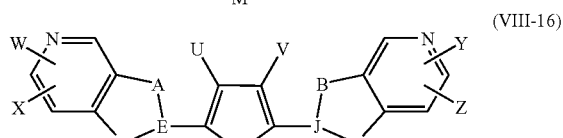 (VIII-16)

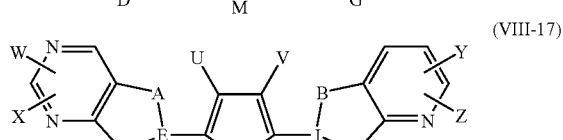 (VIII-17)

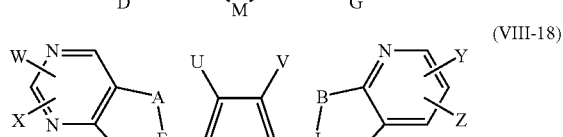 (VIII-18)

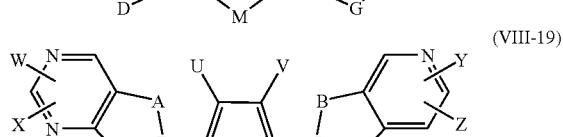 (VIII-19)

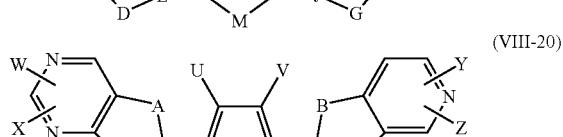 (VIII-20)

wherein
M, U, V, W, X, Y and Z are as defined above;
$R_1$, $R_2$, $R_3$, $R_4$, $R_5$, $R_6$, $R_7$ and $R_8$ are as defined above; and
A, B, -D-E- and -G-J- are as defined above.

In a ninth principal embodiment, the invention provides a compound of Formula IX, or a pharmaceutically acceptable salt, ester or prodrug thereof:

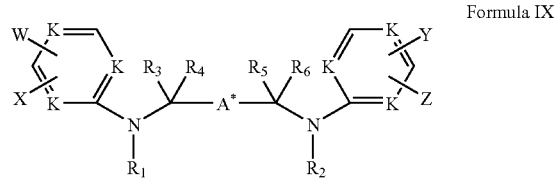 Formula IX wherein
each K is independently N or CH;
W, X, Y and Z are as defined above;
$R_1$, $R_2$, $R_3$, $R_4$, $R_5$ and $R_6$ are as defined above;
A* is independently selected from the group consisting of formulas a-g:

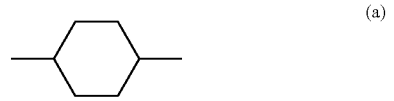 (a)

 (b)

 (c)

 (d)

 (e)

 (f)

———————; and (g)

M is O, S or $NR_3$.

In one subembodiment, a compound of Formula IX-1 to IX-12 is provided, or a pharmaceutically acceptable salt, ester or prodrug thereof:

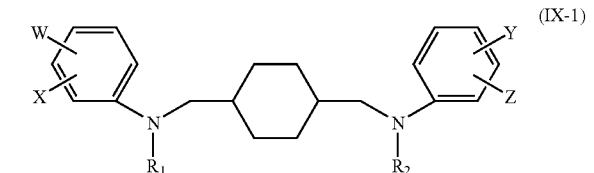 (IX-1)

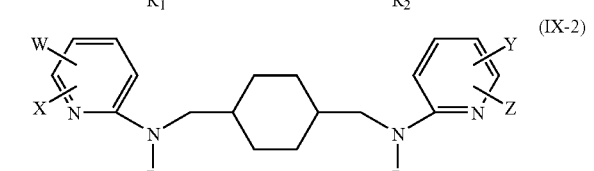 (IX-2)

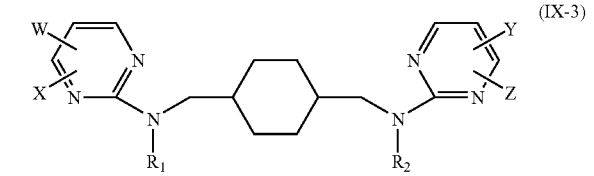 (IX-3)

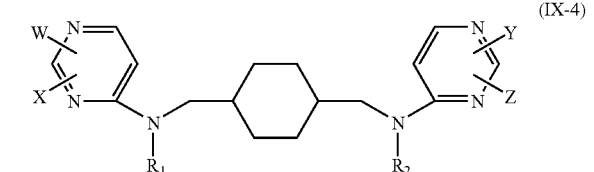 (IX-4)

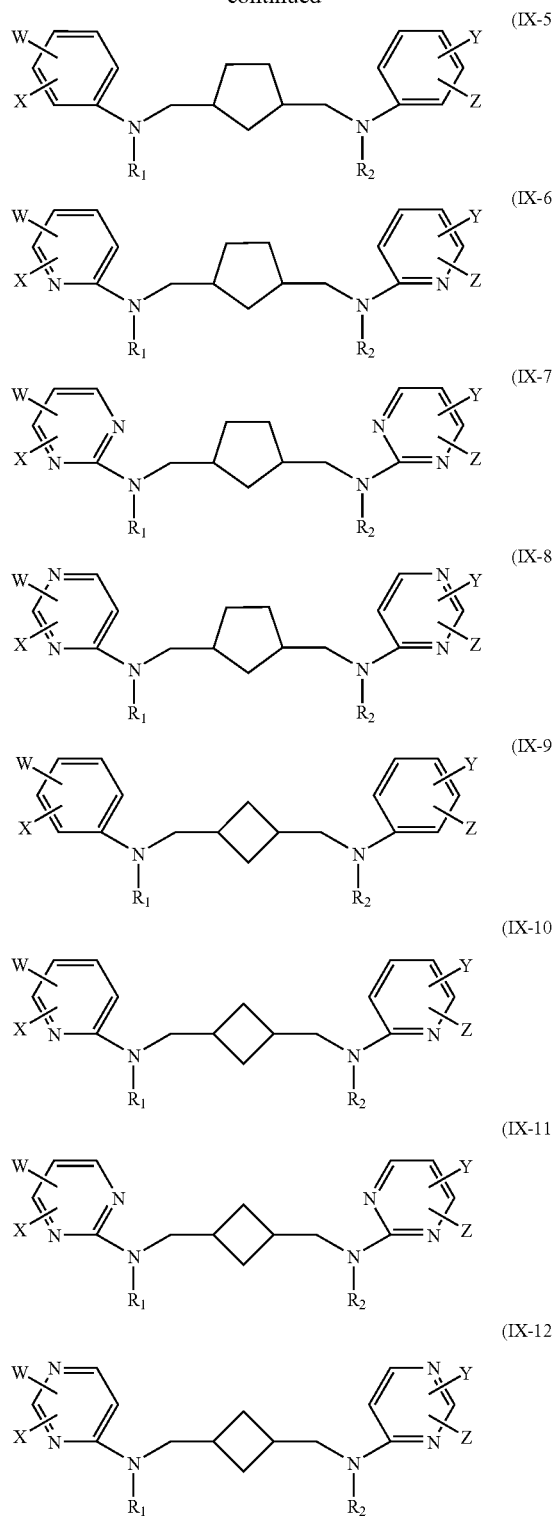
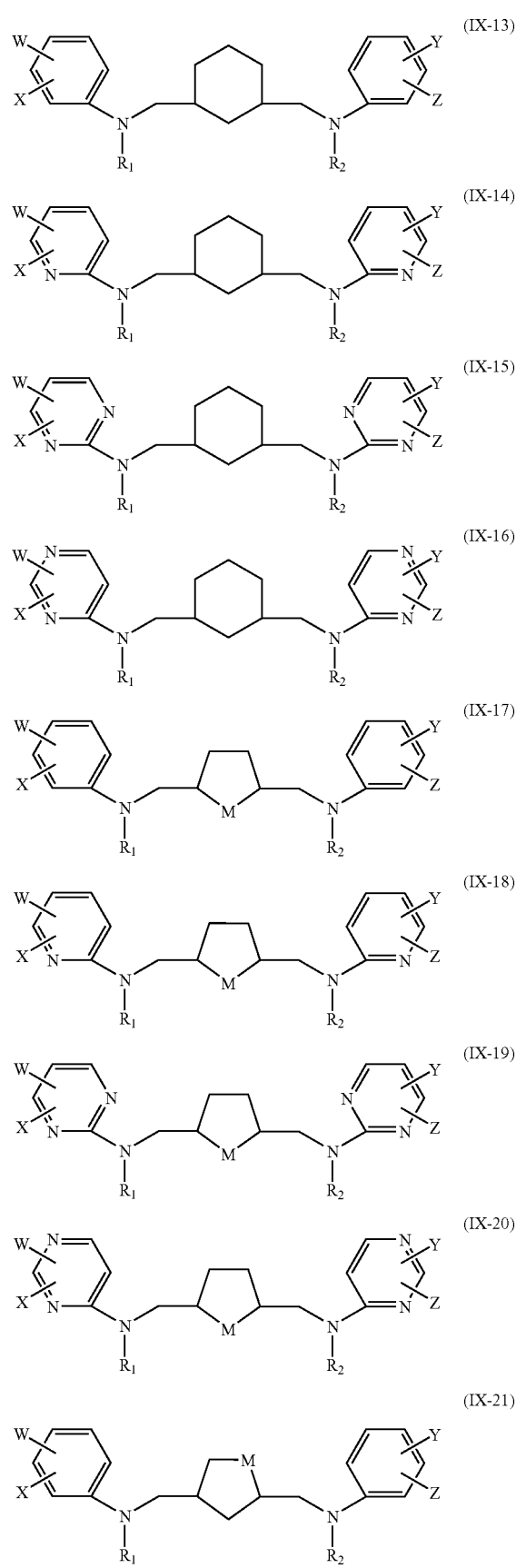
wherein
W, X, Y and Z are as defined above; and
$R_1$, $R_2$, $R_3$, $R_4$, $R_5$ and $R_6$ are as defined above.
In another subembodiment, a compound of Formula IX-13 to IX-24 is provided, or a pharmaceutically acceptable salt, ester or prodrug thereof:

wherein
M, W, X, Y and Z are as defined above; and
$R_1$, $R_2$, $R_3$, $R_4$, $R_5$ and $R_6$ are as defined above.

In yet another subembodiment, a compound of Formula IX-25 to IX-36 is provided, or a pharmaceutically acceptable salt, ester or prodrug thereof:

wherein
M, W, X, Y and Z are as defined above; and
$R_1$, $R_2$, $R_3$, $R_4$, $R_5$ and $R_6$ are as defined above.

In a tenth principal embodiment, the invention provides a compound of Formula X, or a pharmaceutically acceptable salt, ester or prodrug thereof:

Formula X

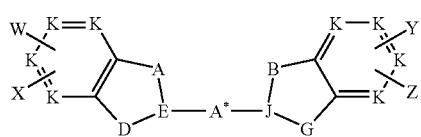

wherein
each K is independently N or CH;
W, X, Y and Z are as defined above;
$R_1, R_2, R_3, R_4, R_5, R_6, R_7$ and $R_8$ are as defined above; and
A and B and -D-E- and -G-J- are as defined above; and
A* is as defined above; and
M is as defined above.

In one subembodiment, a compound of Formula X-1 to X-14 is provided, or a pharmaceutically acceptable salt, ester or prodrug thereof:

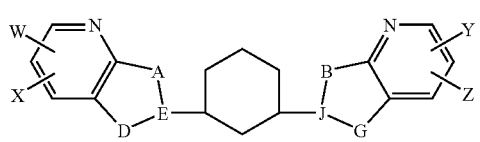 (X-1)

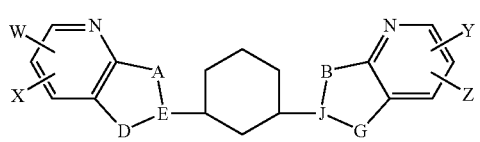 (X-2)

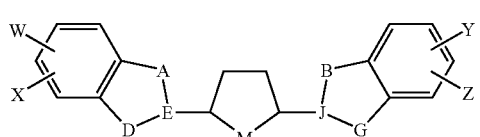 (X-3)

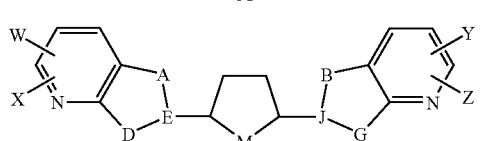 (X-4)

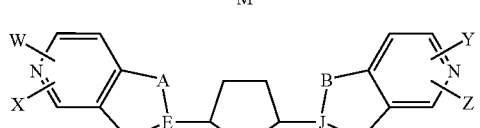 (X-5)

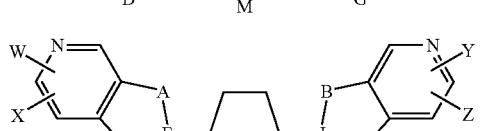 (X-6)

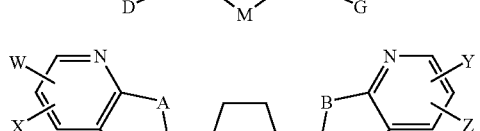 (X-7)

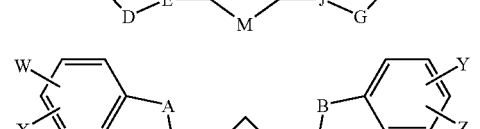 (X-8)

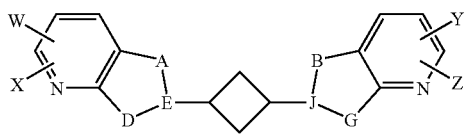 (X-9)

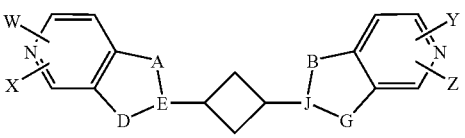 (X-10)

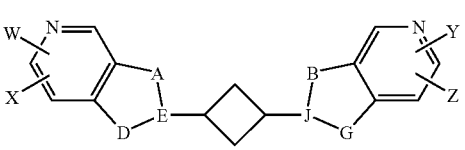 (X-11)

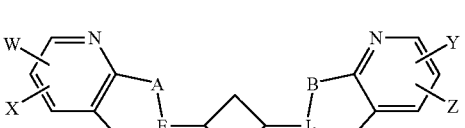 (X-12)

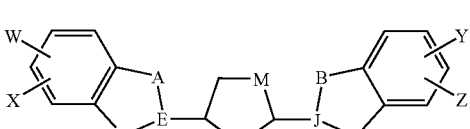 (X-13)

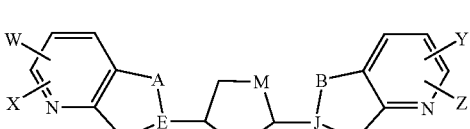 (X-14)

wherein
M, W, X, Y and Z are as defined above;
$R_1, R_2, R_3, R_4, R_5, R_6, R_7$ and $R_8$ are as defined above; and
A and B and -D-E- and -G-J- are as defined above.

In another subembodiment, a compound of Formula X-15 to X-28 is provided, or a pharmaceutically acceptable salt, ester or prodrug thereof:

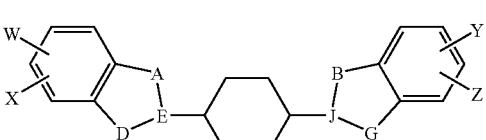 (X-15)

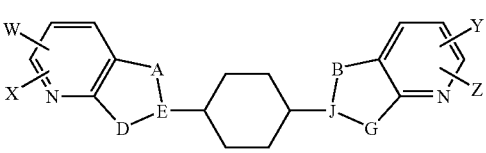 (X-16)

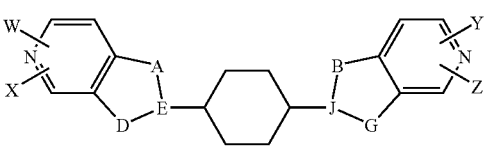 (X-17)

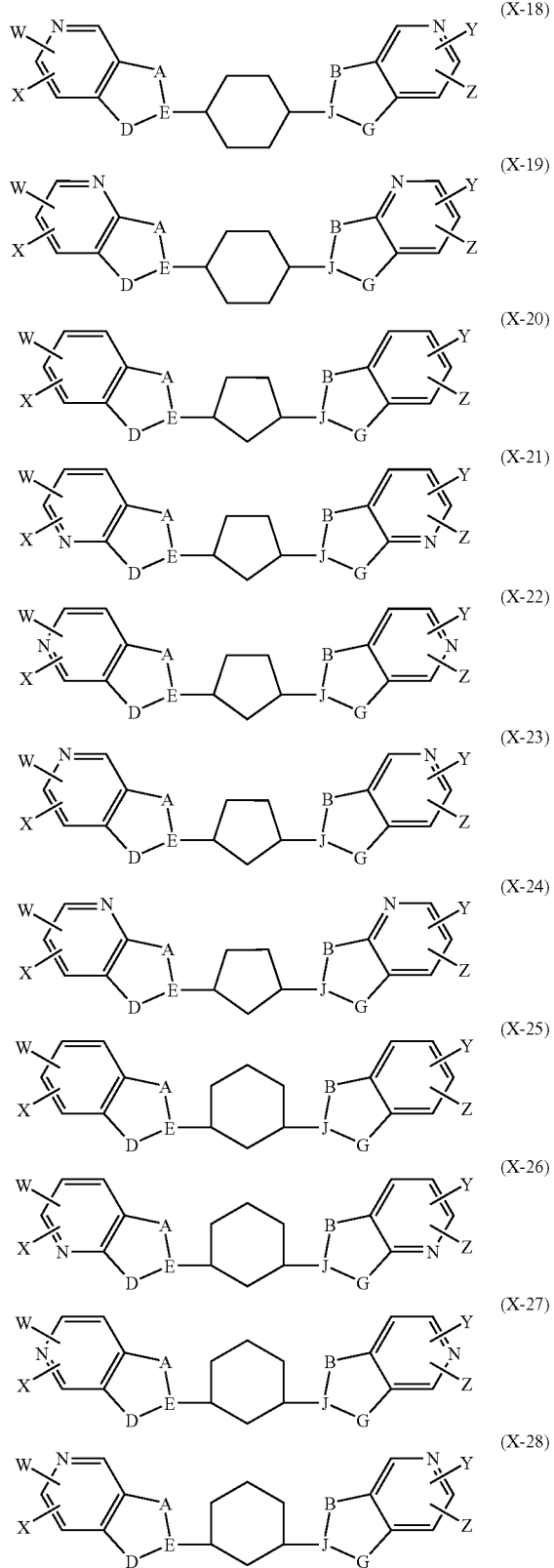
wherein
M, W, X, Y and Z are as defined above;
R$_1$, R$_2$, R$_3$, R$_4$, R$_5$, R$_6$, R$_7$ and R$_8$ are as defined above; and
A and B and -D-E- and -G-J- are as defined above.
In yet another subembodiment, a compound of Formula X-29 to X-38 is provided, or a pharmaceutically acceptable salt, ester or prodrug thereof:
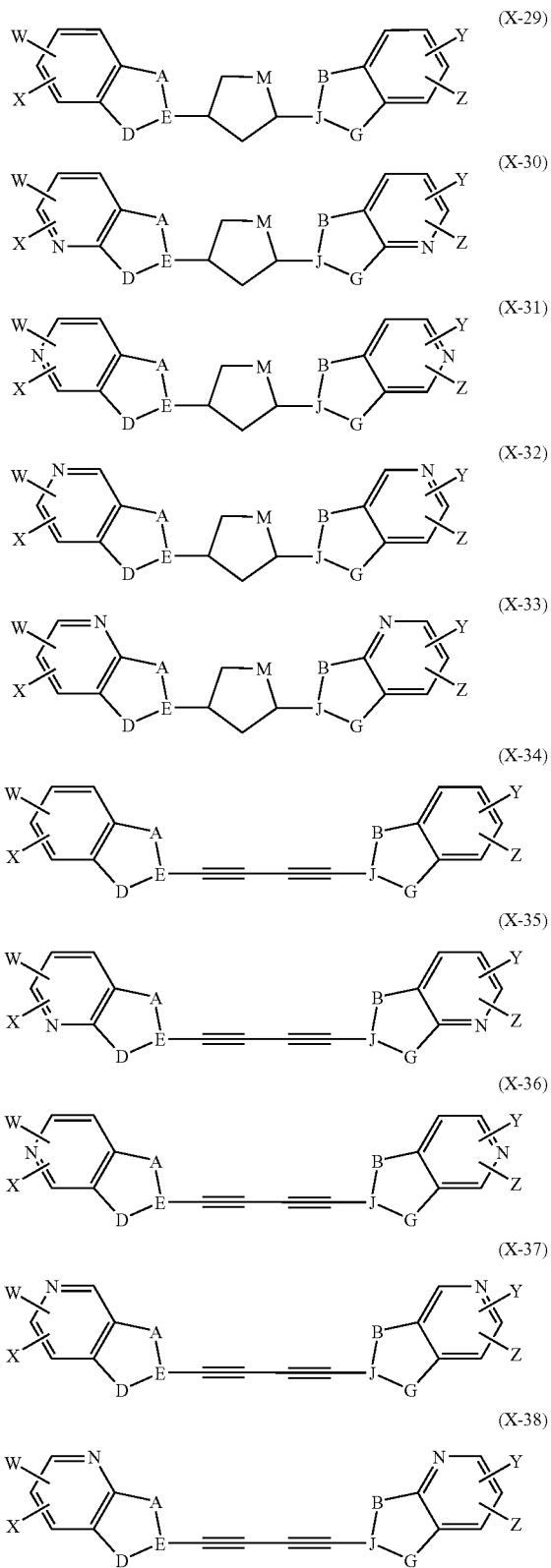

wherein

M, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In an eleventh principal embodiment, the invention provides a compound of Formula XI, or a pharmaceutically acceptable salt, ester or prodrug thereof:

Formula XI

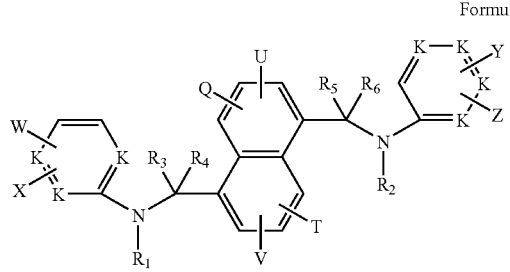

wherein each K is independently N or CH;

Q, T, U, V, W, X, Y and Z are as defined above; and $R_1$, $R_2$, $R_3$, $R_4$, $R_5$ and $R_6$ are as defined above.

In one subembodiment of Formula XI, Y and Z are each hydrogen. Alternatively, W and X are each hydrogen. In yet another subembodiment, W, X, Y and Z are all hydrogen.

In one subembodiment, a compound of Formula XI-1 to XI-6 is provided, or a pharmaceutically acceptable salt, ester or prodrug thereof:

(XI-1)

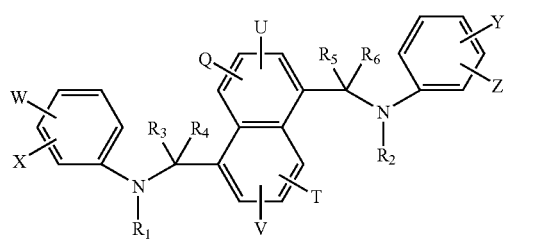

(XI-2)

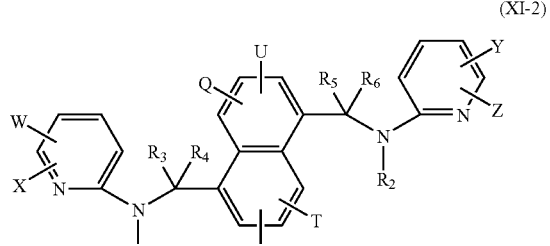

(XI-3)

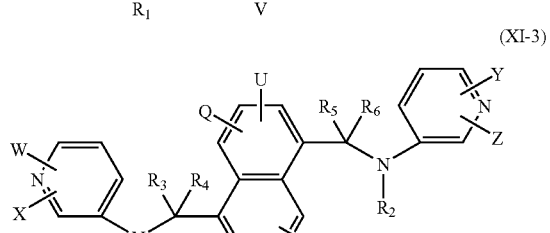

(XI-4)

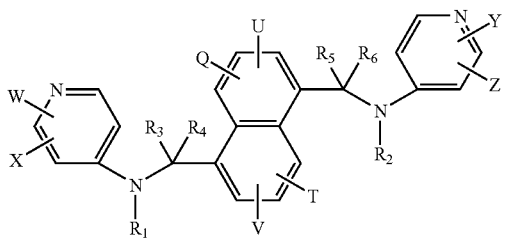

(XI-5)

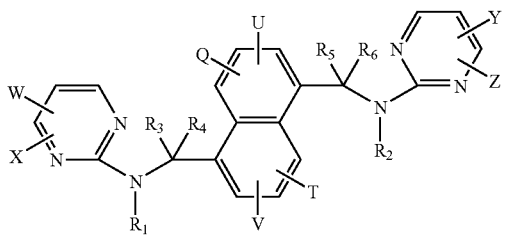

(XI-6)

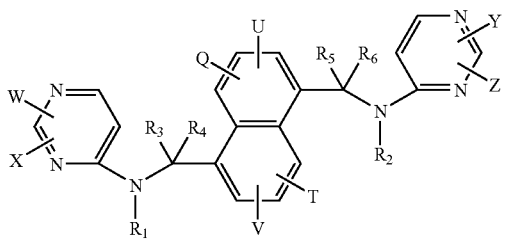

wherein

Q, T, U, V, W, X, Y and Z are as defined above; and $R_1$, $R_2$, $R_3$, $R_4$, $R_5$ and $R_6$ are as defined above.

In a twelfth principal embodiment, the invention provides a compound of Formula XII, or a pharmaceutically acceptable salt, ester or prodrug thereof:

Formula XII

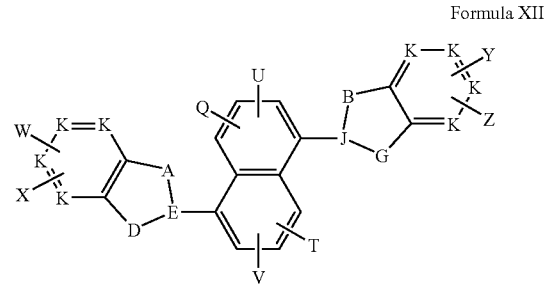

wherein each K is independently N or CH;

Q, T, U, V, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In one subembodiment of Formula XII, Y and Z are each hydrogen. Alternatively, W and X are each hydrogen. In yet another subembodiment, W, X, Y and Z are all hydrogen.

In one subembodiment, a compound of Formula XII-1 to XII-5 is provided, or a pharmaceutically acceptable salt, ester or prodrug thereof:

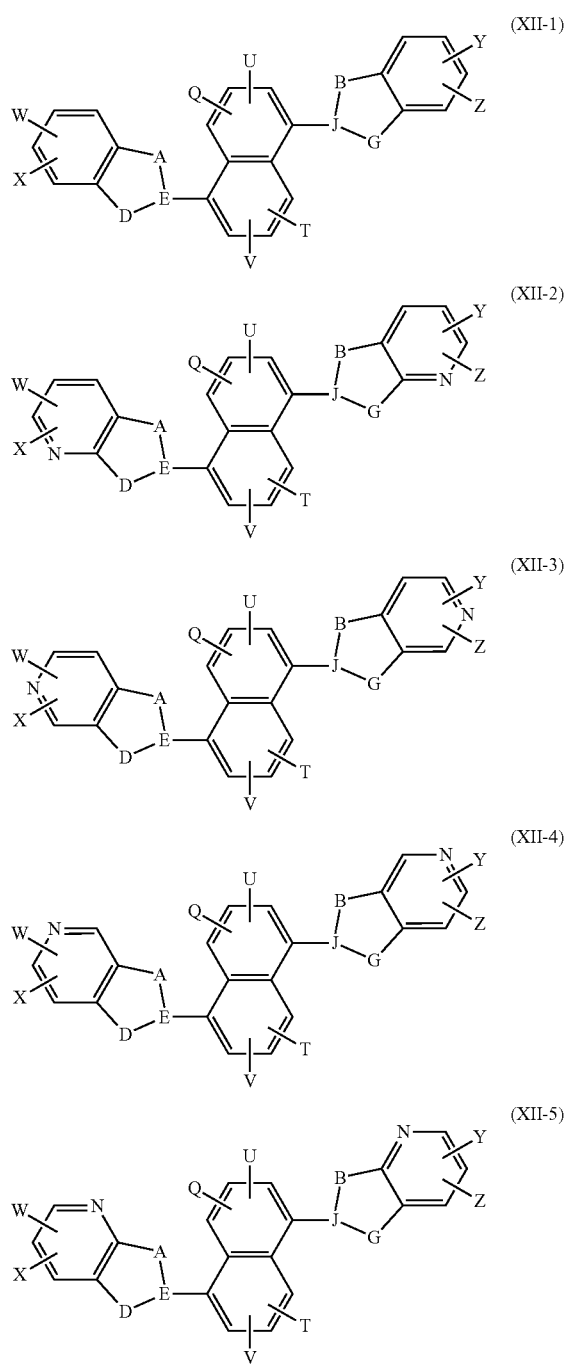

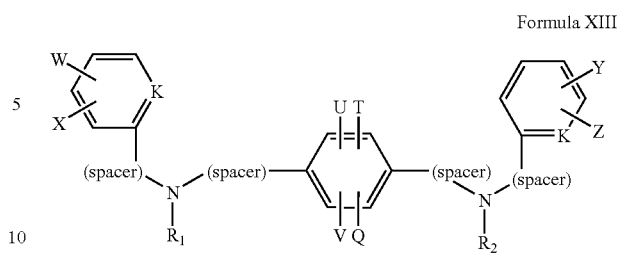

Formula XIII wherein

K, Q, T, U, V, W, X, Y and Z are as defined above;

$R_1$, $R_2$, $R_3$, $R_4$, $R_5$ and $R_6$ are as defined above; and

"spacer" is independently a bond, straight chained or branched $C_1$-$C_5$ alkyl, $C_2$-$C_5$ alkenyl, $C_2$-$C_5$ alkynyl, $C_1$-$C_5$ alkoxy, $C_2$-$C_5$ alkenoxy, and $C_2$-$C_5$ alkynoxy wherein the alkyl group can be substituted by a heteroatom (such as N, O or S) for example —$CH_2$—$OCH_2$—, —$CH_2CH_2$—$OCH_2$—, —$CH_2CH_2$—$OCH_2CH_2$—, —$CH_2$—$OCH_2CH_2$—, —$CH_2CH_2$—$OCH_2CH_2CH_2$—, —$CH_2CH_2CH_2$—$OCH_2$—, —$CH_2CH_2CH_2$—$OCH_2CH_2$—, —$CH_2CH_2$—$OCH_2CH_2CH_2$—, —$(CH_2)_n$—$OH(CH_3)$—$(CH_2)_n$—, $CH_2$—$OH(CH_3)$—$O$—$CH_2$, —$(CH_2)n$-, —$(CH_2)n$-$CO$—, —$(CH_2)n$-$N$—, —$(CH_2)n$-$O$—, —$(CH_2)n$-$S$—, —$(CH_2O)$—, —$(OCH_2)$—, —$(SCH_2)$—, —$(CH_2S)$—, -(aryl-$O$)—, —($O$-aryl)-, -(alkyl-$O$)—, —($O$-alkyl)- wherein n is independently 0, 1, 2, 3, 4, 5, 6, 7, 8, 9, or 10.

In a fourteenth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XIVa or XIVb, or a pharmaceutically acceptable salt, ester or prodrug thereof:

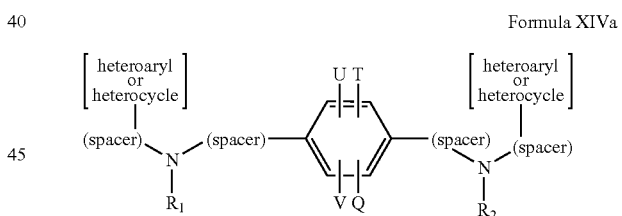

Formula XIVa

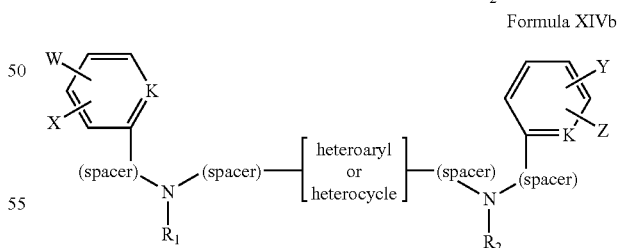

Formula XIVb wherein

K, Q, T, U, V, W, X, Y and Z are as defined above;

$R_1$, $R_2$, $R_3$, $R_4$, $R_5$ and $R_6$ are as defined above;

"spacer" is as defined above; and

"heterocycle" and "heteroaromatic" are as defined herein.

In one particular embodiment, a method of preventing metastasis of a malignant cell is provided that includes contacting the cells with a compound of Formula XV, or a pharmaceutically acceptable salt, ester or prodrug thereof:

wherein

Q, T, U, V, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In a thirteenth principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formula XIII, or a pharmaceutically acceptable salt, ester or prodrug thereof.

Formula XV

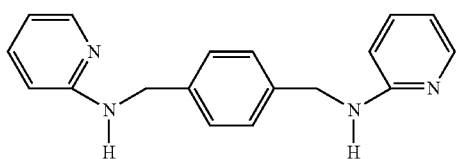

In a particular subembodiment, the compound is a salt of a compound of Formula XV, particularly a chloride salt.

In another particular embodiment, a method of preventing metastasis of a malignant cell is provided that includes contacting the cells with a compound of Formula XVI, or a pharmaceutically acceptable salt, ester or prodrug thereof:

Formula XVI

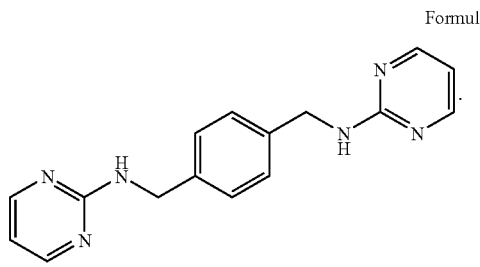

In another particular embodiment, a method of preventing metastasis of a malignant cell is provided that includes contacting the cells with a compound of Formula XVII, or a pharmaceutically acceptable salt, ester or prodrug thereof.

Formula XVII

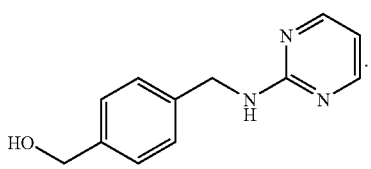

Definitions

The term alkyl, as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

Whenever the terms "$C_1$-$C_5$ alkyl", "$C_2$-$C_5$ alkenyl", "$C_1$-$C_5$ alkoxy", "$C_2$-$C_5$ alkenoxy", "$C_2$-$C_5$ alkynyl", and "$C_2$-$C_5$ alkynoxy" are used, these are considered to include, independently, each member of the group, such that, for example, $C_1$-$C_5$ alkyl includes straight, branched and where appropriate cyclic $C_1$, $C_2$, $C_3$, $C_4$ and $C_5$ alkyl functionalities; $C_2$-$C_5$ alkenyl includes straight, branched, and where appropriate cyclic $C_2$, $C_3$, $C_4$ and $C_5$ alkenyl functionalities; $C_1$-$C_5$ alkoxy includes straight, branched, and where appropriate cyclic $C_1$, $C_2$, $C_3$, $C_4$ and $C_5$ alkoxy functionalities; $C_2$-$C_5$ alkenoxy includes straight, branched, and where appropriate cyclic $C_2$, $C_3$, $C_4$ and $C_5$ alkenoxy functionalities; $C_2$-$C_5$ alkynyl includes straight, branched and where appropriate cyclic $C_1$, $C_2$, $C_3$, $C_4$ and $C_5$ alkynyl functionalities; and $C_2$-$C_5$ alkynoxy includes straight, branched, and where appropriate cyclic $C_2$, $C_3$, $C_4$ and $C_5$ alkynoxy functionalities.

The term lower alkyl, as used herein, and unless otherwise specified, refers to a $C_1$ to $C_4$ saturated straight, branched, or if appropriate, a cyclic (for example, cyclopropyl) alkyl group, optionally including substituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "pharmaceutically acceptable salt, ester or prodrug" is used throughout the specification to describe any pharmaceutically acceptable form (such as an ester, phosphate ester, salt of an ester or a related group) of a compound which, upon administration to a patient, provides the compound described in the specification. Pharmaceutically acceptable salts include those derived from pharmaceutically acceptable inorganic or organic bases and acids such as hydrochloric acid, hydrobromic acid, sulfuric acid, nitric acid, phosphoric acid, methanesulfonic acid, ethanesulfonic acid, p-toluensulfonic acid, salicylic acid, malic acid, maleic acid, succinic acid, tartaric acid, citric acid and the like. Suitable salts include those derived from alkali metals such as potassium and sodium, alkaline earth metals such as calcium and magnesium, among numerous other acids well known in the art.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "heterocyclic" refers to a nonaromatic cyclic group that may be partially (contains at least one double bond) or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Non-limiting examples of heterocylics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, tetrazolyl, benzofuranyl, quinolyl, isoquinolyl, benzothienyl, isobenzofuryl, indolyl, isoindolyl, benzimidazolyl, purine, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, 1,2,3-triazole, 1,2,4-triazole, 1,2,3-oxadiazole, thiazine, pyridazine, benzothiophenyl, isopyrrole, thiophene, pyrazine, or pteridinyl wherein said heteroaryl or heterocyclic group can be optionally substituted with one or more substituent selected from the group consisting of halogen, haloalkyl, alkyl, alkoxy, hydroxy, carboxyl derivatives, amido, hydroxyl, acyl, amino, alkylamino, dialkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl.

The term purine or pyrimidine includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine.

Processes for the Preparation of Active Compounds

General Methods. $^1$H NMR or $^{13}$C NMR spectra were recorded either on 400 MHz or 100 MHz INOVA Spectrometer or 600 MHz or 150 MHz INOVA Spectrometer. The spectra obtained were referenced to the residual solvent peak. They were recorded in deuterated chloroform, dimethyl sulfoxide-d6, deuterium oxide or acetone-d6. Melting points were taken on a Thomas Hoover capillary melting point apparatus and are uncorrected. Low-resolution EI mass spectra were recorded on a JEOL spectrometer. Element analyses were performed by Atlantic Mircolab (Norcross, Ga.). Flash column chromatography was performed using Scientific Absorbent Incorporated Silica Gel 60. Analytical thin layer chromatography (TLC) was performed on precoated glass backed plates from Scientific Adsorbents Incorporated (Silica Gel 60 $F_{254}$). Plates were visualized using ultraviolet or iodine vapors or phosphomolybdic acid (PMA).

Six different methods were used to prepare the compounds of the invention and the characterization data were listed in Table 1.

Method A: Nucleophilic addition between amines and cyanamides. This method is performed according to a modified literature procedure (Braun, et al. (1938) *J. Am. Chem. Soc.* 3: 146-149). 1.0 eq. of diamine dihydrohalide and 3.0 eq. of cyanamide in absolute ethanol were stirred together under refluxing for hours. The solvent was removed under reducing pressure to get the crude salt which was purified by recrystallization in methanol.

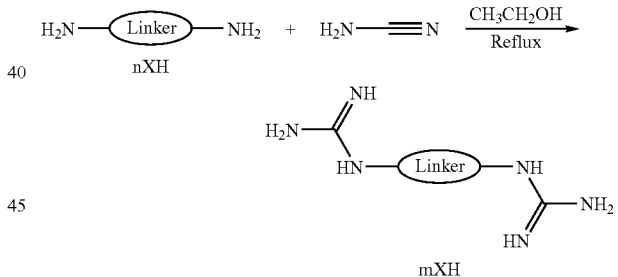

Method B: Addition-elimination between amines and methyl mercapto derivatives. This method is almost similar to a literature procedure (Linton, et al. (2001) *J. Org. Chem.* 66(22): 7313-7319). 1.0 eq. of diamine and 2.0 eq. methyl mercapto hydrohalide derivatives were dissolved in methanol. A condenser equipped with a NaOH trap at the top was attached. After refluxing for hours, the solution was reduced to minimal volume under reduced pressure. Ethyl either was added to produce white precipitate. This was recrystallized in hot methanol to give pure product.

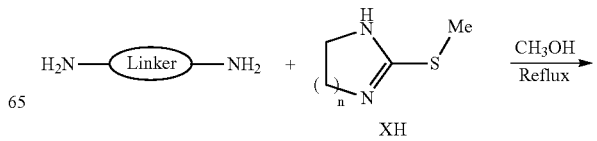

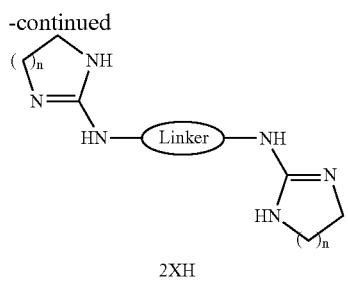

Method C: Condensation between aldehydes/ketones and amino guanidines to give guanylhydrozone derivatives. This method is modified from the literature procedure (Murdock, et al. (1982) *J. Med. Chem.* 25:505-518). A mixture of 1.0 eq. dialdehyde/ketone and 2.0 eq. amino guanidine hydrohalides in ethanol was heated under reflux for hours. The mixture was cooled to room temperature and filtered to give the guanylhydrozone hydrohalides.

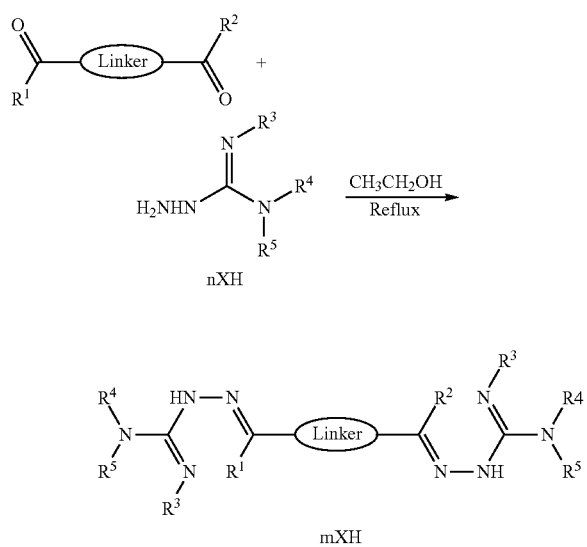

Method D: Reductive amination between aldehydes/ketones and amines (Abdel-Magid, et al. (1996) *J. Org. Chem.* 61:3849-3862). 1.0 eq. dialdehydes or ketones and 2.0 eq. amines were mixed in 1,2-dichloroethane and then treated with 3.0 eq. sodium triacetoxyborohydride (1.0-2.0 mol eq. acetic acid may also be added in reactions of ketones). The mixture was stirred at room temperature under an argon or nitrogen atmosphere for hours until the disappearance of the reactants in TLC plates. The reaction mixture was quenched by adding 1 N NaOH, and the product was extracted by ethyl ether, washed by Brine and dried by anhydrous $MgSO_4$. The solvent was evaporated to give the crude free base which could be purified by chromatography. The free base dissolved in ethanolic hydrochloride or tartaric acid to give the salts which usually can recrystallize from $MeOH/Et_2O$.

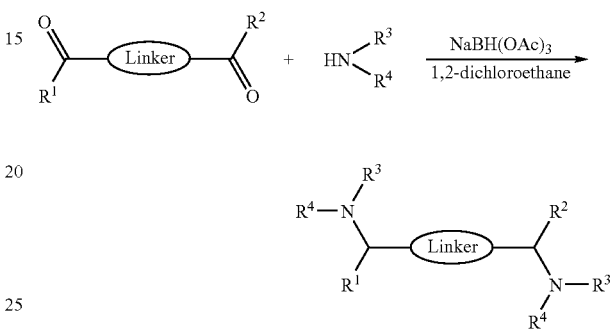

Method E: Reduction of amides (Micovic and Mihailovic (1953) *J. Org. Chem.* 18:1190). The amides could be prepared from the corresponding carboxylic acid or carboxylic chlorides. A mixture of carboxylic acid and thionyl chloride was refluxed for hours in an anhydrous system with a condenser equipped with a NaOH trap at the top. The excess thionyl chloride was removed under reduced pressure to get the carboxylic chloride. The carboxylic chloride was dissolved in dichloromethane following the addition of 2.0 eq. amine and 3 eq. pyridine. The mixture was stirred at room temperature until the disappearance of the reactants in the TLC plates. The solvent was removed under reduced pressure to get the crude amides which can be purified by chromatography.

The mixture of 1 eq. amide and 1.9 eq. $LiAlH_4$ in THF was refluxed until the disappearance of the amide from TLC plates. Then the solution was quenched with the addition of water and 15% NaOH aqueous as described in lit.5 and extracted with ethyl ether, dried over $MgSO_4$. Removal of the solvent gave the free amine product which can be purified by the chromatography. The free base dissolved in ethanolic hydrochloride or tartaric acid to give the salts which usually can recrystallize from $MeOH/Et_2O$.

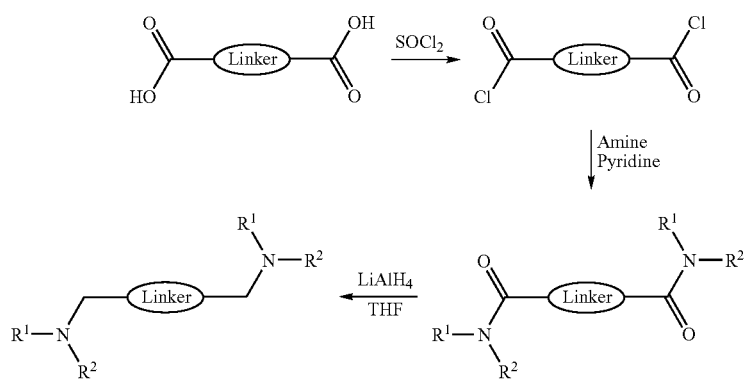

Method F: Nucleophilic substitution of halides with amines. A mixture of 1.0 eq. halides, 2.0 eq. amines and 3 eq. pyridine in ethanol was refluxed for hours until the disappearance of the reactants. The solution was condensed and extracted with ethyl ether, washed with brine, dried with MgSO$_4$. Removal of the solvent gave the free amine product which can be purified by the chromatography. The free base dissolved in ethanolic hydrochloride or tartaric acid to give the salts which usually can recrystallize from MeOH/Et$_2$O.

TABLE 1

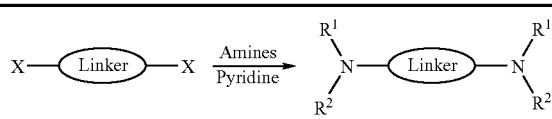

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ1S | 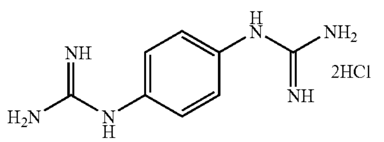 | D$_2$O: 600 Mz 1H: 7.40 (4H, s) 13C: 159.019, 136.364, 129.981 | 302-304 (dec) | C$_8$H$_{14}$Cl$_2$N$_6$ C: 36.34 (36.24); H: 5.34 (5.32); N: 31.76 (31.70) Cl: 26.70 (26.74) | |
| WZ3S | 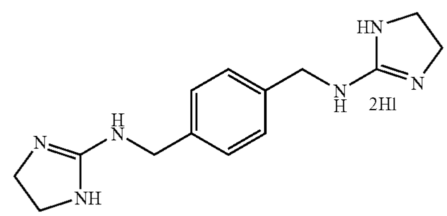 | DMSO: 400 Mz 1H: 8.66 (2H, s); 7.6-8.6 (4H, br); 7.31 (4H, s); 4.36 (4H, s); 3.60 (8H, s) 13C: 159.31, 136.50, 127.53, 45.06, 42.54 | 294-296 (dec) | C$_{14}$H$_{22}$I$_2$N$_6$ C: 32.06 (31.84) H: 4.35 (4.20) N: 15.77 (15.91) | |
| WZ4S | 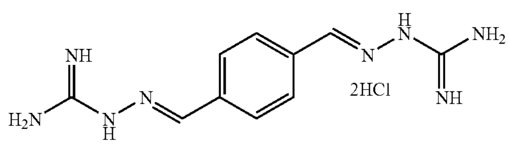 | DMSO: 400 Mz 1H: 12.28 (2H, s); 8.21 (2H, s); 7.94 (4H, s); 7.60-8.20 (8H, br) 13C: 155.52, 145.98, 135.18, 127.84 | 316-318 (dec) | C$_{10}$H$_{16}$Cl$_2$N$_8$.0.7 H$_2$O C: 36.07 (36.20); H: 5.23 (5.29); N: 33.42 (33.77); Cl: 21.11 (21.37) | |
| WZ5S | 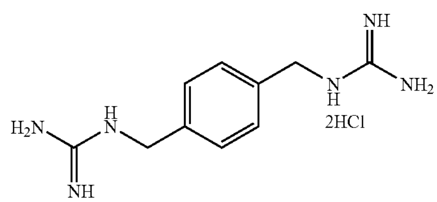 | DMSO: 409 Mz 1H: 8.08 (2H, s); 7.32 (4H, s); 6.85-7.71 (8H, br); 4.37 (4H, s) 13C: 157.12, 136.61, 127.53, 43.65 | 278-281 (dec) | | |
| WZ6S | 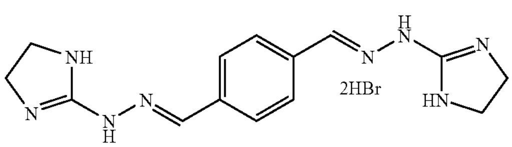 | DMSO: 400 Mz 1H: 12.39 (2H, s); 8.3-9.2 (4H, br); 8.22 (2H, s); 7.92 (4H, s); 3.75 (8H, s) 13C: 195.31, 136.50, 127.53, 45.06, 42.54 | 349-352 (dec.) | C$_{14}$H$_{20}$Br$_2$N$_8$ C: 41.19 (40.96) H: 6.35 (6.19) N: 28.32 (28.66) | |
| WZ7S | 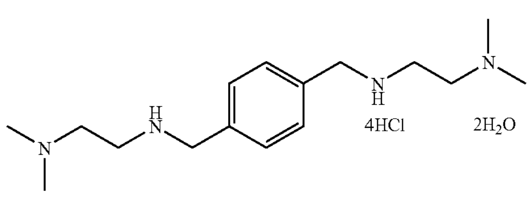 | D$_2$O: 1H (600 MHz): 7.58 (4H, s); 4.37 (4H, s), 3.58 (8H, s); 2.98 (12H, s) 13C (400 Mz): 131.95, 130.81, 52.45, 51.30, 43.45, 41.45 | 250-252 (dec.) | C$_{16}$H$_{38}$Cl$_4$N$_4$O$_2$ C: 41.75 (41.83) H: 8.32 (8.26) N: 12.17 (11.92) | |

TABLE 1-continued

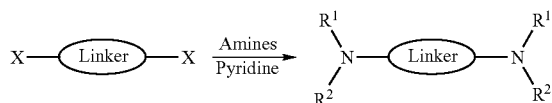

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ8S | (structure shown, 2HCl) | D$_2$O: 400 Mz 1H: 7.45 (4H, s); 7.24 (4H, t J = 7.2 Hz); 6.82 (2H, t, J = 7.2 Hz); 6.73 (4H, d, J = 7.2 Hz); 4.27 (4H, s); 3.47 (4H, t, J = 6.2 Hz); 3.24 (4H, t, J = 6.2 Hz) | 320-322 (dec.) | C$_{24}$H$_{32}$Cl$_2$N$_4$ C: 64.42 (64.32) H: 7.21 (7.21) N: 12.52 (12.30) | |
| WZ8 | (structure shown) | CDCl3: 1H (600 MHz): 7.29 (4H, s); 7.18 (4H, t, J = 5.2 Hz); 6.71 (2H, t, J = 4.8 Hz); 6.64 (4H, d, J = 6 Hz), 3.81 (4H, s); 3.23 (4H, t, J = 3.6 Hz); 2.91 (4H, t, J = 3.6 Hz); 4.12 (2H, br) 13C (400 Mz): 148.64; 139.18; 129.38; 128.36; 117.53; 113.13; 53.49; 48.17; 43.65 | 42-43 | | |
| WZ9S | (structure shown, 4HCl) | D$_2$O: 400 Mz 1H: 8.87 (4H, d, J = 7.2 Hz); 8.12 (4H, d, J = 7.2 Hz); 7.63 (4H,); 4.66 (4H,); 4.48 (4H, s) 13C: 151.21; 142.45; 131.84; 131.18; 127.47; 51.35; 49.03 | 244-246 (dec.) | C$_{20}$H$_{26}$Cl$_4$N$_4$·0.7 H$_2$O C: 50.60 (50.37) H: 5.74 (5.79) N: 11.49 (11.75) | |
| WZ9 | (structure shown) | CDCl3: 1H (600 Mz): 8.55 (4H, d, J = 5.4 Hz); 7.32 (4H, s); 7.30 (4H, d, J = 5.4 Hz); 3.83 (4H,); 3.81 (4H, s); 1.73 (2H, s) 13C (400 Mz): 149.73; 149.38; 138.72; 128.21; 122.93; 52.84; 51.72 | | | |
| WZ29S | (structure shown, 4HCl) | D2O: 600 Mz 1H: 8.87 (4H, d J = 7.2 Hz); 8.12 (4H, d, J = 7.2 Hz); 7.63 (4H, s); 4.66 (4H, s); 4.48 (4H, s) | | C20H26Cl4N4· 0.7H2O C: 50.57 (50.37) H: 5.70 (5.79) N: 11.55 (11.75) | |

TABLE 1-continued

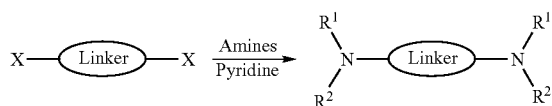

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ10S | 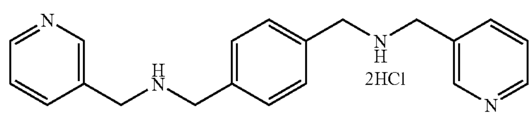 | D$_2$O: 1H: 600 mHz 8.61 (2H, dd, J = 6 Hz, 1.2 Hz); 8.60 (2H, d, J = 2.4 Hz); 7.99 (2H, dt, J = 7.8 Hz, 1.8 Hz); 7.56 (6H, m); 4.39 (4H, s); 4.37 (4H, s) 13C: 400 MHz 148.85; 149.82; 139.26; 132.13; 130.81; 127.48; 124.83; 50.48; 48.15 | 318-320 (dec.) | C$_{20}$H$_{24}$Cl$_2$N$_4$ C: 60.45 (61.38) H: 6.17 (6.18) N: 13.89 (14.32) | |
| WZ11S | 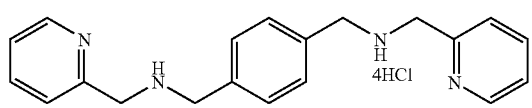 | D$_2$O: 1H: 8.76 (2H, d, J = 4.8 Hz); 8.35 (2H, dt, J = 8 Hz, J = 1.2 Hz); 7.91 (2H, d, J = 8 Hz); 7.86 (2H, t, J = 6.4 Hz); 4.62 (4H, s); 4.47 (4H, s) 13C: 146.12; 145.53; 144.95; 131.84; 131.07; 127.47; 127.26; 51.18; 47.91 | 236-238 (dec.) | C$_{20}$H$_{26}$Cl$_4$N$_4$0.5 H$_2$O 0.2CH$_3$COOCH$_2$CH$_3$ C: 50.59 (50.89) H: 6.08 (5.87) N: 11.46 (11.41) | |
| WZ13S | 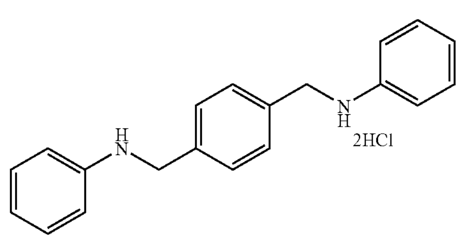 | DMSO-D2O: 400 Mz 1H: 7.35 (4H, s), 7.30 (4H, m), 7.10 (6H, m), 4.41 (4H, s) 13C: 137.85, 133.27, 129.88, 129.46, 126.58, 121.70, 51.82 | | | |
| WZ13 | 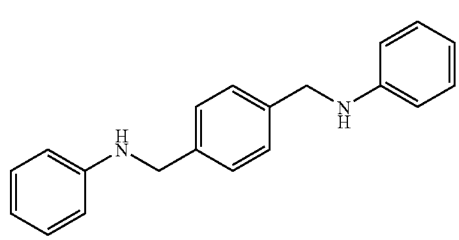 | CDCl3: 400 Mz 1H; 7.38 (4H, s); 7.22 (4H, t, J = 7.6 Hz); 6.76 (2H, t, J = 7.6 Hz); 7.67 (4H, d, J = 7.6 Hz); 4.35 (4H, s); 4.06 (2H, br) 13C: 148.28, 138.65, 129.46, 127.98, 117.78, 113.03, 48.20 | 126-127 | | |

TABLE 1-continued
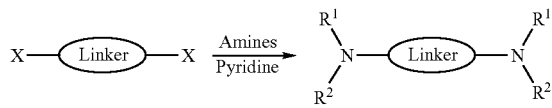
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ14 | 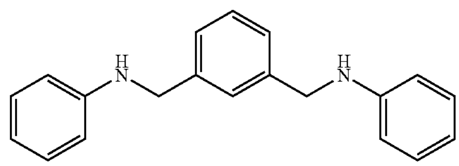 | CDCl3: 400 Mz 1H: 7.43 (1H, s); 7.36 (3H, m); 7.23 (4H, m); 6.78 (2H, t, J = 7.7 Hz); 6.68 (4H, d, J = 7.7 Hz); 4.07 (2H, s) 13C: 148.26, 140.09, 129.44, 129.03, 126.74, 126.54, 117.77, 113.05, 48.42 | | | 288.5 (288.4) |
| WZ14S | 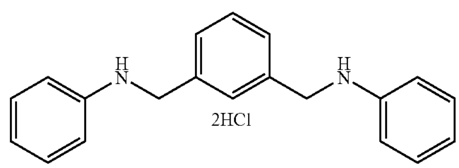 | D2O: 400 Mz 1H: 7.49 (6H, m); 7.37 (3H, m); 7.21 (4H, m); 7.15 (1H, s); 4.59 (4H, s) 13C: 133.95, 132.22, 131.68, 131.06, 130.32, 129.86, 122.93, 54.6 | | | |
| WZZL 811 | 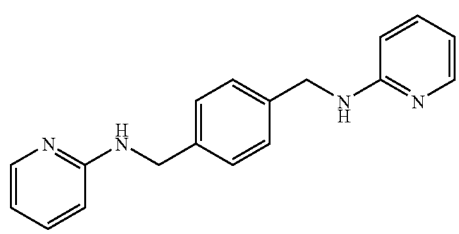 | DMSO: 400 Mz 1H: 7.93 (2H, dd, J = 4.8 Hz, 1.2 Hz); 7.34 (2H, td, J = 12.8 Hz, 2 Hz); 7.25 (4H, s); 6.96 (2H, t, J = 6 Hz), 6.45 (4H, m); 4.41 (4H, d, J = 6 Hz) 13C: 158.66, 147.53, 138.84, 136.60, 127.11, 111.67, 108.11, 43.93 | 192-194 | | 290.5 (290.4) |
| WZZL 811S | 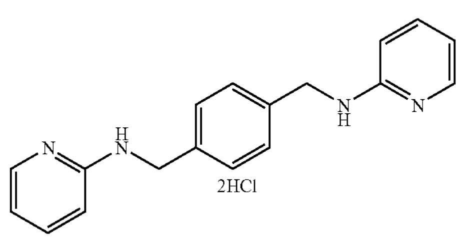 | D2O: 400 Mz 1H: 7.89 (2H, td, J = 8.4 Hz, 1.6 Hz); 7.79 (2H, d, J = 6.4 Hz); 7.43 (4H, s); 7.02 (2H, d, J = 8.4 Hz); 6.90 (2H, t, J = 6.4 Hz); | | $C_{18}H_{18}N_4$.2HCl C: 59.28 (59.51) H: 5.44 (5.55) N: 15.19 (15.4) Cl: 19.73 (19.52) | |

TABLE 1-continued

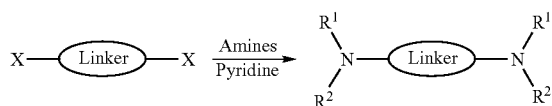

CHARACTERIZATION DATA FOR THE PREPARED COMPOUNDS

| Entry | Structure | $^1$HNMR/$^{13}$CNMR | M.p. (°C.) | Element Analysis Found (Calcd.) | MS (EI+): m/z (M$^+$) Found (Calcd.) |
|---|---|---|---|---|---|
| WZZL 811TS | [Structure: bis(pyridin-2-ylaminomethyl)benzene · 2TsOH] | DMSO: 1H (600 Mz): 9.07 (2H, br), 7.95 (4H, m); 7.49 (4H, d, J = 8.4 Hz); 7.40 (4H, s); 7.11 (6H, m); 6.90 (2H, t, J = 6 Hz); 4.58 (4H, d, J = 5.4 Hz); 3.68 (2H, br) 2.84 (4H, S) 13C (400 Mz): 152.56, 145.40, 143.49, 137.82, 136.26, 135.88, 128.12, 127.93, 125.48, 112.42, 44.56, 20.78 | | | |
| WZZL 811LTR | [Structure: bis(pyridin-2-ylaminomethyl)benzene · 1.75 tartaric acid] | D2O: 400 Mz 1H: 7.88 (2H, t, J = 9.2 Hz); 7.78 (2H, d, J = 6.4 Hz); 7.42 (4H, s); 7.02 (2H, d, J = 9.2 Hz); 6.89 (2H, t, J = 6.4 Hz); 4.62 (4H, s); 4.45 (3H, s) 13C: 173.18, 158.52, 147.25, 138.78, 136.79, 127.14, 111.69, 108.23, 72.16, 43.94 | | $C_{18}H_{18}N_4 \cdot 1.75 C_4H_6O_6$<br>C: 53.51 (54.3)<br>H: 5.35 (5.19)<br>N: 10.11 (10.13) | |
| WZ17 | [Structure: bis(pyridin-3-ylaminomethyl)benzene] | DMSO 1H (600 Mz): 7.96 (2H, D, J = 3 Hz); 7.73 (2H, dd, J = 3 Hz, 1.2 Hz); 7.32 (4H, s); 7.02 (2H, dd, J = 6 Hz, 4.2 Hz); 6.86 (2 Hz, dq, J = 6 Hz, 4.2 Hz, 1.8 Hz); 6.46 (2H, t, 6 Hz); 6.25 (4H, d, J = 6 Hz); 13C (400 Mz): 145.30, 138.79, 137.57, 136.17, 128.00, 124.21, 118.39, 46.42, | | | 290.4 (290.4) |

TABLE 1-continued

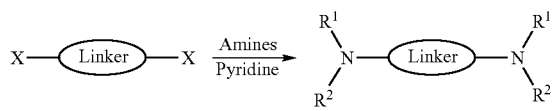

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ17S | (structure: pyridyl-NH-CH$_2$-C$_6$H$_4$-CH$_2$-NH-pyridyl · xHCl) | D2O: 600 Mz 1H: 7.92 (4H, m); 7.67 (4H, m); 7.42 (4H, s); 4.49 (4H, s) 13C: 147.21, 136.80, 128.30, 128.25, 127.85, 127.16, 124.26, 45.73 | | | |
| WZ18 | (structure: Ph-N(CH$_3$)-CH$_2$-C$_6$H$_4$-CH$_2$-N(CH$_3$)-Ph) | CDCl3: 400 Mz 1H: 7.24 (4H, m); 7.19 (4H, s); 6.75 (4H, m); 4.53 (4H, s); 3.02 (6H, s) 13C: 149.90, 137.83, 129.35, 127.16, 116.69, 112.52, 56.53, 38.69 | | | |
| WZ19 | (structure: Bn-NH-CH$_2$-C$_6$H$_4$-CH$_2$-NH-Bn) | DMSO 1H (600 Mz): 7.32 (8H, m); 7.28 (4H, s); 7.22 (2H, tt, J = 7.2 Hz, 1.2 Hz); 3.66 (4H, s); 3.65 (4H, s); 2.53 (2H, s) 13C (400 Mz): 140.44, 139.12, 128.49, 128.33, 128.26, 127.04, 53.24, 53.00 | | | |
| WZ19S | (structure: Bn-NH-CH$_2$-C$_6$H$_4$-CH$_2$-NH-Bn · 2HCl) | DMSO: 400 Mz 1H: 9.66 (4H, s); 7.59 (4H, s); 7.54 (4H, m); 7.43 (6H, m); 4.17 (4H, s); 4.13 (4H, s) | | | |
| WZ20 | (structure: 1,3,5-tris(phenylcarbamoyl)benzene) | DMSO 1H (600 Mz): 10.60 (3H, s); 8.71 (3H, s); 7.83 (6H, d, J = 7.8 Hz); 7.40 (6H, t, J = 7.8 Hz); 7.15 (3H, t, J = 7.2 Hz); 13C (400 Mz): 164.54, 138.94, 135.50, 129.79, 128.75, 124.00, 120.41 | 318-320 | | |

TABLE 1-continued
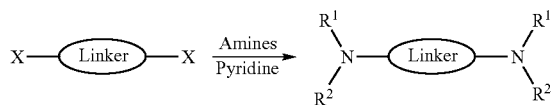
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ21 | 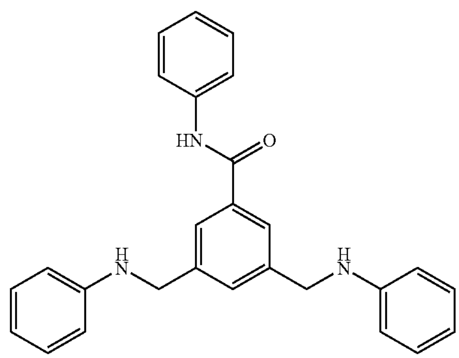 | CDCl3: 400 Mz 1H: 7.79 (3H, s); 7.62 (2H, d, J = 7.8 Hz), 7.58 (1H, s); 7.38 (2H, t, J = 7.8 Hz); 7.18 (5H, m); 6.75 (2H, td, J = 7.8 Hz, 1.2 Hz); 6.64 (4H, d, J = 6.6 Hz); 4.41 (4H, s) 13C: 165.97, 147.92, 141.07, 138.00, 135.79, 129.80, 129.46, 129.18, 125.03, 124.78, 120.52, 118.02, 113.15, 48.04 | | | 407.6 (407.5) |
| WZ22 | 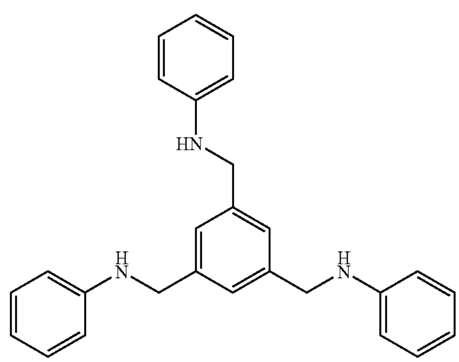 | CDCl3: 400 Mz 1H: 7.31 (3H, s); 7.18 (6H, m); 6.74 (3H, tt, J = 7.2 Hz, 0.8 Hz); 6.63 (6H, dm, J = 7.2 Hz); 4.32 (6H, s); 4.03 (3H, br) 13C: 148.24, 140.60, 129.44, 125.66, 117.84, 113.10, 48.42 | | | 393.5 (393.5) |
| WZ22S | 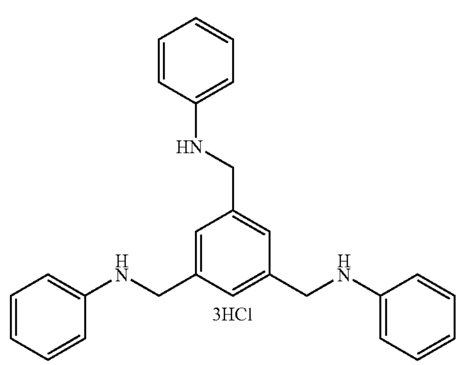 | D2O: 400 Mz 1H: 7.41 (9H, m); 7.16 (3H, s); 6.98 (6H, m); 4.51 (6H, S) | | | |

TABLE 1-continued
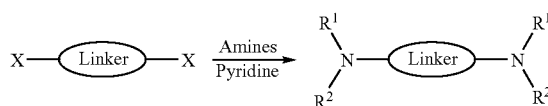
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ23 | 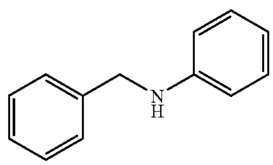 | CDCl3: 1H (600 Mz): 7.41 (4H, m); 7.32 (1H, t, J = 7.2 Hz); 7.22 (2H, t, J = 7.2 Hz); 6.76 (1H, td, J = 7.2 Hz, 1.2 Hz); 6.68 (2H, d, J = 7.2 Hz); 4.37 (2H, s); 4.06 (1H, br) 13C (400 Mz): 148.33, 139.62, 129.44, 128.81, 127.68, 127.39, 117.72, 113.01, 48.46 | 34-35 | | |
| WZ23S | 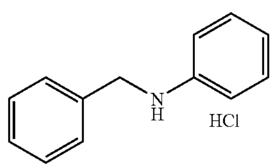 | CDCl3: 600 Mz 1H: 11.85 (2H, br); 7.30 (10H, m); 4.36 (2H, s) 13C: 134.37, 131.26, 129.86, 129.60, 129.58, 129.44, 128.87, 124.17, 56.18 | 211-212 | | |
| WZ24 | 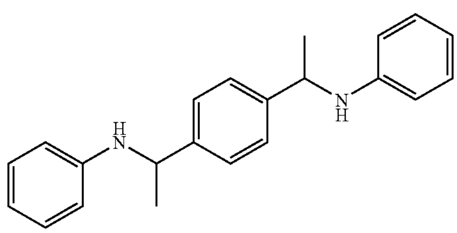 | CDCl3: 400 Mz 1H: 7.32 (4H, s); 7.11 (4H, t, J = 7.8 Hz); 6.66 (2H, tm, J = 7.2 Hz); 6.52 (4H, dm, J = 7.6 HZ); 4.48 (2H, m); 1.52 (3H, s); 1.50 (3H, s) 13C: 147.51, 143.93, 143.96, 129.30, 126.35, 117.35, 117.36, 113.43, 53, 31, 53.29, 25.01, 24.91 | | | |
| WZ25 | 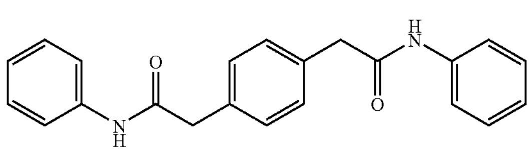 | DMSO 1H (600 Mz): 10.13 (2H, s); 7.58 (4H, d, J = 7.2 Hz); 7.28 (8H, t, J = 7.2 Hz); 3.61 (4H, s) 13C (400 Mz): 169.13, 139.23, 134.24, 129.05, 128.69, 123.18, 119.10, 42.95 | | | |

TABLE 1-continued
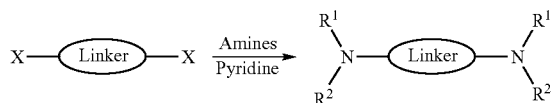
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ26 | 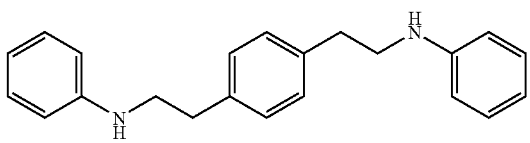 | CDCl3 1H (600 Mz): 7.20 (8H, m); 6.73 (2H, t, J = 7.2 Hz); 6.64 (4H, d, J = 7.2 Hz); 3.69 (2H, br); 3.42 (4H, t, J = 7.2 Hz); 2.92 (4H, t, J = 7.2 Hz) 13C (400 Mz): 148.21, 137.60, 129.49, 129.22, 117.87, 113.18, 45.24, 35.32 | | | 316.5 (316.4) |
| WZ27 | 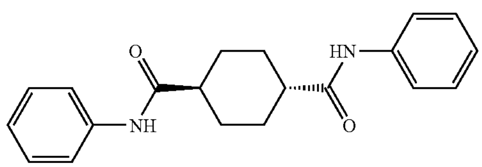 | DMSO 1H (600 Mz): 9.86 (2H, s); 7.60 (4H, d, J = 1.8 Hz); 7.28 (4H, t, J = 7.8 Hz); 7.02 (2H, t, J = 7.2 Hz); 2.35 (2H, br); 1.92 (4H, d, J = 6.6 Hz); 1.49 (4H, m) 13C (400 Mz): 173.95, 139.43, 128.64, 122.93, 119.04, 44.10, 28.29 | | | |
| WZ28 | 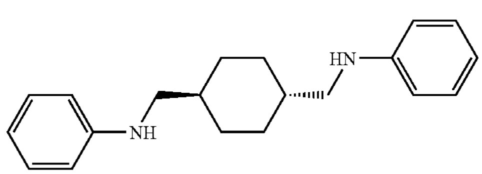 | CDCl3 1H (600 Mz): 7.18 (4H, m); 6.69 (2H, tt, 7.8 Hz, 0.6 Hz); 6.60 (4H, dd, J = 9.0 Hz, 0.6 Hz), s); 2.99 (4H, d, J = 6.6 Hz); 1.92 (4H, d, J = 6.6 Hz); 1.59 (2H, m); 1.03 (4H, m) 13C (400 Mz): 148.71, 129.45, 117.19, 112.82, 50.65, 37.94, 30.96 | | | 294.5 (294.4) |

TABLE 1-continued
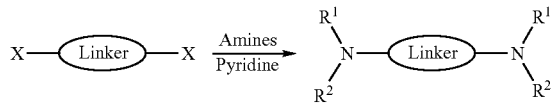
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ30 | 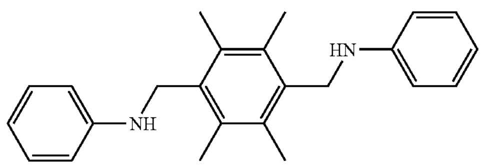 | CDCl3 1H (600 Mz): 7.26 (4H, m); 6.78 (2H, t, J = 7.8 Hz); 7.71 (4H, d, J = 7.8 Hz); 4.28 (4H, s); 3.48 (2H, br); 2.32 (12H, s) 13C (400 Mz): 148.44, 134.94; 134.31; 129.53; 117.67; 112.73; 43.70, 16.52 | | | 344.7 (344.5) |
| WZ31 | 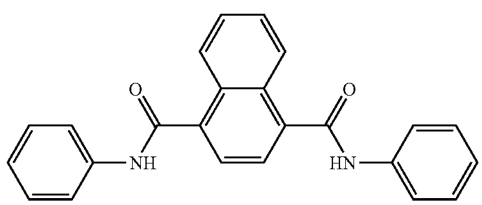 | DMSO: 400 Mz 1H: 10.66 (2H, q, J = 3.2 Hz); 8.24 (2H, m); 7.83 (6H, m); 6.67 (2H, q, J = 3.2 Hz); 7.40 (4H, t, J = 7.2 Hz); 7.15 (2H, t, J = 7.2 Hz) 13C: 166.84, 139.15, 136.65, 129.79, 128.78, 127.30, 125.57, 124.36, 123.88, 119.91, | | | |
| WZ32 | 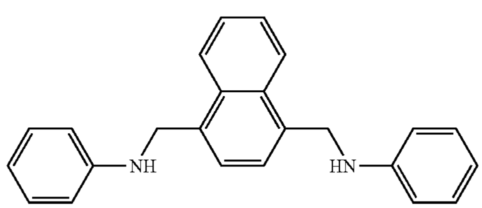 | CDCl3 1H (600 Mz): 8.15 (2H, q, J = 3.6 Hz); 7.58 (2H, q, J = 3.6 Hz); 7.51 (2H, s); 7.23 (4H, t, J = 7.2 Hz), 6.77 (2H, t, J = 7.2 Hz); 6.71 (4H, d, J = 7.2 Hz); 4.76 (4H, s); 4.11 (2H, br); 13C (400 Mz): 148.24, 134.54, 132.15, 129.56, 126.51, 126.02, 124.58, 117.97, 113.06, 46.75 | | | 338.5 (338.4) |

TABLE 1-continued
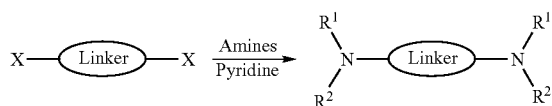
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ33 | 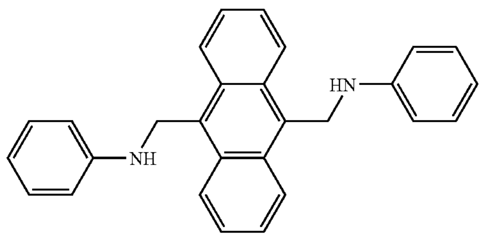 | CDCl3: 400 Mz 1H: 8.36 (4H, dd, J = 7.2 Hz, 3.2 Hz); 7.55 (4H, dd, J = 7.2 Hz, 7.32 (4H, t, J = 8.0 Hz); 6.85 (6H, m); 5.20 (4H, s); 3.98 (2H, br) 13C: 148.51, 130.86, 130.53, 129.68, 126.50, 125.13, 118.15, 112.94, 41.34 | | | |
| WZ34 | 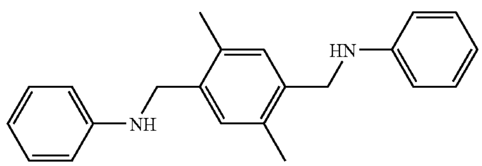 | CDCl3: 400 Mz 1H: 7.21 (6H, m); 6.76 (2H, t, J = 7.2 Hz); 6.67 (4H, d, J = 8.0 Hz); 4.24 (4H, s); 3.90 (2H, br); 2.32 (6H, s) 13C: 148.42, 136.25, 134.21, 130.85, 129.50, 117.82, 113.04, 46.44, 18.68 | | | 316.5 (316.4) |
| WZ35 | 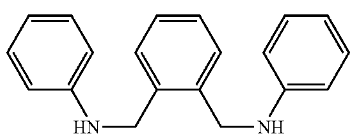 | CDCl3 1H (600 Mz): 7.44 (2H, m); 7.30 (2H, m); 7.19 (4H, tt, J = 6.6 Hz, 1.8 Hz); 6.77 (2H, t, J = 7.8 Hz); 6.68 (4H, d, J = 7.8 Hz); 4.60 (2H, br); 4.40 (4H, s) 13C (400 Mz): 148.13, 137.44, 129.56, 129.51, 128.17, 118.21, 113.41, 46.55 | | | |
| WZ35S | 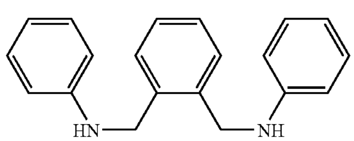 | DMSO: 400 Mz 1H: 8.25 (4H, br); 7.43 (2H, m); 7.27 (2H, m); 7.16 (4H, t, J = 7.8 Hz); 6.79 (6H, m); 4.39 (4H, s) | | | |

TABLE 1-continued

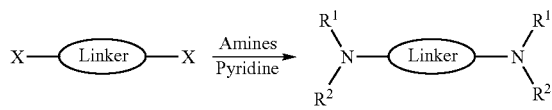

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ36 | HO-C6H4-NH-CH2-C6H4-CH2-NH-C6H4-OH | Acetone-d6: 400 Mz 1H: 7.39 (2H, s); 7.33 (4H, s); 6.61 (4H, m); 6.54 (4H, m); 4.86 (2H, m); 4.23 (4H, s) 13C: 149.83, 143.17, 140.13, 128.30, 116.61, 114.88, 49.11 | | | |
| WZ37 | NC-C6H4-NH-CH2-C6H4-CH2-NH-C6H4-CN | DMSO: 400 Mz 1H: 7.42 (4H, d, J = 9.2 Hz); 7.29 (4H, s); 7.26 (2H, t, J = 6.0 Hz); 6.63 (4H, d, J = 9.2 Hz); 4.30 (4H, d, J = 6.0 Hz) 13C: 152.04, 137.68, 133.31, 127.31, 120.54, 112.22, 95.88, 45.41 | | | 338.5 (338.4) |
| WZ38 | O2N-C6H4-NH-CH2-C6H4-CH2-NH-C6H4-NO2 | DMSO: 400 Mz 1H: 7.97 (4H, d, J = 9.2 Hz); 7.88 (2H, t, J = 5.6 Hz); 6.66 (4H, d, J = 9.2 Hz); 4.39 (4H, d, J = 5.6 Hz) 13C: 154.40, 137.42, 135.86, 127.42, 126.14, 45.50 | | | |
| WZ40 | pyrimidine-NH-CH2-C6H4-CH2-NH-pyrimidine | DMSO 1H (600 Mz): 8.24 (4H, d, J = 3.2 Hz); 7.63 (2H, t, J = 4.0 Hz); 7.21 (4H, s); 6.54 (2H, t, J = 3.2 Hz); 4.43 (4H, d, J = 4.0 Hz) 13C (400 Mz): 162.26, 157.95, 138.59, 126.86, 110.15, 43.62 | | | 292.4 (292.3) |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ41 | 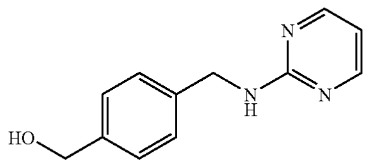 | CDCl3: 400 Mz 1H: 8.28 (2H, d, J = 4.8 Hz); 7.34 (4H, s); 6.56 (1H, t, J = 4.8 Hz); 5.46 (1H, br); 4.69 (2H, s); 4.62 (2H, d, J = 6.0 Hz); 2.08 (1H, s) 13C: 162.27, 157.93, 140.71, 138.74,126.74, 126.36, 110.14, 62.73, 43.65 | | | 215.2 (215.3) |
| WZ42 | 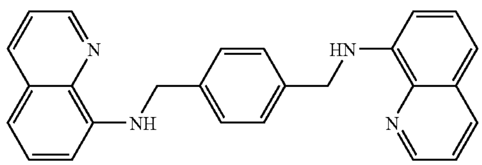 | CDCl3 1H (600 Mz): 8.73 (2H, dd, J = 3.6 Hz, 1.2 Hz); 8.08 (2H, dd, J = 7.8 Hz, 1.2 Hz), 7.43 (4H, s); 7.37 (4H, m); 7.07 (2H, d, J = 7.8 Hz); 6.67 (2H, d, J = 7.8 Hz); 6.6 (2H, t, J = 5.4 Hz); 4.57 (4H, d, J = 5.4 Hz) 13C (400 Mz): 147.14, 144.77, 138.43, 138.36, 136.23, 128.84, 127.98, 127.94, 121.63, 114.36, 105.32, 47.67 | | | |
| WZ43 | 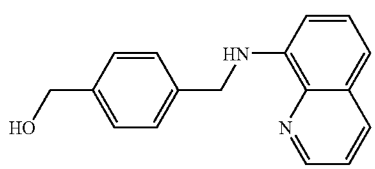 | CDCl3: 400 Mz 1H: 8.73 (1H, dd, J = 4.0 Hz, 1.6 Hz); 8.08 (1H, dd, J = 8.4 Hz, 2.0 Hz); 7.45 (2H, d, J = 7.6 Hz); 7.37 (4H, m); 7.07 (1H, dd, J = 8.4 Hz, 1.6 Hz); 6.63 (2H, d, J = 8.4 Hz); 4.70 (2H, d, J = 6.0 Hz); 4.58 (2H, d, J = 6.0 Hz); 1.66 (1H, 6.0 HZ) 13C: 147.14, 144.65, 139.97, 138.90, 138.37, 136.26, 128.82, 127.93, 127.76, 127.55, 121.61, 114.41, 105.39, 65.32, 47.60 | | | |

TABLE 1-continued

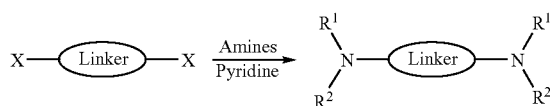

CHARACTERIZATION DATA FOR THE PREPARED COMPOUNDS

| Entry | Structure | $^1$HNMR/$^{13}$CNMR | M.p. (°C.) | Element Analysis Found (Calcd.) | MS (EI+): m/z (M$^+$) Found (Calcd.) |
|---|---|---|---|---|---|
| WZ48 | 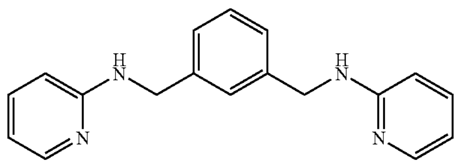 | CDCl3 1H (600 Mz): 8.10 (2H, d, J = 4.8 Hz); 7.40 (2H, tt, J = 6.0 Hz, 1.8 Hz); 7.37 (1H, s); 7.31 (2H, m); 7.28 (1H, s); 6.60 (2H, t, J = 6.0 Hz); 6.36 (2H, d, J = 8.4 Hz); 4.89 (2H, t, J = 6.0 Hz); 4.50 (4H, d, J = 6.0 Hz) 13C (400 Mz): 158.77, 148.44, 139.91, 137.67, 129.16, 126.64, 126.52, 113.42, 107.08, 46.42 | | | |
| WZ48S | 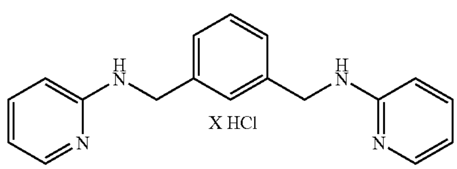 | D2O: 600 Mz 1H: 7.83 (2H, td, J = 9 Hz Hz, 1.2 Hz); 7.72 (2H, d, J = 6.6 Hz); 7.45 (1H, t, J = 7.8 Hz); 7.36 (2H, d, J = 7.8 Hz); 7.27 (1H, s); 6.94 (2H, d, J = 9.0 Hz); 6.87 (2H, t, J = 6.6 Hz); 4.63 (4H, s) | | | |
| WZ49 | 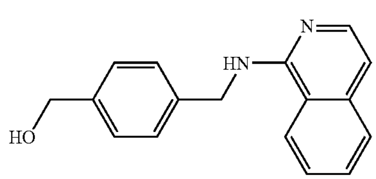 | CDCl3: 400 Mz 1H: 8.03 (1H, d, J = 6.0 Hz); 7.30 (2H, m), 7.61 (1H, td, J = 7.6 Hz, 1.2 Hz); 7.46 (3H, m); 7.37 (2H, m); 6.99 (1H, d, J = 5.6 Hz); 5.44 (1H, t, J = 6.0 Hz); 4.82 (2H, d, J = 6.0 Hz), 4.72 (2H, s), 1.79 (1H, s) 13C: 155.01, 141.51, 140.31, 139.06, 137.28, 129.96, 128.49, 127.60, 127.43, 126.17, 121.54, 118.25, 111.52, 65.30, 45.94 | | | |

TABLE 1-continued
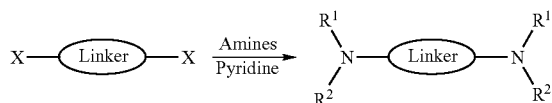
CHARACTERIZATION DATA FOR THE PREPARED COMPOUNDS
| Entry | Structure | $^1$HNMR/$^{13}$CNMR | M.p. (° C.) | Element Analysis Found (Calcd.) | MS (EI+): m/z (M$^+$) Found (Calcd.) |
|---|---|---|---|---|---|
| WZ50 | 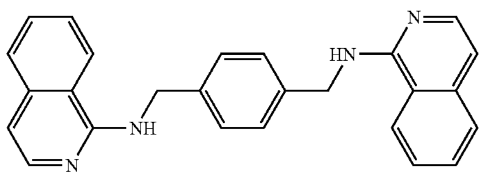 | CDCl3: 400 Mz 1H: 8.03 (2H, d, J = 6.0 Hz); 7.78 (2H, d, J = 8.0 Hz); 7.70 (2H, d, J = 8.0 Hz); 7.60 (2H, td, J = 7.6 Hz, 1.6 Hz); 7.45 (2H, td, J = 7.6 Hz, 1.6 Hz); 7.424 (4H, s); 6.98 (2H, d, J = 5.2 Hz); 5.57 (2H, br); 4.81 (4H, d, J = 5.2 Hz) 13C: 154.96, 141.33, 138.71, 137.26, 130.03, 128.59, 127.42, 126.22, 121.69, 118.28, 111.49, 45.90. | | | |
Additional compounds prepared and tested in cell assays to determine viral inhibition:
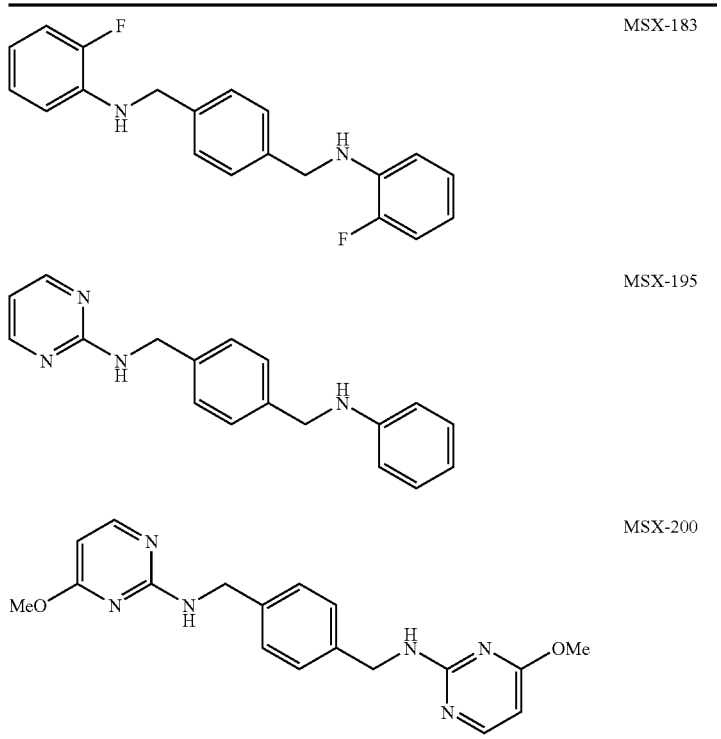

-continued
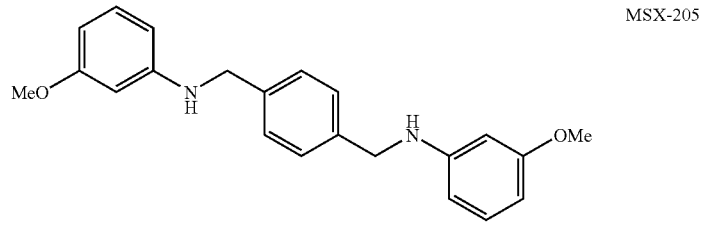
MSX-205
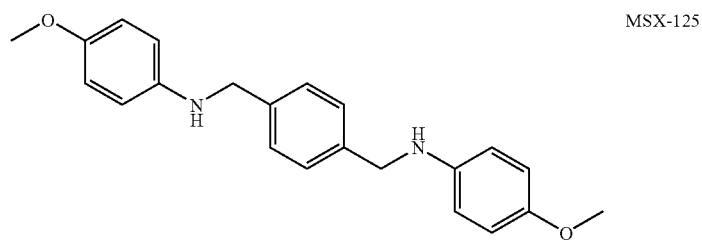
MSX-125
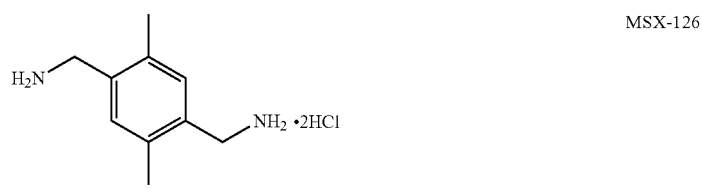
MSX-126
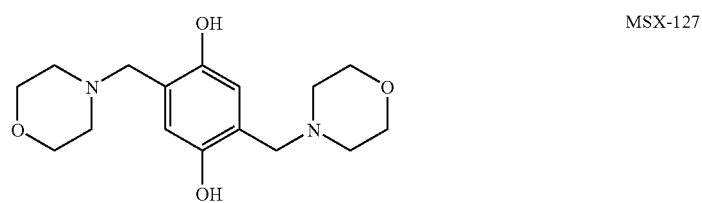
MSX-127
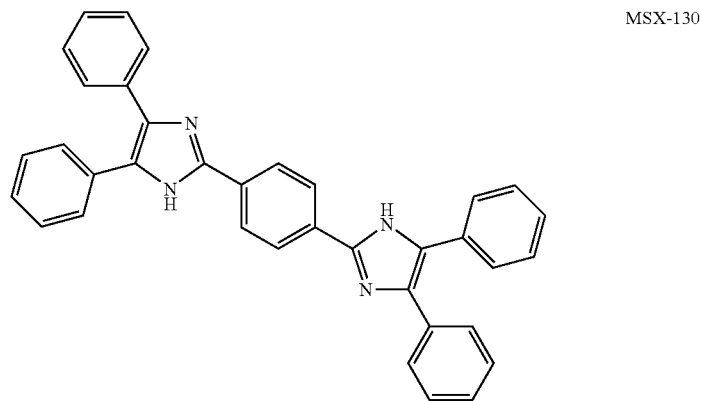
MSX-130
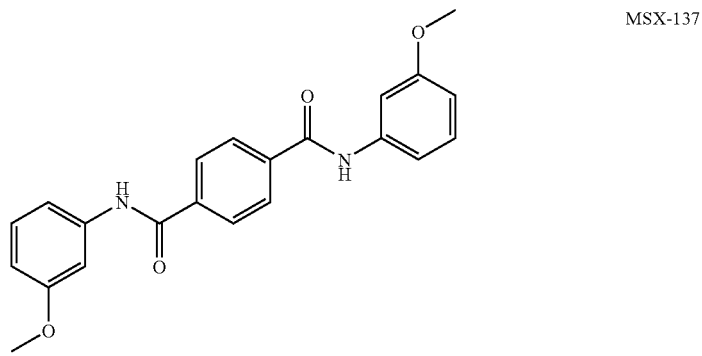
MSX-137

-continued
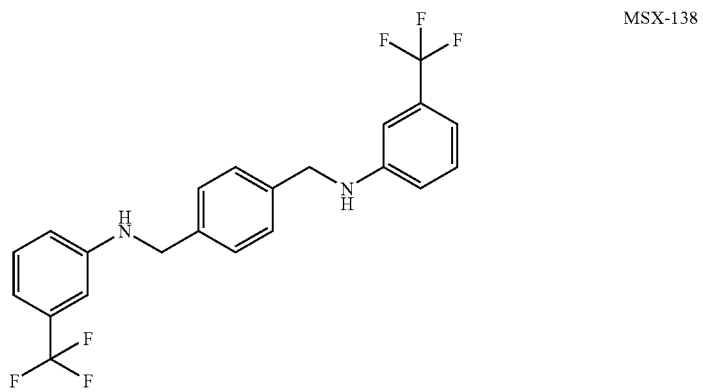
MSX-138
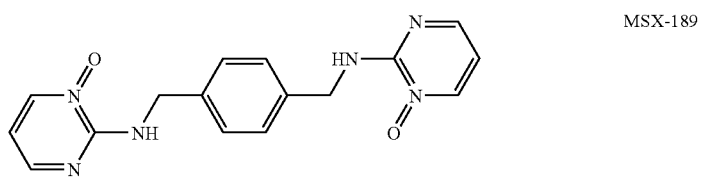
MSX-189
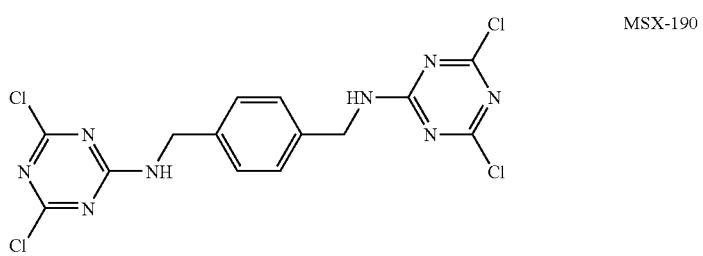
MSX-190
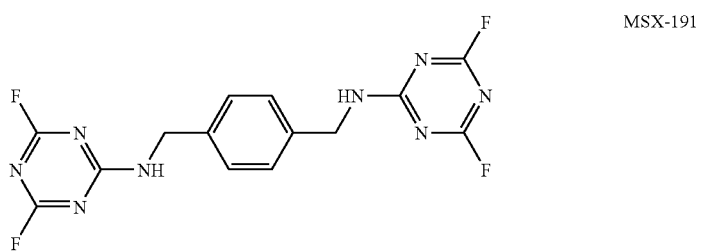
MSX-191
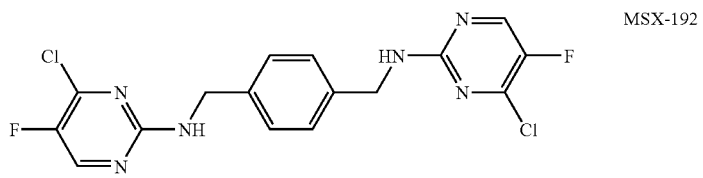
MSX-192
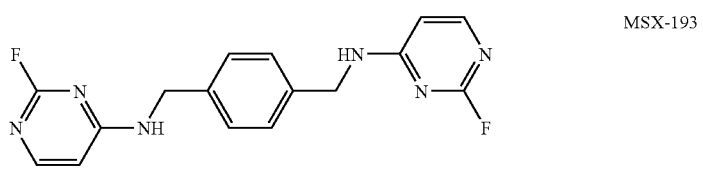
MSX-193

-continued
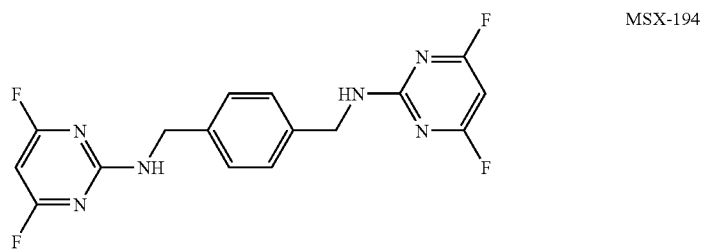 MSX-194
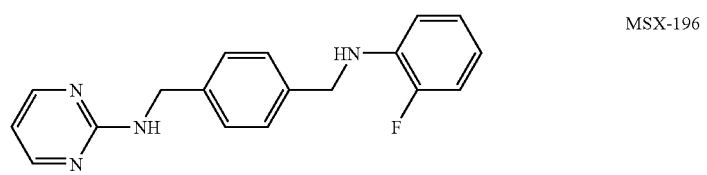 MSX-196
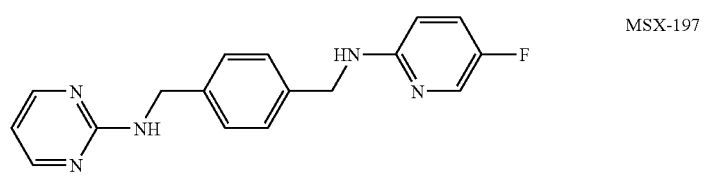 MSX-197
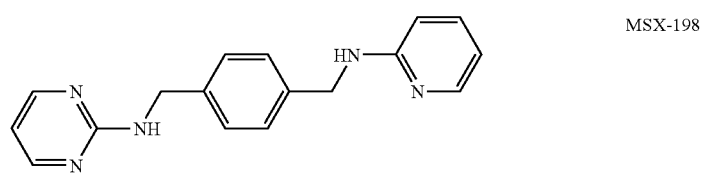 MSX-198
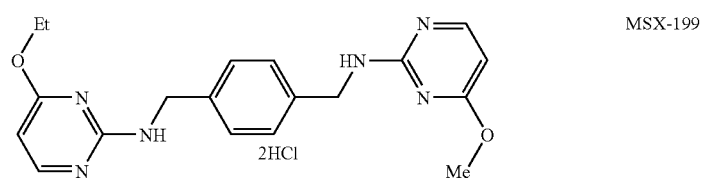 MSX-199
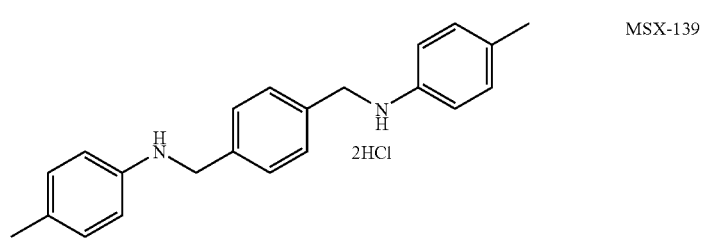 MSX-139
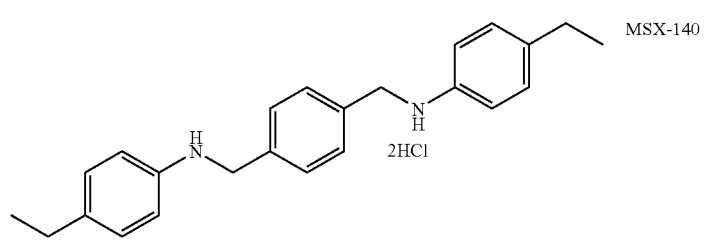 MSX-140
 MSX-141

-continued
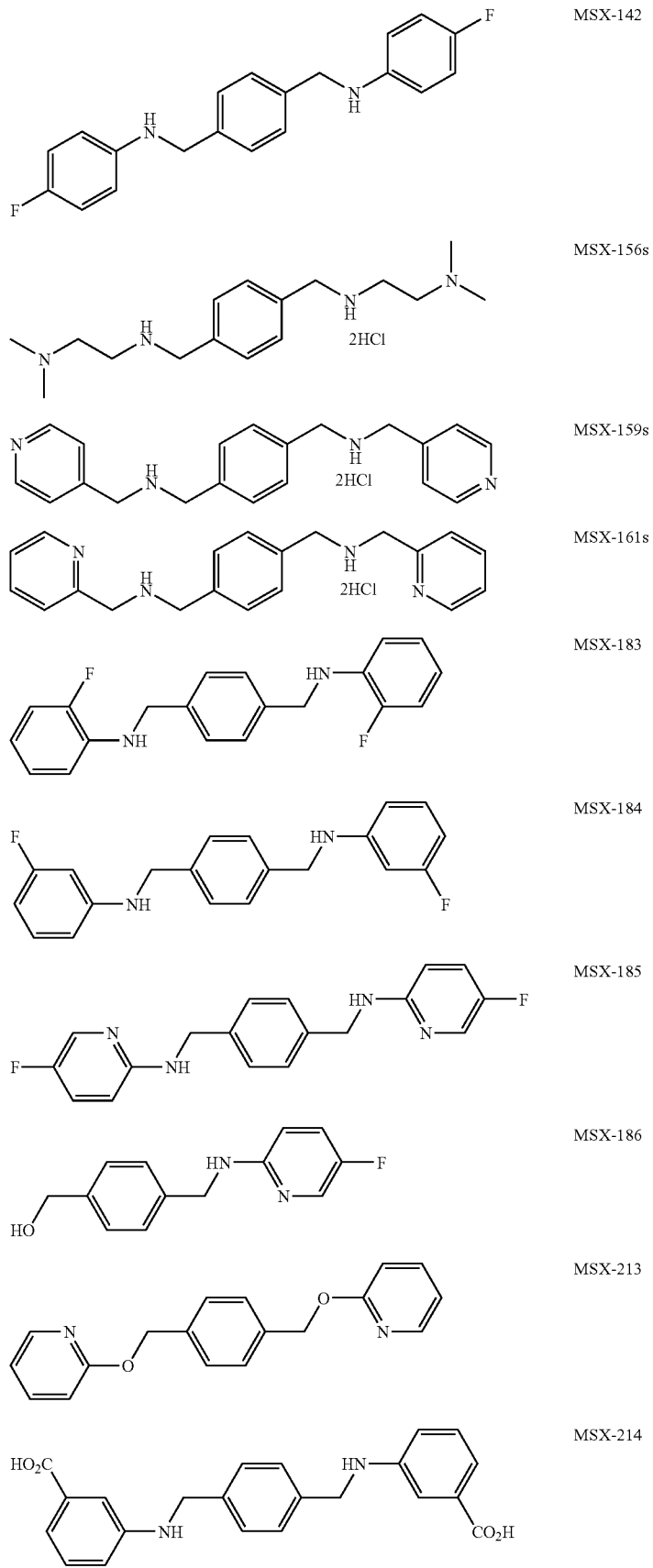

-continued
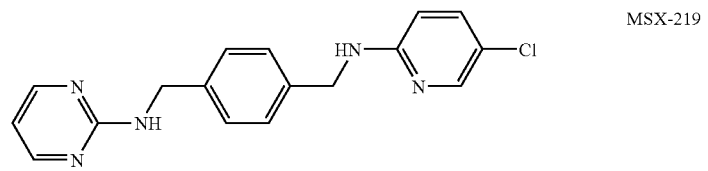
MSX-219
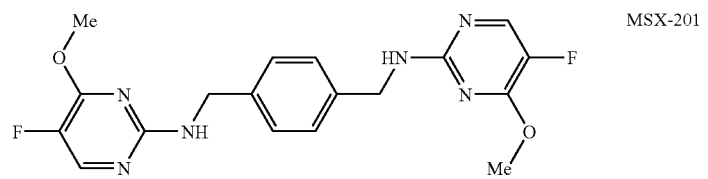
MSX-201
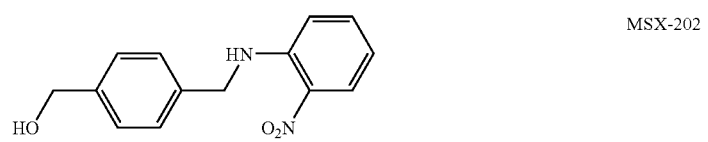
MSX-202
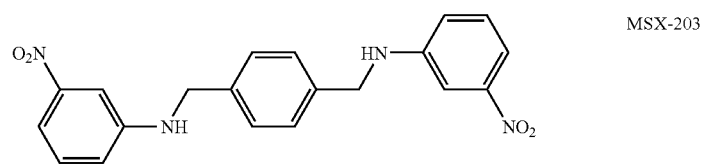
MSX-203
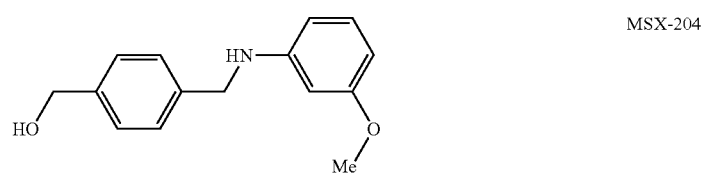
MSX-204
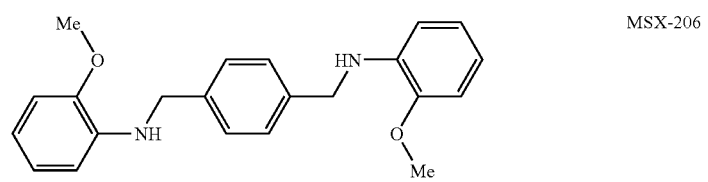
MSX-206
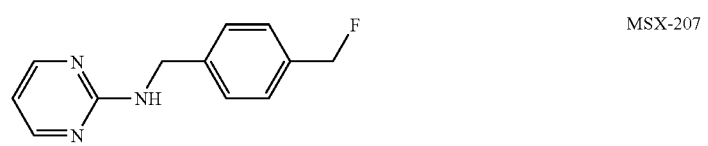
MSX-207
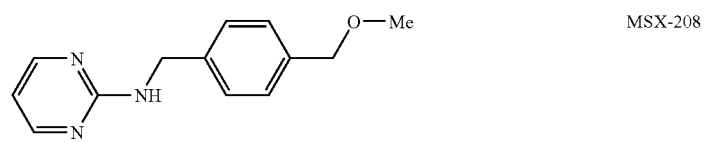
MSX-208
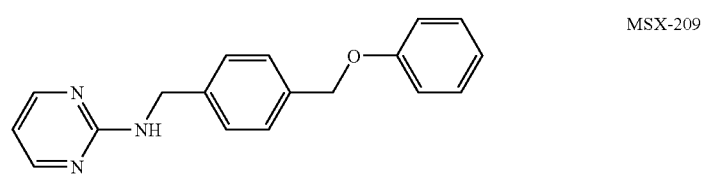
MSX-209

-continued

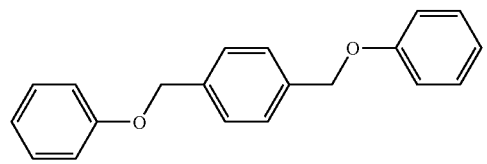
MSX-210

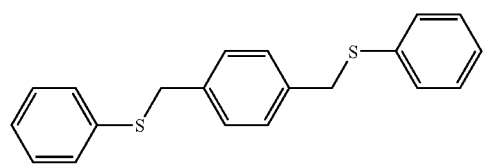
MSX-211

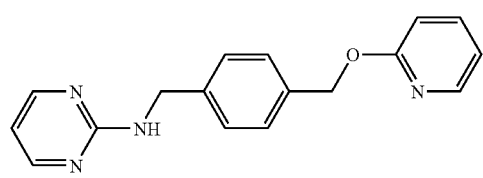
MSX-212

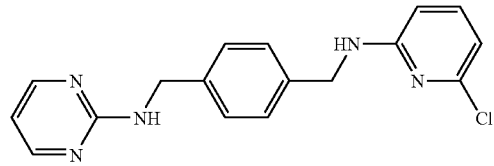
MSX-221

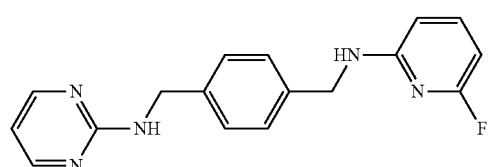
MSX-222

Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active compound can also be provided as a prodrug, which is converted into a biologically active form in vivo. A prodrug may be converted into the parent drug by various mechanisms, including enzymatic processes and metabolic hydrolysis. Harper, N.J. (1962) in Jucker, ed. *Progress in Drug Research*, 4:221-294; Morozowich et al. (1977) in E. B. Roche ed. *Design of Biopharmaceutical Properties through Prodrugs and Analogs*, APhA (Acad. Pharm. Sci.); E. B. Roche, ed. (1977) *Bioreversible Carriers in Drug in Drug Design, Theory and Application*, APhA; H. Bundgaard, ed. (1985) *Design of prodrugs*, Elsevier; Wang et al. (1999) *Curr. Pharm. Design.* 5(4):265-287; Pauletti et al. (1997) *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamejad (2000) in G. L. Amidon, P. I. Lee and E. M. Topp, Eds., *Transport Proc. Pharm. Sys.*, Marcell Dekker, p. 185-218; Balant et al. (1990) *Eur. J. Drug Metab. Pharmacokinet.*, 15(2): 143-53; Balimane and Sinko (1999) *Adv. Drug Deliv. Rev.*, 39(1-3):183-209; Browne (1997). *Clin. Neuropharm.* 20(1): 1-12; Bundgaard (1979) *Arch. Pharm. Chemi.* 86(1): 1-39; H. Bundgaard, ed. (1985) *Design of Prodrugs*, New York: Elsevier; Fleisher et al. (1996) *Adv. Drug Delivery Rev,* 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS Pharm Sci.*, 2(1): E6; Sadzuka Y. (2000) *Curr. Drug Metab.*, 1:3148; D. M. Lambert (2000) *Eur. J. Pharm. Sci.*, 11 Suppl 2:S1 5-27; Wang, W. et al. (1999) *Curr. Pharm. Des.*, 5(4):265.

The active compound can also be provided as a lipid prodrug. Nonlimiting examples of U.S. patents that disclose suitable lipophilic substituents that can be covalently incorporated into the compound or in lipophilic preparations, include U.S. Pat. No. 5,149,794 (Sep. 22, 1992,Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996,Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.).

Method of Treatment

The compounds described herein, are particularly useful for the treatment or prevention of a disorder associated with CXCR4 receptor binding or activation, and particularly a proliferative disorder, including cancer metastasis, modulated via CXCR4.

In one embodiment, a method of preventing metastases of a malignant cell is provided that includes administering a compound of at least one of Formula (I)-(XVII) to a host. The malignant cell can be a tumor cell. In certain embodiments, the compound can be provided to a host before treatment of a tumor. In a separate embodiment, the compound is provided to a patient that has been treated for cancer to reduce the likelihood of recurrence, or reduce mortality associated with a particular tumor. In another embodiment, the compound is administered to a host at high risk of suffering from a proliferative disease. Such high risk can be based, for example, on family history or on a history of exposure to known or presumed carcinogens.

Host, including humans suffering from, or at risk for, a proliferative disorder can be treated by administering an effective amount of the active compound or a pharmaceutically acceptable prodrug or salt thereof in the presence of a pharmaceutically acceptable carrier or diluent. The administration can be prophylactically for the prevention of a disorder associated with CXCR4 receptor activation, and particularly a proliferative disorder, including cancer metastasis. The active materials can be administered by any appropriate route, for example, orally, parenterally, intravenously, intradermally, subcutaneously, or topically, in liquid or solid form. However, the compounds are particularly suited to oral delivery.

A preferred dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester or prodrug, or by other means known to those skilled in the art.

In one particular embodiment, a method of preventing metastasis of a malignant cell is provided that includes contacting the cells with a compound of Formula XV, or a pharmaceutically acceptable salt, ester or prodrug thereof.

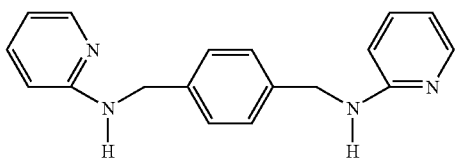

Formula XV

In a particular subembodiment, the compound is a salt of a compound of Formula XV, particularly a chloride salt.

In a separate embodiment, a method of treating proliferative disorders by administering a compound of Formulas (I)-(XVII) to a host in need of treatment is provided. In certain embodiments, the proliferative disorder is cancer, and in particular subembodiments, the disorder is a metastatic cancer.

The compounds of the invention can be administered to a host in need thereof to reduce the incidence of metastasis of a proliferative disorder, such as cancer. In particular embodiments, the cancer is breast cancer, brain tumor, pancreatic cancer, ovarian tumor, particularly an ovarian epithelial tumor, prostate cancer, kidney cancer, or non-small cell lung cancer.

In another embodiment, the invention provides a method of reducing neovascularization, particularly VEGF-dependent neocascularization, by contacting a cell with a compound of Formula (I)-(XVII). The cell can be in a host animal.

In a separate embodiment, a method for treating diseases of vasculature, inflammatory and degenerative diseases is provided including administering a compound of Formula (I)-(XVII) to a host. In one embodiment, a compound of Formula (I)-(XVII) is used to stimulate the production and proliferation of stem cells and progenitor cells.

The compounds can prevent or reduce the severity of diseases associated with CXCR4 activity, and in particular of proliferative diseases in any host. However, typically the host is a mammal and more typically is a human. In certain subembodiments the host has been diagnosed with a hyperproliferative disorder prior to administration of the compound, however in other embodiments, the host is merely considered at risk of suffering from such a disorder.

Pharmaceutical Compositions

In one embodiment, pharmaceutical compositions including at least one compound of Formulas (I)-(XVII) are provided. In certain embodiments, at least a second active compound is included in the composition. The second active compound can be a chemotherapeutic, particularly an agent active against a primary tumor.

Host, including humans suffering from, or at risk for, a proliferative disorder can be treated by administering an effective amount of a pharmaceutical composition of the active compound.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient. Ideally the active ingredient should be administered to achieve peak plasma concentrations of the active compound of from about 1 uM to 100 mM or from 0.2 to 700 uM, or about 1.0 to 10 uM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or antiviral compounds, or with additional chemotherapeutic agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation. If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Combination and Alternation Therapy

In one embodiment, the compounds described herein are administered in combination or alternation with another active compound.

In one embodiment, the active compound is a compound that is used as a chemotherapeutic. The compound provided in combination or alternation can, for example, be selected from the following list:

| | | | |
|---|---|---|---|
| 13-cis-Retinoic Acid | 2-Amino-6-Mercaptopurine | 2-CdA | 2-Chlorodeoxyadenosine |
| 5-fluorouracil | 5-FU | 6-TG | 6-Thioguanine |
| 6-Mercaptopurine | 6-MP | Accutane | Actinomycin-D |
| Adriamycin | Adrucil | Agrylin | Ala-Cort |
| Aldesleukin | Alemtuzumab | Alitretinoin | Alkaban-AQ |
| Alkeran | All-transretinoic acid | Alpha interferon | Altretamine |
| Amethopterin | Amifostine | Aminoglutethimide | Anagrelide |
| Anandron | Anastrozole | Arabinosylcytosine | Ara-C |
| Aranesp | Aredia | Arimidex | Aromasin |
| Arsenic trioxide | Asparaginase | ATRA | Avastin |
| BCG | BCNU | Bevacizumab | Bexarotene |
| Bicalutamide | BiCNU | Blenoxane | Bleomycin |
| Bortezomib | Busulfan | Busulfex | C225 |
| Calcium Leucovorin | Campath | Camptosar | Camptothecin-11 |
| Capecitabine | Carac | Carboplatin | Carmustine |
| Carmustine wafer | Casodex | CCNU | CDDP |
| CeeNU | Cerubidine | cetuximab | Chlorambucil |
| Cisplatin | Citrovorum Factor | Cladribine | Cortisone |
| Cosmegen | CPT-11 | Cyclophosphamide | Cytadren |
| Cytarabine | Cytarabine liposomal | Cytosar-U | Cytoxan |
| Dacarbazine | Dactinomycin | Darbepoetin alfa | Daunomycin |
| Daunorubicin | Daunorubicin hydrochloride | Daunorubicin liposomal | DaunoXome |
| Decadron | Delta-Cortef | Deltasone | Denileukin diftitox |
| DepoCyt | Dexamethasone | Dexamethasone acetate | dexamethasone sodium phosphate |

-continued

| | | | |
|---|---|---|---|
| Dexasone | Dexrazoxane | DHAD | DIC |
| Diodex | Docetaxel | Doxil | Doxorubicin |
| Doxorubicin liposomal | Droxia | DTIC | DTIC-Dome |
| Duralone | Efudex | Eligard | Ellence |
| Eloxatin | Elspar | Emcyt | Epirubicin |
| Epoetin alfa | Erbitux | Erwinia L-asparaginase | Estramustine |
| Ethyol | Etopophos | Etoposide | Etoposide phosphate |
| Eulexin | Evista | Exemestane | Fareston |
| Faslodex | Femara | Filgrastim | Floxuridine |
| Fludara | Fludarabine | Fluoroplex | Fluorouracil |
| Fluorouracil (cream) | Fluoxymesterone | Flutamide | Folinic Acid |
| FUDR | Fulvestrant | G-CSF | Gefitinib |
| Gemcitabine | Gemtuzumab ozogamicin | Gemzar | Gleevec |
| Gliadel wafer | Glivec | GM-CSF | Goserelin |
| granulocyte colony stimulating factor | Granulocyte macrophage colony stimulating factor | Halotestin | Herceptin |
| Hexadrol | Hexalen | Hexamethylmelamine | HMM |
| Hycamtin | Hydrea | Hydrocort Acetate | Hydrocortisone |
| Hydrocortisone sodium phosphate | Hydrocortisone sodium succinate | Hydrocortone phosphate | Hydroxyurea |
| Ibritumomab | Ibritumomab Tiuxetan | Idamycin | Idarubicin |
| Ifex | IFN-alpha | Ifosfamide | IL-2 |
| IL-11 | Imatinib mesylate | Imidazole Carboxamide | Interferon alfa |
| Interferon Alfa-2b (PEG conjugate) | Interleukin-2 | Interleukin-11 | Intron A (interferon alfa-2b) |
| Iressa | Irinotecan | Isotretinoin | Kidrolase |
| Lanacort | L-asparaginase | LCR | Letrozole |
| Leucovorin | Leukeran | Leukine | Leuprolide |
| Leurocristine | Leustatin | Liposomal Ara-C | Liquid Pred |
| Lomustine | L-PAM | L-Sarcolysin | Lupron |
| Lupron Depot | Matulane | Maxidex | Mechlorethamine |
| Mechlorethamine Hydrochlorine | Medralone | Medrol | Megace |
| Megestrol | Megestrol Acetate | Melphalan | Mercaptopurine |
| Mesna | Mesnex | Methotrexate | Methotrexate Sodium |
| Methylprednisolone | Meticorten | Mitomycin | Mitomycin-C |
| Mitoxantrone | M-Prednisol | MTC | MTX |
| Mustargen | Mustine | Mutamycin | Myleran |
| Mylocel | Mylotarg | | Navelbine |
| Neosar | Neulasta | Neumega | Neupogen |
| Nilandron | | | |
| Nilutamide | Nitrogen Mustard | Novaldex | Novantrone |
| Octreotide | Octreotide acetate | Oncospar | Oncovin |
| Ontak | Onxal | Oprevelkin | Orapred |
| Orasone | Oxaliplatin | Paclitaxel | Pamidronate |
| Panretin | Paraplatin | Pediapred | PEG Interferon |
| Pegaspargase | Pegfilgrastim | PEG-INTRON | PEG-L-asparaginase |
| Phenylalanine Mustard | Platinol | Platinol-AQ | Prednisolone |
| Prednisone | Prelone | Procarbazine | PROCRIT |
| Proleukin | Prolifeprospan 20 with Carmustine implant | Purinethol | Raloxifene |
| Rheumatrex | Rituxan | Rituximab | Roveron-A (interferon α-2a) |
| Rubex | Rubidomycin hydrochloride | Sandostatin | Sandostatin LAR |
| Sargramostim | Solu-Cortef | Solu-Medrol | STI-571 |
| Streptozocin | Tamoxifen | Targretin | Taxol |
| Taxotere | Temodar | Temozolomide | Teniposide |
| TESPA | Thalidomide | Thalomid | TheraCys |
| Thioguanine | Thioguanine Tabloid | Thiophosphoamide | Thioplex |
| Thiotepa | TICE | Toposar | Topotecan |
| Toremifene | Trastuzumab | Tretinoin | Trexall |
| Trisenox | TSPA | VCR | Velban |
| Velcade | VePesid | Vesanoid | Viadur |
| Vinblastine | Vinblastine Sulfate | Vincasar Pfs | Vincristine |
| Vinorelbine | Vinorelbine tartrate | VLB | VM-26 |
| VP-16 | Vumon | Xeloda | Zanosar |
| Zevalin | Zinecard | Zoladex | Zoledronic acid |
| Zometa | | | |

In one embodiment, the compounds of the invention are administered in combination with another active agent. The compounds can also be administered concurrently with the other active agent. In this case, the compounds can be administered in the same formulation or in a separate formulation. There is no requirement that the compounds be administered in the same manner. For example, the second active agent can be administered via intravenous injection while the compounds of the invention may be administered orally. In another embodiment, the compounds of the invention are administered in alternation with at least one other active compound. In a separate embodiment, the compounds of the invention are administered during treatment with a chemotherapeutic, such as, for example, an agent listed above, and administration of the compounds of the invention is continued after cessation of administration of the other active compound. The compound may be administered for at least a month, at least two months, at least four, six, seven, eight, nine, ten, eleven, twelve months or more to reduce incidence of metastasis.

The compounds of the invention can be administered prior to or after cessation of administration of another active compound. In certain cases, the compounds may be administered before beginning a course of treatment for primary tumors, for example. In a separate embodiment, the compounds can be administered after a course of chemotherapy to reduce recurrence of metastatic tumors.

Diseases

The compounds described herein, are particularly useful for the treatment or prevention of a disorder associated with CXCR4 receptor binding or activation, and particularly a proliferative disorder, including cancer metastasis. However, multiple other diseases have been associated with CXCR4 receptor signaling. In addition, the compounds can be used to treat disorders of abnormal cell proliferation generally, examples of which include, but are not limited to, types of cancers and proliferative disorders listed below.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. *Nature*, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) *The New England Journal of Medicine*, 322:1277-1289), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of proliferative disorders which can be the primary tumor that is treated, or which can be the site from which metastasis is inhibited or reduced, include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Specific types of diseases include Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphorria, Adult Lymphocytic Leukemia, Adult Non-Hodgkin's Lymphoma, Adult Primary Liver Cancer, Adult Soft Tissue Sarcoma, AIDS-Related Lymphorria, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphorria, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalanic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancer, Esophageal Cancer, Ewing's Sarcoma and Related Tumors, Exocrine Pancreatic Cancer, Extraeranial Germ Cell Tumor, Extragonadal Germ Cell Tumor, Extrahepatie Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatie Occult Primary Squamous Neck Cancer, Metastatic-Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyrigeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethial Cancer, Uterine Cancer, Uterine Sarcoma, Vaginal Cancer, Visual Pathway and Hypothalarruc Glioma, Vulvar Cancer, Waldenstroin's Macroglobulinemia, Wilm's Tumor, and any other hyperproliferative disease located in an organ system listed above.

Hyperplastic disorders include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblastic, promyelocytic, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, Sarcomas and, carcinomas such as fibrosarcoma, myxosarcoma, fiposarcoma, chondrosarcoma, osteogenic sarcoma, chordoma, anglosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, a method for the treatment of, prevention of, or reduced severity of, age-related macular degeneration (ARMD) and other pathogenic states involving macular retinal pigment epithelial (RPE) cells including administering at least one compound described herein is provided.

CXCR4 plays a crucial role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) *J. Immunol.* 165: 4372-4278). CXCR4 receptor expression on human retinal pigment epithelial cells from the blood-retina barrier leads to chemokine secretion and migration in response to stromal cell-derived factor 1a. *J. Immunol.* 200; 165: 4372-4278). The level of CXCR4 mRNA expression increases upon stimulation with IL-1β or TNFα (Dwinell, et al. (1999) *Gastroenterology.* 117: 359-367). RPE cells also migrated in response to SDF-1α indicating that SDF-1α/CXCR4 interactions may modulate the affects of chronic inflammation and subretinal neovascularization at the RPE site of the blood-retina barrier. (Crane I J, Wallace C A, McKillop-Smith S, Forrester J V. CXCR4 receptor expression on human retinal pigment epithelial cells from the blood-retina barrier leads to chemokine secretion and migration in response to stromal cell-derived factor 1a. *J. Immunol.* 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) *Ophthalmology.* 1995; 102: 1206-1211).

In a separate embodiment, a method for the treatment of, prevention of, or reduced severity of inflammatory disease states, neovascularization, and wound healing including administering at least one compound described herein is provided.

Vascular endothelial cells express a multitude of chemokine receptors, with CXCR4 being particularly prominent (Gupta, et al. (1998) *J Biol Chem.* 273: 4282; Volin, et al. (1998) *Biochem Biophys Res Commun.* 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number, of epithelial cell lines derived from various other tissues. (Murdoch, et al. (1998) *Immunology.* 98(1): 36-41). Unlike with endothelial cells, CXCR4 is the only chemokine receptor expressed on epithelial cells. The receptor may have a functional role in epithelial pathology. Whether CXCR4 participates in inflammatory responses remains unclear. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium. (Murdoch, et al. (1999) *Immunology.* 98(1): 3641).

In addition, the invention is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the invention is directed to methods of treating animal subjects, in particular, veterinary and human patients, who are defective in white blood cell (WBQ 8 count, or who would benefit from elevation of WBC levels using the compounds disclosed herein. Moreover, the invention is directed to methods of effecting regeneration of cardiac tissue in a subject in need of such regeneration using the disclosed compounds.

The compounds of the invention may be used for the treatment of diseases that are associated with immunosuppression such as individuals undergoing chemotherapy, radiation therapy, enhanced wound healing and burn treatment, therapy for autoinimune disease or other drug therapy (e.g., corticosteroid therapy) or combination of conventional drugs used in the treatment of autoinimune diseases and graft/transplantation rejection, which causes immunosuppression; immunosuppression due to congenital deficiency in receptor function or other causes; and infectious diseases, such as parasitic diseases, including but not limited to helminth infections, such as nematodes (round invention thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the invention targets a broad spectrum of conditions characterized by a deficiency in white blood cell count, or which would benefit from elevation of said WBC count.

The term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocytemacrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols. "Stem" cells are less differentiated forms of progenitor cells. Typically, such cells are often positive for CD34. Some stem cells do not contain this marker, however. In general, CD34+ cells are present only in low levels in the blood, but are present in large numbers in bone marrow.

The compounds of the invention may be administered as sole active ingredients, as mixtures of various compounds of Formula (I)-(XVII), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoictin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The binding of SDF-1 to CXCR4 has also been implicated in the pathogenesis of atherosclerosis (Abi-Younes et al. Circ. Res. 86, 131-138 (2000)), renal allograft rejection (Eitner et al. Transplantation 66, 1551-1557 (1998)), asthma and allergic airway inflammation (Yssel et al. Clinical and Experimental AllerD; 28, 104-109 (1998); *J* 1777771 unol. 164, 59355943 (2000); Gonzalo et al. J limmunol. 165, 499-508 (2000)), Alzheimer's disease (Xia et al. J. Neurovirologv 5, 3241 (1999)) and Arthritis (Nanlci-et al. J Immunol. 164, 5010-5014 (2000)).

Process for Identification of CXCR4 Antagonists

In a separate embodiment, a process for screening potential drug candidates is provided. The process includes providing a labeled peptide-based CXCR4 antagonist that has a detectable signal when bound to a CXCR4 receptor; contacting a CXCR4 receptor with at least one test molecule at a known concentration to form a test sample; contacting the test sample with the peptide-based antagonist; separately, contacting the peptide-based antagonist to a sample not including any test molecule to form a control sample; and comparing the signal from the test sample to the signal from the control sample. In a specific sub-embodiment, the peptide-based antagonist is derived from TN14003 (described in PCT Publication No. WO 04/087068 to Emory University). In a further subembodiment, the antagonist is labeled with a biotin molecule and the signal is elicited when the biotin-labeled antagonist is contacted with a streptavadin-conjugated signal molecule.

The signal elicited by binding of the CXCR4 antagonist and the receptor can be a fluorescent signal. In one embodiment, the signal is elicited when a second, accessory molecule is added, such as, for example, a fluorescent molecule bound to a molecule that binds the labeled antagonist molecule. In one embodiment, the antagonist molecule is labeled with biotin, and the accessory molecule is a fluorescently labeled streptavadin molecule.

The peptide-based antagonist is typically a molecule with high affinity for the receptor. In one embodiment, the molecule is derived from the "T140" peptide antagonists. In a specific embodiment, the antagonist is TN14003 (described in PCT Publication No. WO 04/087068 to Emory University). The receptor is typically expressed in a cell line. The process can be performed as a dose-response curve. In this embodiment, the test compound is incubated with the receptor at varying concentrations and the signal elicited after binding of the labeled-antagonist is measured and compared to control, as well as to each other.

EXAMPLES

Example 1

Peptide-based CXCR4 Antagonist, TN14003, is a Novel-imaging Probe Specific for CXCR4

Initially, experiments were performed to verify that TN14003 binds to the predicted SDF-1 binding sites on the CXCR4 receptor. In these studies, MDA-MB-231 cells were incubated in the absence (FIGS. 1A, B) or presence (FIGS. 1A, C) of 400 ng/ml of SDF-1α for 10 min, and then fixed in ice-cold acetone. Immunofluorescence of the biotin-labeled TN14003 was negative in both membrane and cytosol in the cells pretreated with SDF-1α for 10 min (FIGS. 1A, C).

The utility of the biotinylated TN14003 as a probe of CXCR4 was explored coupled with immunofluorescence staining of cultured breast cancer cells and paraffin-embedded tissues from breast cancer patients. MDA-MB-231 had high levels of mRNA and protein for CXCR4 as shown by Northern blots and Western blots relative to MDA-MB-435 (FIG. 1B). When the biotinylated TN14003 was used to stain the two cell types, the high CXCR4-expressing MDA-MD-231 cells were brightly stained (FIG. 1C left), whereas the low CXCR4-expressing MDA-MB435 was less (FIG. 1C right) consistent with the low surface CXCR4 expression in these cells.

Immunofluorescence staining with the biotinylated TN14003 on cancer patients' paraffin-embedded tissue sections demonstrated that TN14003 could be used to detect CXCR4 receptors on tumor cells from the archived paraffin-embedded tissue sections (FIG. 1D). A total of 41 patient tissues provided by Avon Tissue Bank for Translational Genomics Research at Grady Memorial Hospital in Atlanta, Ga., were stained and 0 out of 4 normal breast tissues, 9 out of 12 Ductal Carcinoma in situ (DCIS), and 23 out of 25 node-positive cases were positive for CXCR4. Many samples carrying the diagnoses of DCIS already acquired CXCR4 over-expression (FIG. 1D).

Example 2

TN14003 is a More Potent Inhibitor of CXCR4-associated Signaling than AMD3100

Figure 2:
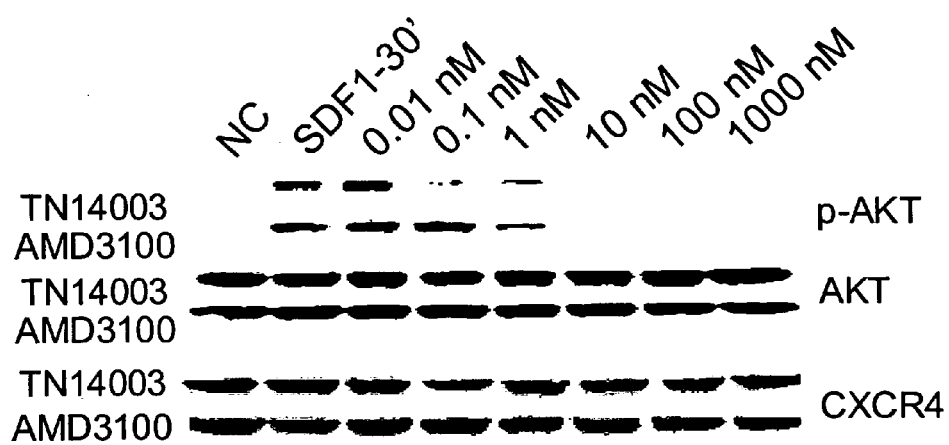
FIG. 2 is an image of a western blot showing phosphorylation of Akt. Incubating MDA-MB-231 cells with 100 ng/ml of SDF-1 for 30 min stimulated phosphorylation of Akt. This activation was blocked with TN 14003 or AMD3100 in a dose-dependent manner.

CXCR4/SDF-1 interaction activates PI3K/Akt and Ras/Raf/MEK/Erk pathways in a $G\alpha_i$ protein (PTX-sensitive)-dependent manner. Experiments were conducted to determine the effect of blocking CXCR4/SDF-1 interaction by either TN14003 or AMD3100 at different concentrations (0, 0.01, 0.1, 1, 10, 100, 1000 nM) on phosphorylations of Akt and Erk1/2 signaling. Incubating cells with 100 ng/ml of SDF-1 for 30 minutes activated Akt. Akt activation was blocked by either sub-nano molar concentration of TN14003 or a few nano molar AMD3100 (FIG. 2). Erk1/2 phsophorylation was attenuated in the presence of sub-nano molar concentration of TN14003 or 100 nM AMD3100 (data not shown). However, the increase in Erk1/2 phosphorylation by SDF-1 was not significant as the increase in Akt phosphorylation. The results demonstrate that TN14003 is more potent than AMD3100 in inhibiting CXCR4-mediated signaling. Treating cells with SDF-1, TN14003, or AMD3100 did not affect CXCR4 protein levels.

Example 3

Knock Down of CXCR4 by siRNA Blocks Metastasis in the Lung

RNA interference technology, silencing targeted genes in mammalian cells, has become a powerful tool for studying gene function. Two different siRNA duplexes of CXCR4 (Genbank Accession no. NM_003467), siRNA1 (sense, 5'-UAAAAUCUUCCUGCCCACCdTdT-3') (SEQ. I.D. No. 1) and siRNA2 (sense, 5'-GGAAGCUGUUG-GCUGAAAAdTdT-3') (SEQ. I.D. No. 2) were designed and purchased from Dharmacon (Lafayette, Colo.). The non-specific control siRNA duplexes were purchased from Dharmacon with the same GC content as CXCR4 siRNAs (42%, D001206-10).

Figure 3:
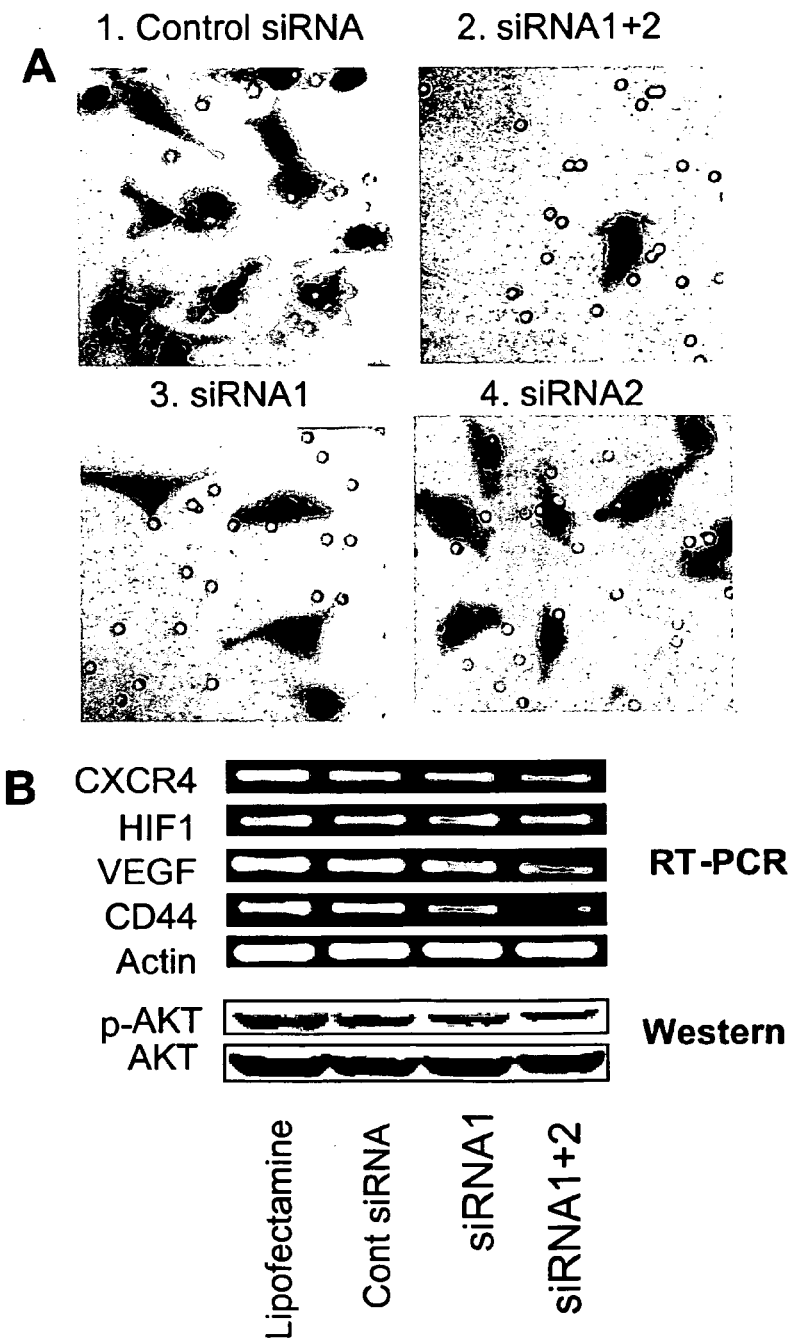
FIG. 3 shows images of stained cells and blots showing invasion of MDA-MB-231 cells transfected with CXCR4 siRNAs. A: H&E staining of invasion of MDA-MB-231 cells transfected with control siRNA, siRNA1 alone, or siRNA2 alone in matrigel invation assay. The invasiveness of MDA-MB-231 cells transfected with siRNA 1+2, siRNA1 and siRNA2 relative to the control are 16% (P<0.0003), 39% (P<0.0014) and 51% (P<0.0026) respectively. B: VEGF, HIF-1 and CD44 mRNA levels. Actin was used as a loading control.

Lowering CXCR4 mRNA levels by siRNAs inhibited CXCR4/SDF-1-mediated invasion as measured by a matrigel invasion assay. The CXCR4 ligand, SDF-1 (400 ng/ml) was added to the lower chamber to attract CXCR4-positive breast cancer cells to migrate through the matrigel. The invasion of MDA-MB-231 cells transfected with siRNA1 decreased to 39±4% of the control cells, 51±8% with siRNA2, and only 16±6% with both siRNA1+2 (FIG. 3A). FIG. 3B shows that lowering CXCR4 influenced the mRNA levels of VEGF and CD44 without affecting mRNA levels of HIF-1α.

To determine whether lowering CXCR4 levels in MDA-MB-231 cells blocks lung metastasis in the experimental animal model, MDA-MB-231 cells were transfected with various combination of CXCR4 siRNAs and injected into the female SCID mice through the tail vein twice weekly intravenously by themselves (without liposome) following the injection of tumor cells (Groups 2-4). Forty-five days after the tumor cell injection, all animals in the control group (Group 1) developed lung metastases. In contrast, only one animal in Group 2 developed metastases and these were barely visible. A representative picture of lungs in FIG. 4A demonstrated grossly cystic lung micro-metastasis in the control group. On the other hand, three representative pictures of lungs from three treated groups showed significantly fewer visible lung metastases, most notably in Groups 2 and 3. The H&E staining of the lung tissues from Group 2 showed the morphology of normal lung, while that from the control group showed invading tumor cells (FIG. 4A).

Figure 4:
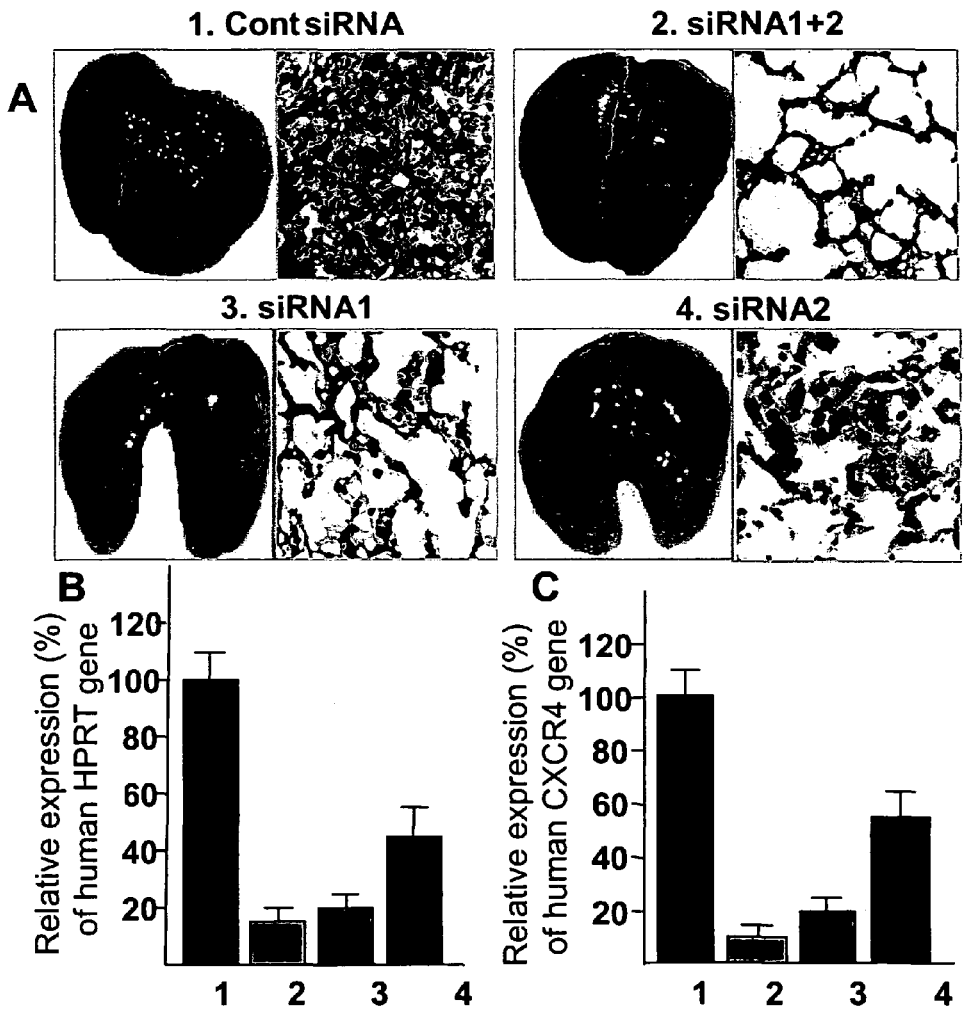
FIG. 4 shows images of cells and lungs, as well as graphs of the effect of CXCR4 siRNAs on inhibition of breast cancer metastasis in vivo. A: The photographs of lungs and their H&E stainings of one representative from each group. B: The average real-time PCR (RT-PCR) of hHPRT using primers that only recognize human cells from siRNA-treated groups relative to that of control group. 1: Group 2; 2: Group 2; 3: Group 3; 4: Group 4. C: The percentage of human CXCR4 average expression level of each treated group is relative to that of control group.
Figure 5:
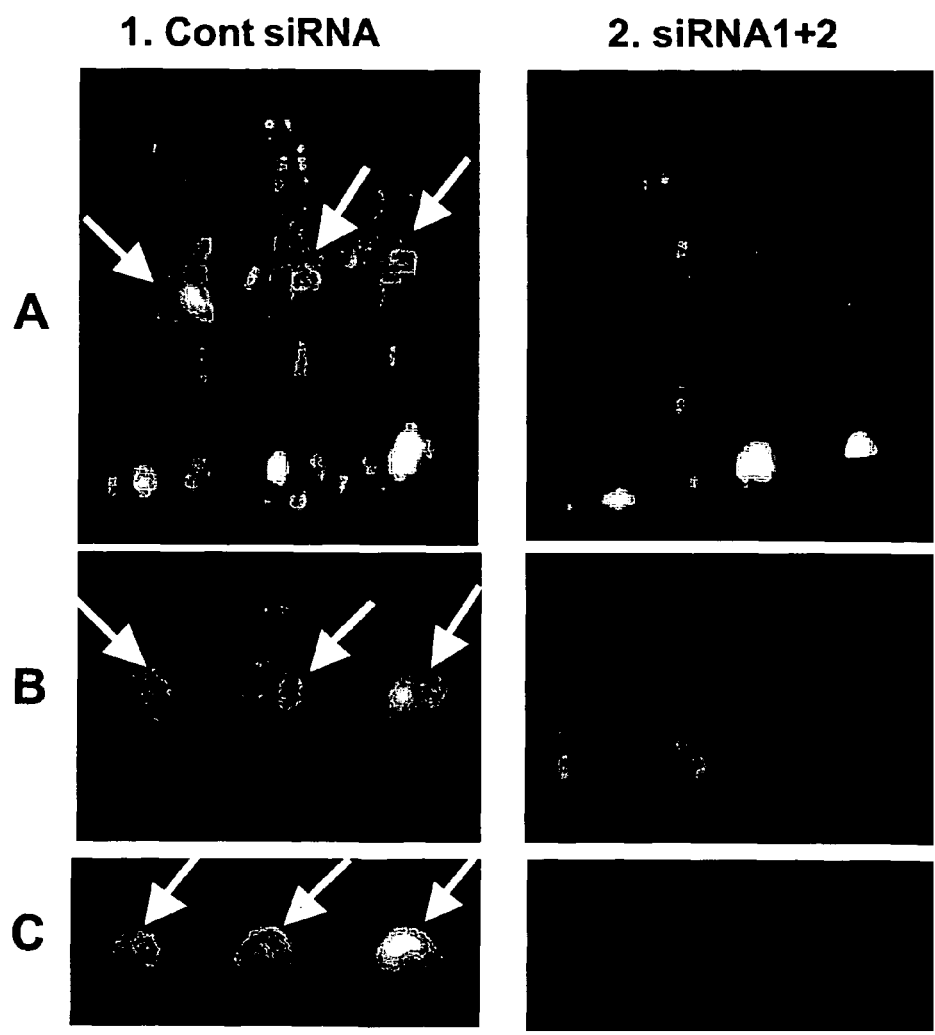
FIG. 5 shows Representative images of FDG-PET of animals in Group 1 (control siRNA) and Group 2 (siRNA1+2) indicating the effect of CXCR4 siRNAs on inhibition of breast cancer metastasis in vivo. A: The maximum intensity projection of 6 representative mice from Group 1 (left 3 mice) and Group 2 (right 3 mice). B: Coronal sectional images from the lung area from the same animals in A. C: The transaxial sectional images from the lung area from the same animals in A.

These results were further confirmed by semi-quantitative real-time RT-PCR using primers for the human housekeeping gene hHPRT that do not cross-react with its mouse counterpart (FIG. 4B). Real-time RT-PCR analyses showed high expression of hHPRT mRNA in metastasis-infiltrated lungs of the SCID mice in the control group. The expression levels of human HRPT in the lungs of mice in Groups 2 and 3 were significantly lower than that of control group (FIG. 4B). There was high CXCR4 expression in the control group mouse lungs and much lower CXCR4 expression in the lungs of the treated group mice (FIG. 4C). MicroPET imaging with FDG was utilized to detect lung metastases in mice in Groups 1 and 2. FIG. 5 shows representative FDG-PET images confirming lung metastasis in the control group and significantly fewer lung metastases in Group 2. FIG. 5A is a maximum intensity projection (three-dimensional) generated from three representative mice in Group 1 (control). The chest area is significantly brighter in each mouse of the control group (left) than any of the mice in the siRNA1+2 treated group (right). The high FDG-uptake can also be seen in the bladder due to the secretion of FDG. FIGS. 5B and 5C are selected coronal and transaxial section images, respectively. The maximum standardized uptake values ($SUV_{max}$) of the lung area in FIG. 5 were 8.6, 7.1, 9.3, 2.2, 2.5, and 2.1. Collectively, these images show that FDG uptake is much higher in lungs from the control group (left) than siRNA1+2 treated group (right), which correlates with increased lung metastases in the control group than the siRNA1+2 treated group.

Example 4

VEGF Promotor Regulation by CXCR4 and HIF-1α

Figure 6:
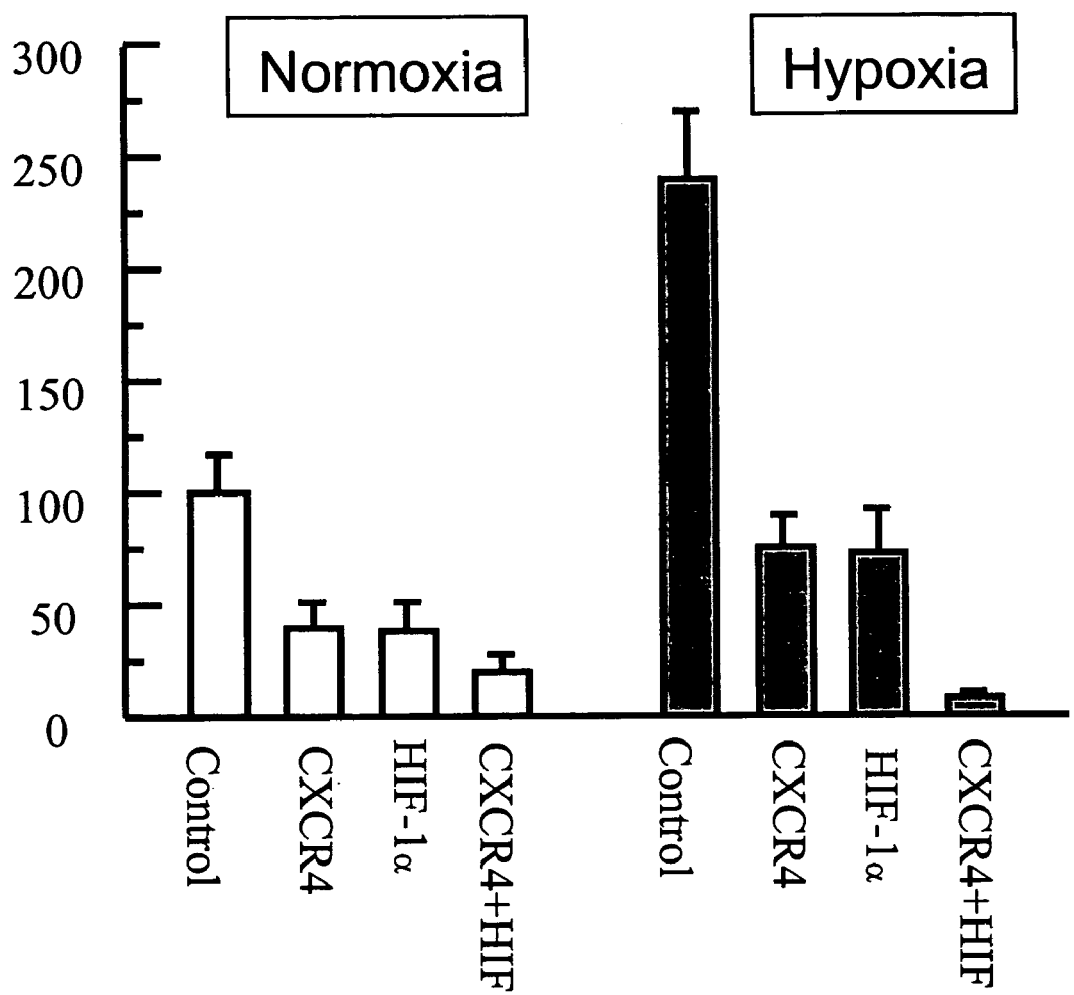
FIG. 6 is a graph of HRE activity. The graph shows that HRE-Luc MB-231 cells have moderately high HRE activity in normoxia that can be suppressed by either CXCR4 siRNA or HIF-1 siRNA. HRE activity increase 2.5 fold in hypoxia that can also be suppressed by either CXCR4 siRNA or HIF-1 siRNA.

To determine whether lowering CXCR4 levels might affect VEGF transcription compared to HIF-1α the hypoxia-reporting luciferase/LacZ plasmid from Dr. Van Meir's laboratory was used as a reporter system to detect hypoxia-responsive element (HRE) of VEGF promoter activity (Post, D. E. and Van Meir, E. G. (2001) *Gene Ther* 8: 1801-1807). The sequence of HIF-1α siRNA was 5'-UUCAAGWUGGAA-UUGGUAGdTdT-3'. (SEQ. I.D. No. 3)Pooled cell clones were created with MDA-MB-231 cells stably transfected with this plasmid (called HRE-Luc MB-231). Unexpectedly, HRE activity in normoxia was moderately high in MDA-MB-231 cells that have high CXCR4 levels in normoxia (FIG. 6, left), which was not observed in other cell lines with low CXCR4 and HIF-1 levels (LN229, U87, 9L, and MDA-MB-435). This moderately high HRE activity in MDA-MB-231 cells was suppressed by CXCR4 siRNA or HIF-1α siRNA. The HRE activity significantly decreased with the combination treatment of CXCR4 siRNA and HIF-1α siRNA for 48 hours. As expected, the HRE activity increased 2.5-fold by hypoxia treatment (1% oxygen and 5% $CO_2$ in nitrogen). This elevated HRE activity was again suppressed by siRNA for CXCR4 or HIF-1α (FIG. 6, right).

Example 5

Screening of Novel Anti-CXCR4 Small Molecule by Competition Assay Using Biotin-labeled TN14003 (Peptide-based)

The molecular dynamic simulations of the rhodopsin-based homology model of CXCR4 shows that AMD3100 is a weak partial agonist because it interacts with CXCR4/SDF-1 binding by two aspartic acids while the peptide-based CXCR4 antagonist, T140 (similar to TN14003) strongly binds the SDF-1 binding site of CXCR4 in extracellular domains and regions of the hydrophobic core proximal to the cell surface (Trent, et al. (2003) *J Biol Chem* 278: 47136-47144). This structural information was used to create a library of compounds with multiple nitrogens throughout the molecular framework, but structurally different from AMD3100.

Figure 7:
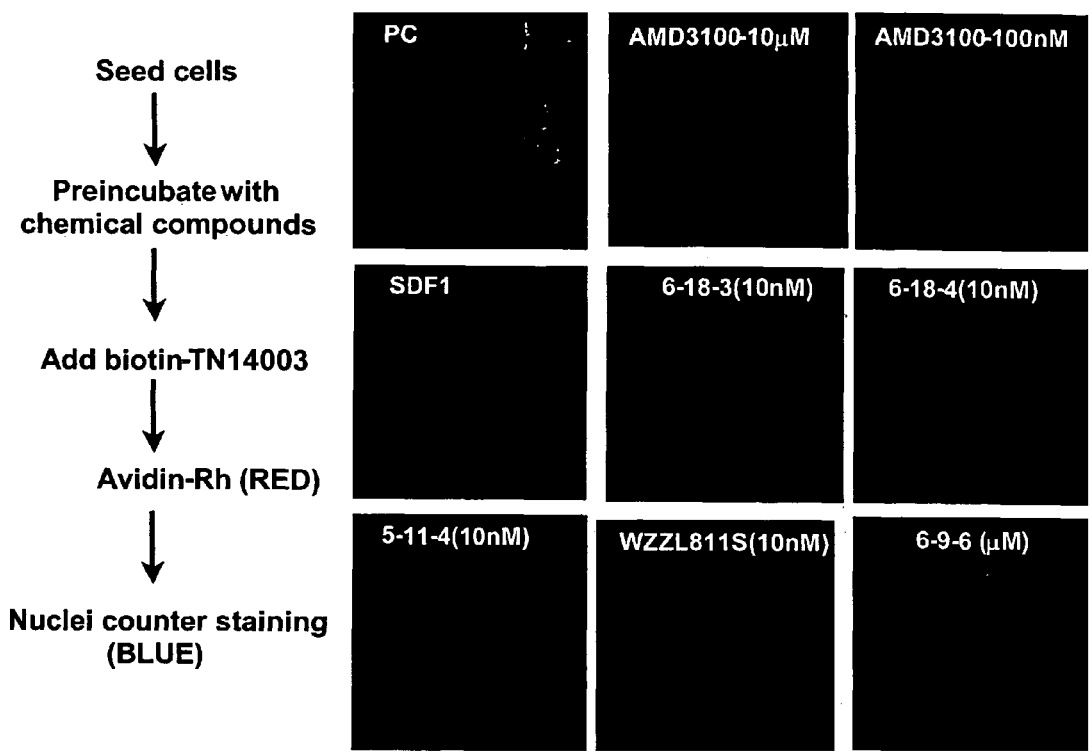
FIG. 7 is images of fluorescence micrographs of cells showing a drug screen methodology utilizing biotin-labeled TN14003 as a reporter.
Figure 8:
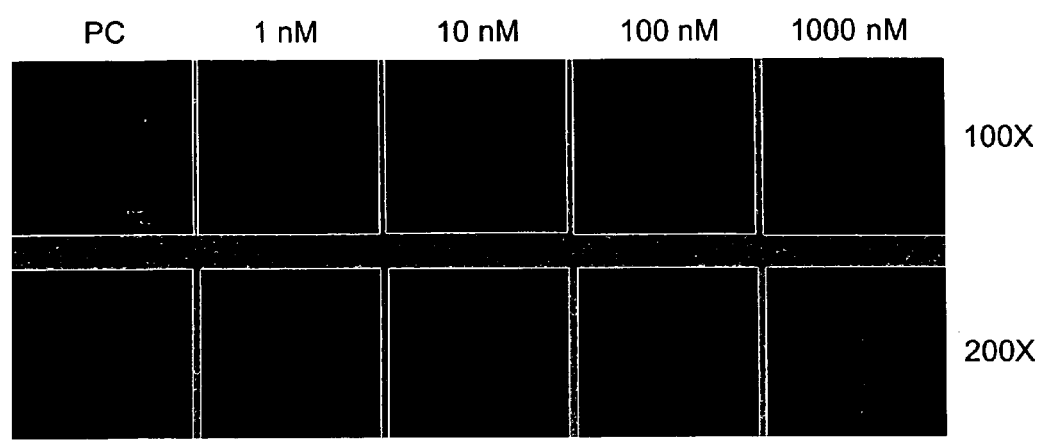
FIG. 8 is images of fluorescens micrographs of stained cells. Biotin-labeled TN14003 was used to detect CXCR4 protein from the cells pre-incubated with various concentrations of WZZL811S. Results indicate that IC50 of WZZL811S is less than 1 nM.
Figure 9:
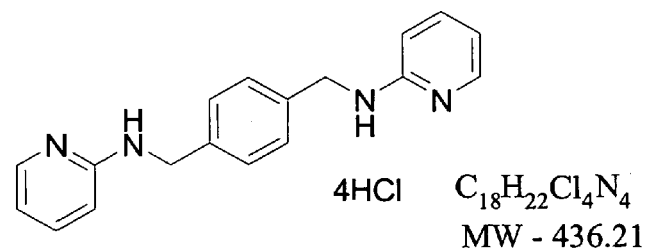
FIG. 9 is a representation of the chemical structure of WZZL811S.

Using biotin-labeled TN14003 along with streptavidin-conjugated rhodamine allowed a determination of the binding efficiency of these chemicals to the SDF-1 binding site of CXCR4 on tumor cells and compared it to AMD3100-SDF-1 interactions (FIG. 7). The cells incubated with compounds with high affinities for the ligand-binding site showed only blue nuclei staining, whereas compounds with low affinity resulted in both CXCR4 in red (rhodamine) and blue nuclei staining. Cells were pre-incubated with different concentrations of AMD3100. The results indicated that 10 µM concentration was needed for AMD3100 to compete against biotin-labeled TN14003. On the other hand, some candidate compounds were as potent as TN14003 at very low concentrations. Therefore, one of these compounds, WZZL811S, was selected to study its therapeutic potential based on potency and low toxicity to cells (FIG. 9). FIG. 8 shows the binding affinity of WZZL811S to the ligand-binding site (approximately the same as TN14003 binding site) of CXCR4 on tumor cells at nano-molar concentration. WZZL811 S did not decrease cell viability of MDA-MB-231 cells even at 100 µM (the highest concentration tested).

Example 6

Figure 10:
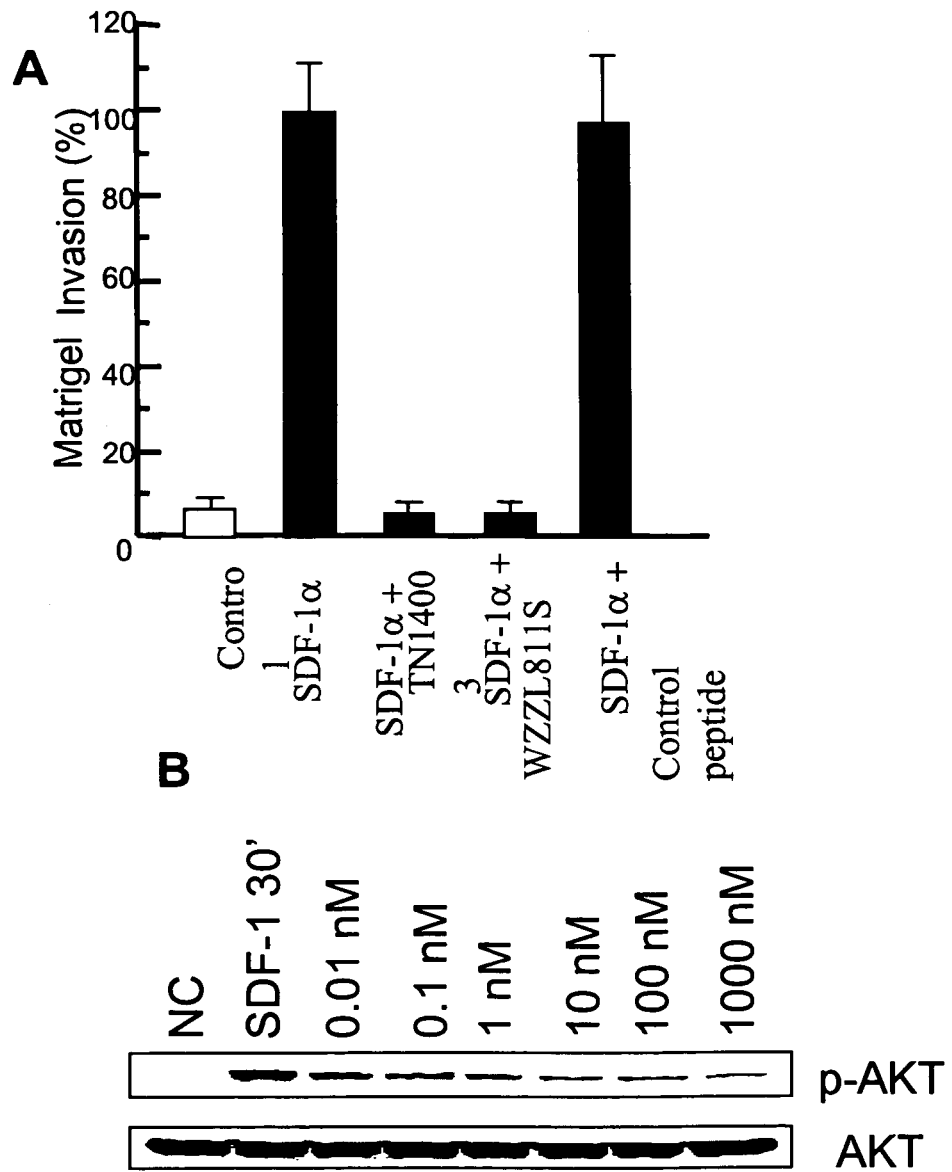
FIG. 10 is a graph and representative blot of matrigel invasion and Akt phosphorylation in cells. A: Inhibition of CXCR4/SDF-1 mediated invasion of MDA-MB-231 in vitro by WZZL811S. CXCR4/SDF-1 mediated invasion of MDA-MB-231 was blocked either by 2 nM of TN14003 or WZZL811S. B: Incubating MDA-MB-231 cells with 100 ng/ml of SDF-1 for 30 min stimulated phosphorylation of Akt that, blocked by WZZL811S in a dose-dependent manner

WZZL811S Inhibits CXCR4/SDF-1-mediated Matrigel Invasion and CXCR4/SDF-1-mediated Akt Activation WZZL811S was tested in a matrigel invasion assay to determine whether it can inhibit CXCR4/SDF-1-mediated invasion. As shown in FIG. 10A, WZZL811S was as potent as TN14003 in blocking SDF-1-induced invasion at the same concentration (2 nM). FIG. 10B shows that WZZL811S blocked SDF-1/CXCR4-induced Akt phosphorylation in a dose-dependent manner.

Example 7

Animal Models

Figure 11:
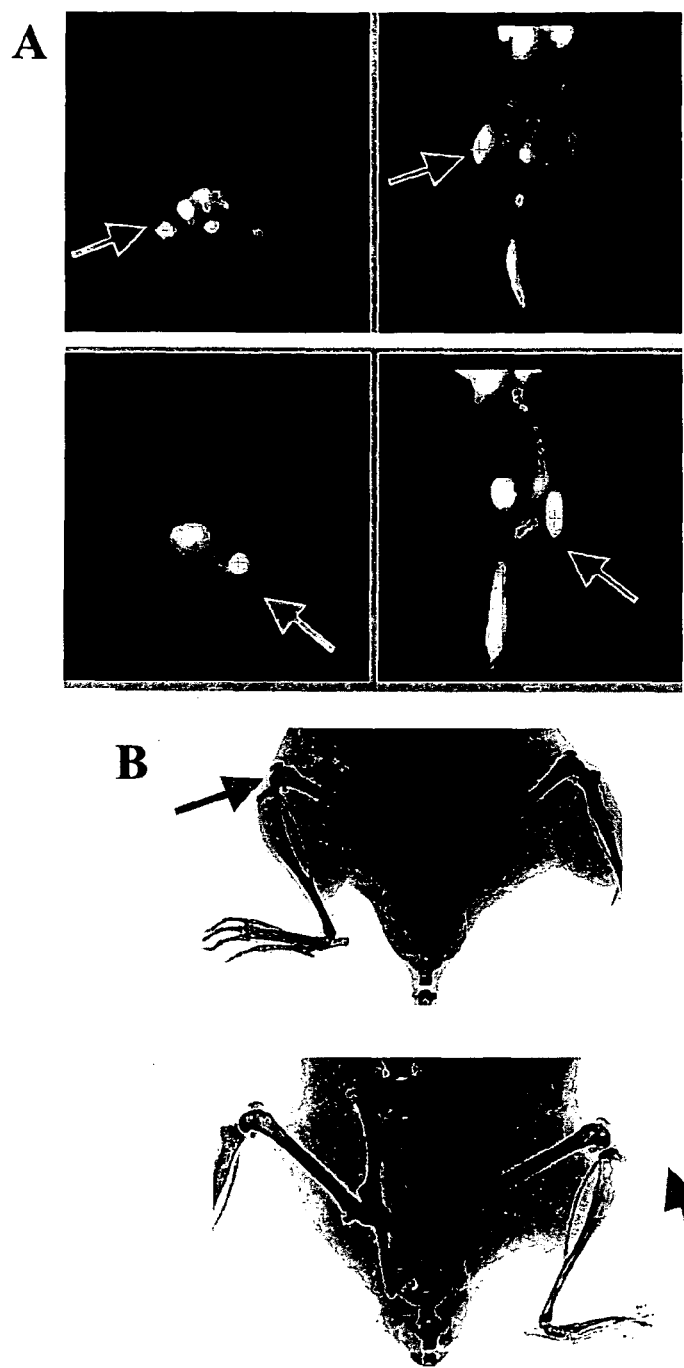
FIG. 11 is X-ray images of mice showing bone metastasis of MDA-MB-231 cells. A: FDG-PET (left, transacial; right coronal). B: X-ray mammography. The animal xenograft was generated by injecting tumor cells intra-tibia.

An experimental animal model was developed for metastasis by injecting MDA-MB-231 cells through the tail vein. Over 90% of the animals developed lung metastasis in 45 days. Another experimental animal model for metastasis was generated by injecting tumor cells intra-tibia. About 50% of animals developed bone metastasis in 45 days. FDG-PET clearly shows the lung metastasis (FIG. 5) and the bone metastasis (FIG. 11) developed from our MDA-MB-231 cells.

Figure 12:
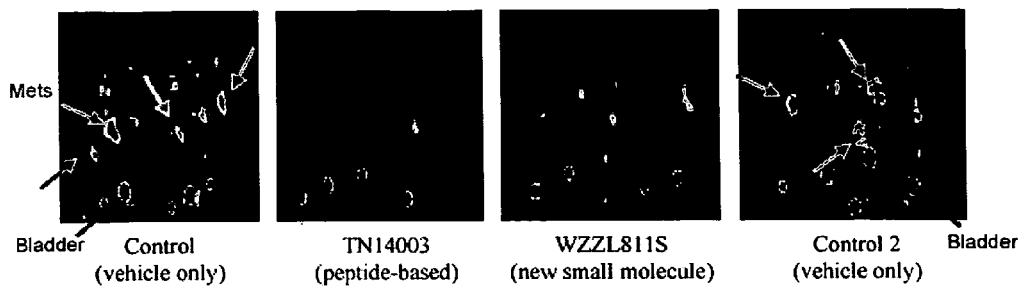
FIG. 12 is FDG-PET images of mice animals described in Example 7.

The metastatic 686LN cells were injected intravenously through the tail vein to generate experimaental animal models for Head & Neck cancer metastasis, modulated via CXCR4. Thirty days later, these metastatic cells metastasized to lungs, liver, and bone marrow in control group (vehicle treated) while they failed to metastasize to any organs in peptide-based CXCR4 antagonist, TN14003 (20 mg/mouse/twice weekly), treated group determined by non-invasive [$^{18}$F]-fluorodeoxyglucose Positron Emission Tomography (FDG-PET) (FIG. 12). Each panel shows FDG-PET image of 6 mive and large lung metastases are indicated by green arrows (bladder shows high FDG-uptake due to excretion, not tumor related). These 3-D projection images show lung metastases well (bone mets and liver mets were apparent in axial section images of mice in control groups, data not shown). The small molecular anti-CXCR4 compound WZZL811S (20 mg/mouse/twice weekly) showed 80% efficacy of TN14003, potentially due to shorter half-life of the compound.

Example 8

Pharmacokinetics of a Novel Anti-HIF1α Compound

Figure 13:
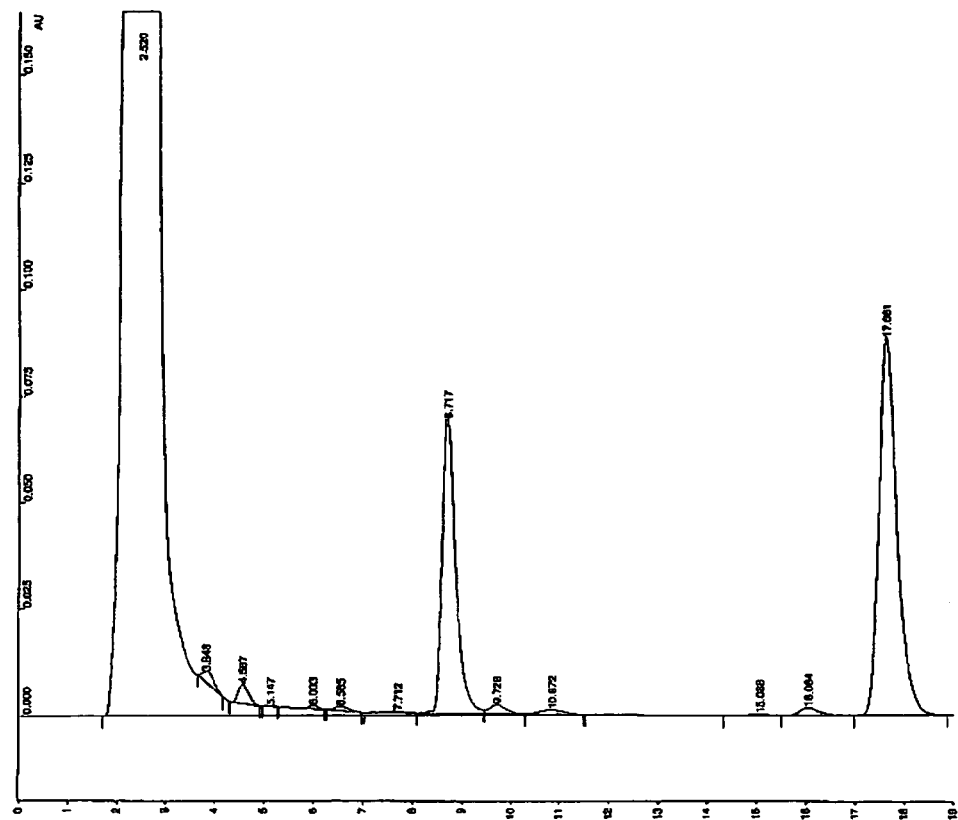
FIG. 13 is a graph of the HPLC analysis performed as described in Example 8.
Figure 17:
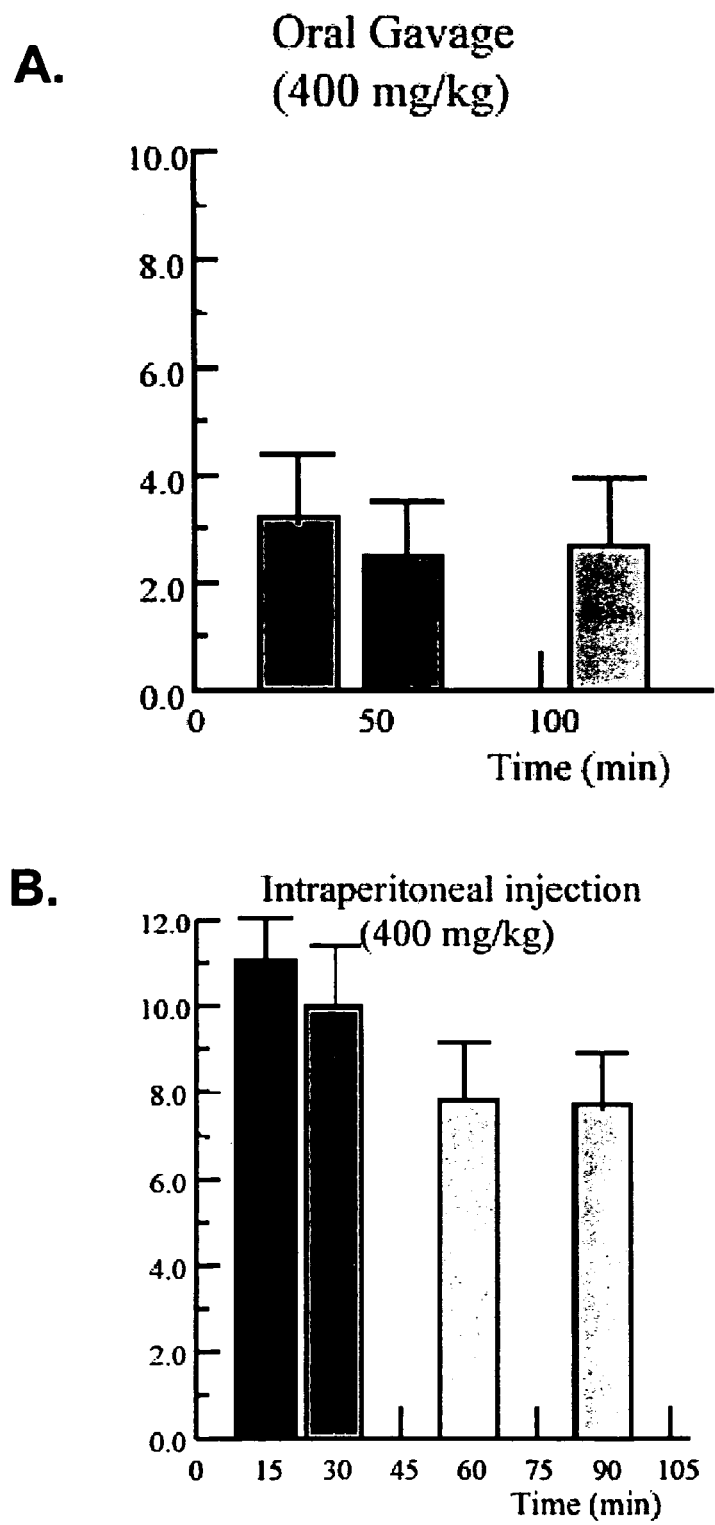
FIG. 17 is graphs of the amount of WZZL811S measured at indicted times after systemic administration, indicating the in vivo stability of WZZL811S and WZ40. A) is a graph of the levels of WZZL811S at indicated times after administration of 400 mg/kg compound by oral gavage. B) is a graph of the levels of WZ40 at 15, 30, 60 and 90 minutes after intraperitoneal injection of 400 mg/kg.

A pharmacokinetic study of a novel anti-HIF-1α small molecule was performed. A stably integrated hypoxia-reporter system of glioma cells transfected with the hypoxia-reporting plasmid (described above) was utilized. A natural product-like small molecule library of 10,000 compounds was screened and the "best hit" was identified. HPLC methodology was developed for quantitatively detecting KCN-1 in plasma and other biological samples. For the pharmacokinetic study, KCN-1 (100 mg/kg) was dissolved in DMSO and administered intravenously to mice. Plasma samples were collected at given time points (0.25, 0.5, 1, 2, 4 and 8 h) and KCN-1 levels were quantified by HPLC. The HPLC system consisted of a Varian Prostar gradient pump, a Prostar autosampler and a Prostar photo diode array detector. The column was a Luna 5μ C18 column (4.6 mm×250 mm, Phenomenex). The retention time of KCN1 and the internal standard were 8.7 and 17.7 min, respectively (FIG. 13). The in vivo stability of WZZL811S and WZ40 were measured after systemic administration of compounds over two hours (FIG. 17).

Example 9

Endothelial Capillary Tube Formation Assay

Figure 14:
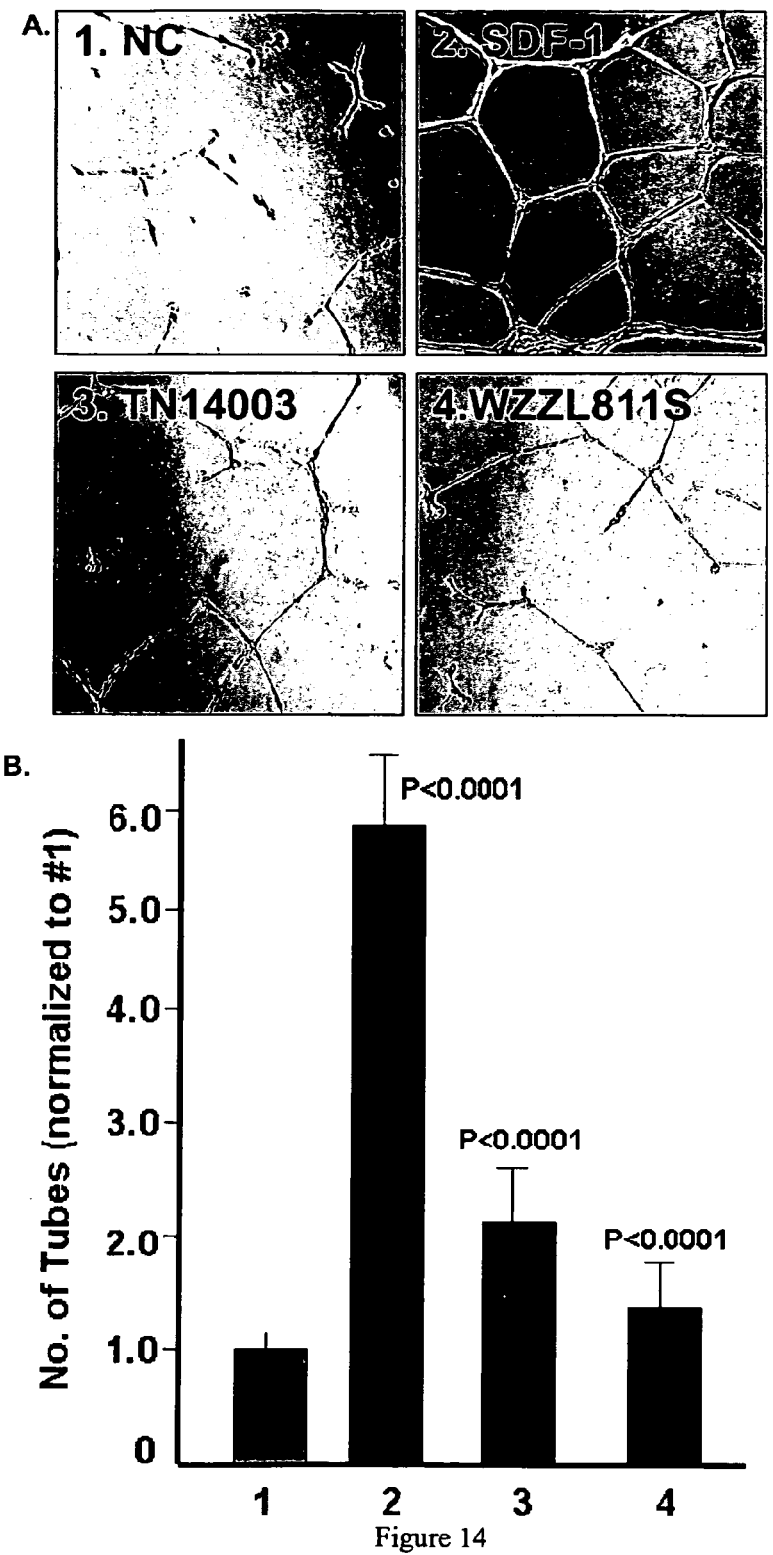
FIG. 14 is images and a graph of endothelial capillary tube formation assay. A) is micrographs of endothelial cell tube formation. B) is a graph of the number of tubes in each treatment group.

The anti-angiogenic effect of test compounds was measured by analyzing endothelial cell growth and tube formation. The angiogenic effect of SDF-1 (100 ng/ml) on capillary formation by human umbilical vein endothelial cells (HUVECs) was examined in vitro using Matrigel-coated 24-well plates precoated with Matrigel and incubated for 18 hours. The angiogenic effect of SDF-1 was inhibted by either 100 nM TN14003 (peptide-based CXCR4 antagonist) or WZZL811S treatment (FIG. 14*a*, graph FIG. 14*b*). FIG. 14B shows a graphical analysis of the number of endothelial cell tubes normalized to control (NC).

Example 10

Efficacy in a Model of HIV

Figure 15:
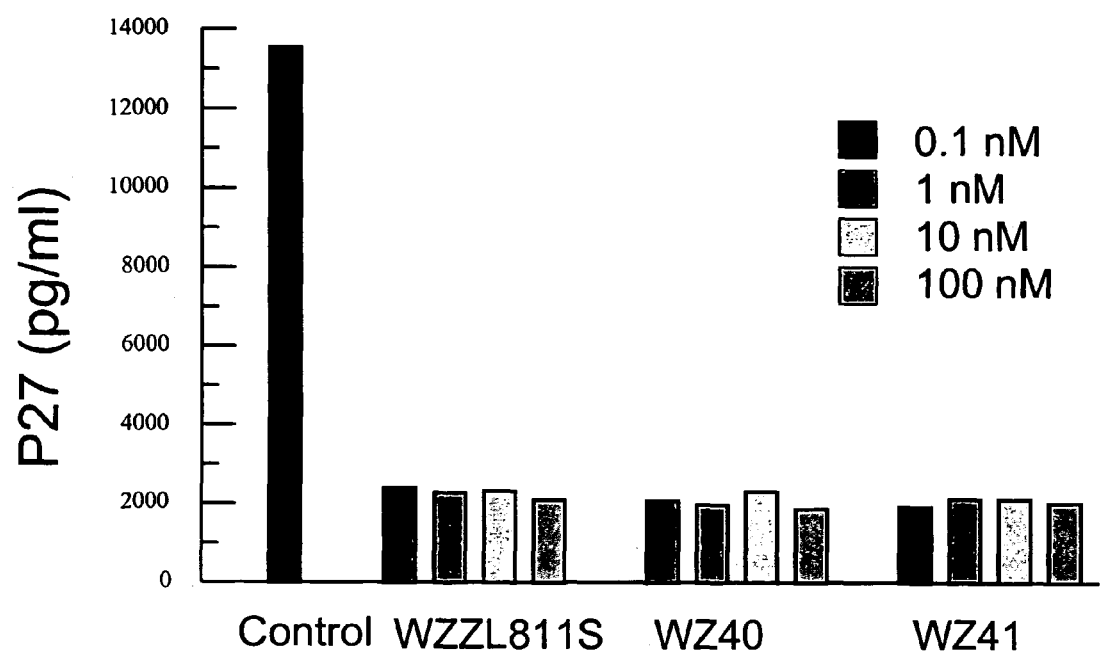
FIG. 15 is a graph of p27 levels measured after incubation with indicated amounts of WZZL811S, WZ40 or WZ41S.
Figure 16:
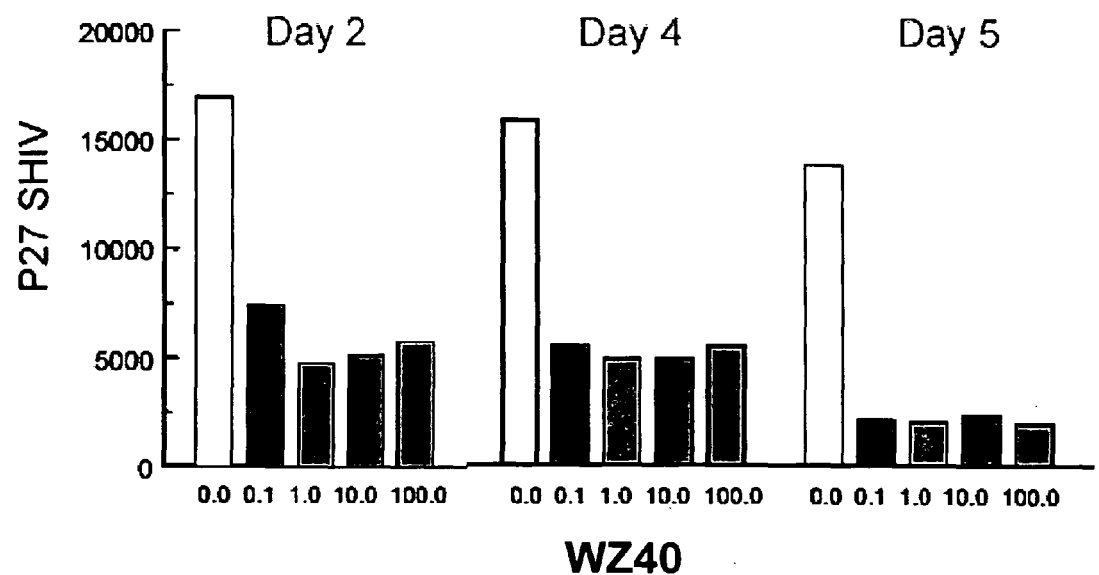
FIG. 16 is a graph of p27 levels measured after incubation with indicated amounts of WZ40 and infection with SHIV for 2, 4 or 5 days.

The effect of the test compounds on HIV infection in model cells was analyzed by p27 antigen capture using SHIV infected cells. Cells were incubated with 0, 0.1, 1, 10 or 100 nM drug prior to infection with SHIV. Viral titer was measured after infection by analyzing levels of p27 antigen. Results for incubation with WZ40, WZZL811S and WZ41 are provided in FIGS. 15 and 16. Test compounds inhibited SHIV infection at all concentrations tested. The inhibition was measurable at 2 days, and continued to 5 day incubations.

Example 11

Compounds Tested Against SDF-1 in Binding to CXCR4

Results of assays showing the IC50 in nM of test compounds binding to CXCR4 when compared to SDF-1 (competition assays) are shown in Table 2 below. The half life of the compounds in mice where determined are also shown.

| Compound | | $IC_{50}$ (nM) vs SCF-1 | $t_{1/2}$ (min) in mice |
|---|---|---|---|
| TN-14003 (Ref) | | MSX-207 | <1 |
| AMD-3100 (Ref) | | MSX-162 | 100 |
| [structure] | | MSX-121 | <10 |
| [structure] | | MSX-122 | <10 |
| [structure] | | MSX-123 | <10 |

-continued

| Compound | IC$_{50}$ (nM) vs SCF-1 | t$_{1/2}$ (min) in mice |
|---|---|---|
| MSX-134 | <10 | 45 |
| MSX-135 | <10 | |
| MSX-146 | <10 | |
| MSX-168 | <100 | 11 |
| MSX-169 | <100 | <5 |
| MSX-173 | >100 | |
| MSX-183 | <10 | 13.7 |

-continued
| Compound | IC$_{50}$ (nM) vs SCF-1 | t$_{1/2}$ (min) in mice |
|---|---|---|
| 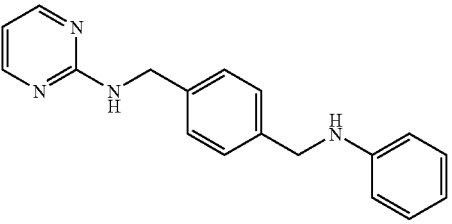 MSX-195 | 10 | |
| 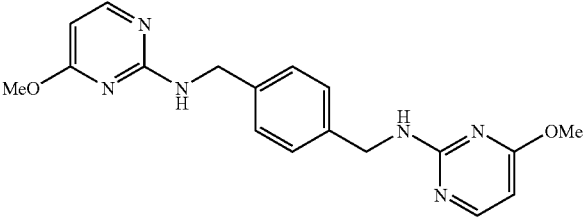 MSX-200 | 10 | |
| 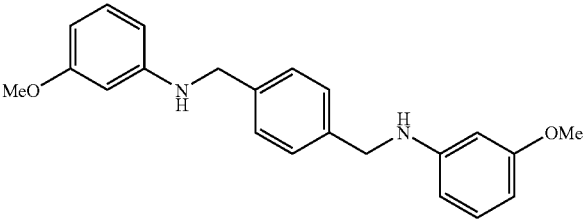 MSX-205 | 1 | 14 |
| 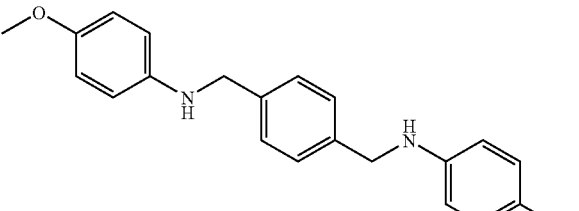 MSX-125 | >10 | |
| 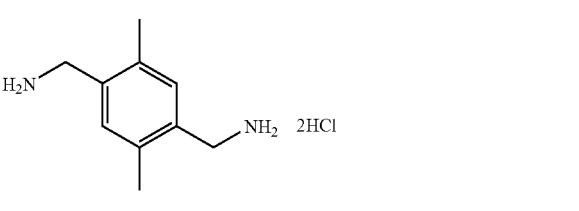 MSX-126 | >1000 | 14.3 |
| 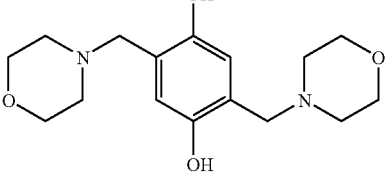 MSX-127 | >1000 | |

-continued
| Compound | IC$_{50}$ (nM) vs SCF-1 | t$_{1/2}$ (min) in mice |
|---|---|---|
| 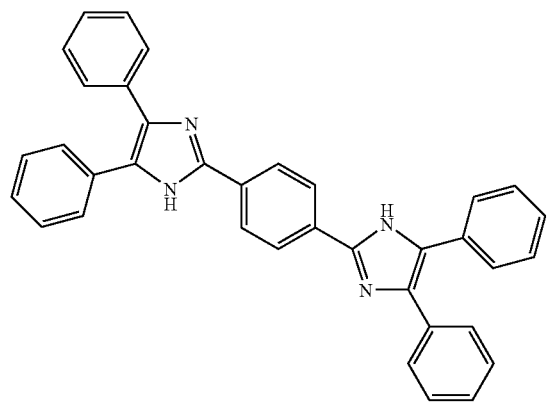 MSX-130 | >1000 | |
| 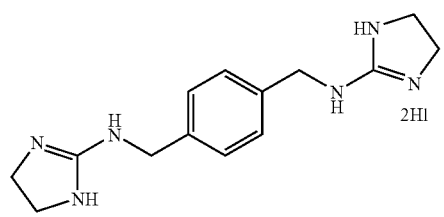 MSX-133 | >1000 | |
| 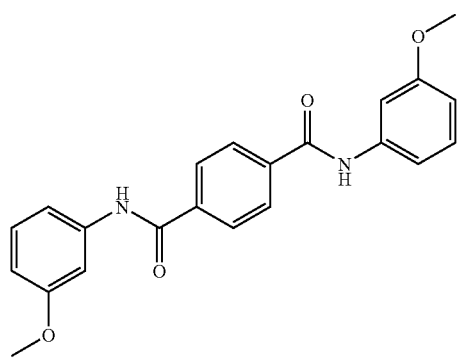 MSX-137 | >1000 | |
| 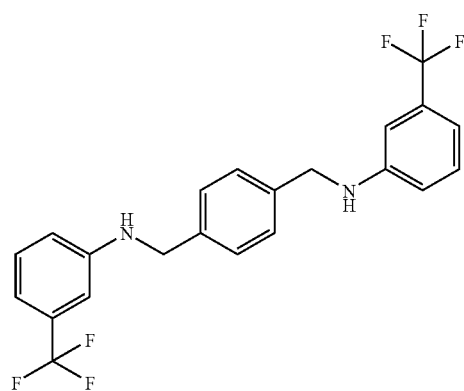 MSX-138 | >1000 | |

-continued

| Compound | | IC$_{50}$ (nM) vs SCF-1 | t$_{1/2}$ (min) in mice |
|---|---|---|---|
| [structure] 2HCl | MSX-139 | 10 | |
| [structure] 2HCl | MSX-140 | 10 | |
| [structure] 2HBr | MSX-141 | >1000 | |
| [structure] | MSX-142 | >1000 | |
| [structure] 2HCl | MSX-156s | >1000 | |
| [structure] 2HCl | MSX-158 | >1000 | |
| [structure] 2HCl | MSX-159s | >1000 | |
| [structure] 2HCl | MSX-160 | >1000 | |
| [structure] 2HCl | MSX-161s | >1000 | |

-continued

| Compound | IC$_{50}$ (nM) vs SCF-1 | t$_{1/2}$ (min) in mice |
|---|---|---|
| MSX-163 | 10 | |
| MSX-164 | >100 | |
| MSX-166 | >1000 | |
| MSX-167 | >100 | |
| MSX-170 | <100 | |

-continued

| Compound | IC$_{50}$ (nM) vs SCF-1 | t$_{1/2}$ (min) in mice |
|---|---|---|
| MSX-171 | >1000 | |
| MSX-172 | 10 | |
| MSX-174 | >100 | |
| MSX-175 | >100 | <5 |
| MSX-176 | >100 | |
| MSX-177 | >1000 | |

-continued

| Compound | | IC$_{50}$ (nM) vs SCF-1 | t$_{1/2}$ (min) in mice |
|---|---|---|---|
| [structure] | MSX-178 | >1000 | |
| [structure] | MSX-179 | >1000 | |
| [structure] | MSX-180 | ND | |
| [structure] | MSX-181 | ND | |
| [structure] | MSX-182 | ND | |
| [structure] | MSX-183 | <10 | |
| [structure] | MSX-184 | >100 | |

-continued

| Compound | IC$_{50}$ (nM) vs SCF-1 | t$_{1/2}$ (min) in mice |
|---|---|---|
| MSX-185 | <100 | |
| MSX-186 | >1000 | |
| MSX-189 | >1000 | |
| MSX-190 | 10 | |
| MSX-191 | 100 | |
| MSX-192 | 1 | <5 |
| MSX-193 | 1 | |

-continued

| Compound | | IC$_{50}$ (nM) vs SCF-1 | t$_{1/2}$ (min) in mice |
|---|---|---|---|
| (structure) | MSX-194 | 1 | |
| (structure) | MSX-196 | 100 | 30 |
| (structure) | MSX-197 | 1 | |
| (structure) | MSX-198 | <100 | |
| (structure) · 2HCl | MSX-199 | ND | 16.5 |
| (structure) | MSX-201 | 1 | |
| (structure) | MSX-202 | 1 | |
| (structure) | MSX-203 | 1 | |

-continued
| Compound | | IC$_{50}$ (nM) vs SCF-1 | t$_{1/2}$ (min) in mice |
|---|---|---|---|
| 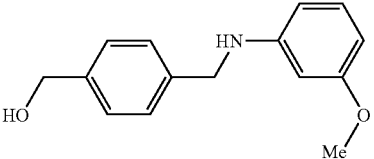 | MSX-204 | 1000 | <5 |
| 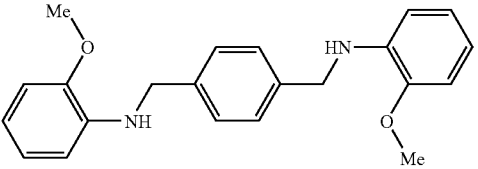 | MSX-206 | 10 | infinite |
| 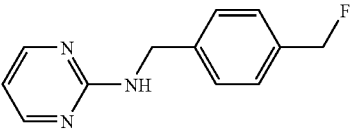 | MSX-207 | 1 | |
| 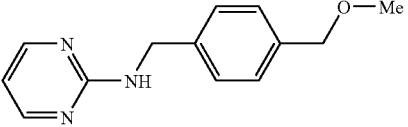 | MSX-208 | 100 | |
| 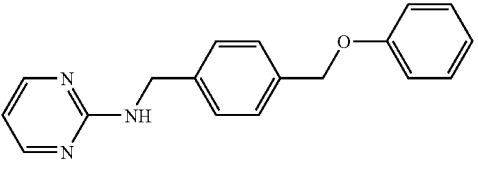 | MSX-209 | 10 | 11 |
| 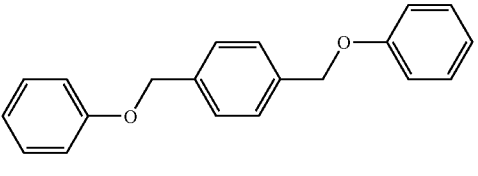 | MSX-210 | 1000 | |
| 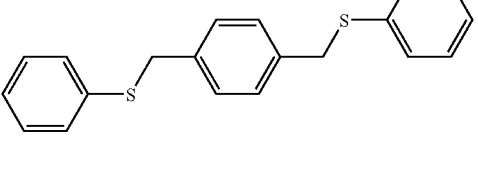 | MSX-211 | 1000 | |
| 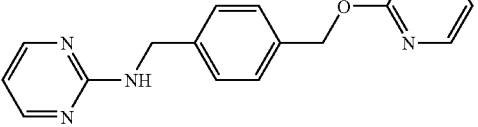 | MSX-212 | 100 | |

-continued

| Compound | IC$_{50}$ (nM) vs SCF-1 | t$_{1/2}$ (min) in mice |
|---|---|---|
| MSX-213 | >1000 | |
| MSX-214 | 100 | |
| MSX-219 | 10 | |
| MSX-221 | 1 | |
| MSX-222 | 1 | |

We claim:

1. A method of treating an inflammatory disorder selected from rheumatoid arthritis, asthma, and allergic airway inflammation comprising administering an effective amount of a compound of Formula XVI

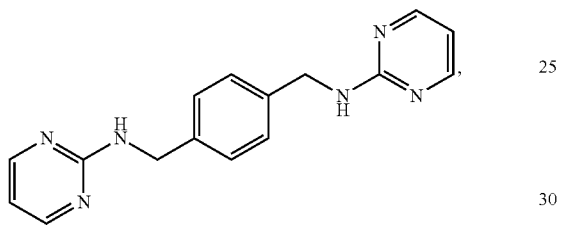

Formula XVI or a pharmaceutically acceptable salt thereof to a patient in need thereof.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Homo sapiens

<400> SEQUENCE: 1
uaaaaucuuc cugcccaccu t       21

<210> SEQ ID NO 2
<211> LENGTH: 21
<212> TYPE: DNA
<213> ORGANISM: Artificial Sequence
<220> FEATURE:
<223> OTHER INFORMATION: Homo sapiens

<400> SEQUENCE: 2
ggaagcuguu ggcugaaaau t       21

```
<210> SEQ ID NO 3
<211> LENGTH: 21
<212> TYPE: DNA
<213> ORGANISM: Artificial Sequence
<220> FEATURE:
<223> OTHER INFORMATION: Homo sapiens

<400> SEQUENCE: 3
uucaaguugg aauugguagt t                                              21
```